US012630602B2

(12) United States Patent  (10) Patent No.: US 12,630,602 B2
Bowrey et al.  (45) Date of Patent: May 19, 2026

(54) METHODS AND COMPOSITIONS FOR TREATING DISEASES AND DISORDERS OF THE NERVOUS SYSTEM

(71) Applicant: Rutgers, The State University of New Jersey, New Brunswick, NJ (US)

(72) Inventors: Hannah E. Bowrey, Highland Park, NJ (US); Gary Aston-Jones, Highland Park, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 453 days.

(21) Appl. No.: 18/047,734

(22) Filed: Oct. 19, 2022

(65) Prior Publication Data

US 2023/0174613 A1 Jun. 8, 2023

Related U.S. Application Data

(62) Division of application No. 16/329,557, filed as application No. PCT/US2017/049629 on Aug. 31, 2017, now Pat. No. 11,542,315.

(60) Provisional application No. 62/381,883, filed on Aug. 31, 2016.

(51) Int. Cl.
| | |
|---|---|
| *C07K 14/705* | (2006.01) |
| *A61K 9/00* | (2006.01) |
| *A61K 31/5513* | (2006.01) |
| *A61K 45/06* | (2006.01) |
| *A61P 9/10* | (2006.01) |
| *A61P 25/00* | (2006.01) |
| *A61P 25/18* | (2006.01) |
| *A61P 25/22* | (2006.01) |
| *A61P 25/24* | (2006.01) |
| *A61P 25/28* | (2006.01) |
| *A61P 25/30* | (2006.01) |
| *C12N 15/86* | (2006.01) |

(52) U.S. Cl.
CPC .......... *C07K 14/705* (2013.01); *A61K 9/0019* (2013.01); *A61K 9/0048* (2013.01); *A61K 31/5513* (2013.01); *A61K 45/06* (2013.01); *A61P 9/10* (2018.01); *A61P 25/00* (2018.01); *A61P 25/18* (2018.01); *A61P 25/22* (2018.01); *A61P 25/24* (2018.01); *A61P 25/28* (2018.01); *A61P 25/30* (2018.01); *C12N 15/86* (2013.01); *C12N 2750/14143* (2013.01); *C12N 2830/008* (2013.01)

(58) Field of Classification Search
CPC .......... A61P 25/00; A61P 25/28; C12N 15/86
See application file for complete search history.

(56) References Cited

U.S. PATENT DOCUMENTS

2003/0021542 A1 1/2003 Lu

FOREIGN PATENT DOCUMENTS

| WO | 2009/105533 A2 | 8/2009 |
|---|---|---|
| WO | 2015/136247 A1 | 9/2015 |
| WO | 2016/161124 A1 | 10/2016 |
| WO | 2017049252 A1 | 3/2017 |
| WO | 2017153995 A2 | 9/2017 |

OTHER PUBLICATIONS

Bowrey (bioRxiv preprint doi: https://doi.org/10.1101/2021.04.20. 440684; this version posted Apr. 21, 2021.*
International Search Report and Written Opinion in corresponding PCT Application No. PCT/US2017/049629, mailed Feb. 6, 2018.
1 Roth, DREADDs for Neuroscientists. Neuron, Feb. 17, 2016, vol. 89, No. 4, pp. 683-694.
European Supplemental Search Report in corresponding European Application No. 17847553.9, dated Apr. 6, 2020.
A. M. Fortress, et al., Designer Receptor Enhance Memory in a Mouse Model of Down Syndrome11 The Journal of Neuroscience, vol. 35, No. 4, Jan. 28, 2015 (Jan. 28, 2015), pp. 1343-135, XP05567975, US ISSN: 0270-6474, DOI: 10.1S23/JNEUROSCI. 26S8-14.2015.
Ilse S. Pienaar, et al.. "Pharmacogenetic stimulation of cholinergic pedunculopontine neurons reverses motor deficits in a rat model of Parkinson's disease," Molecular Neurodegeneration, vol. 10, No. 1, Sep. 23, 2015 (Sep. 23, 2015), XP055619379, DOI: 10.1186/s13024-015-0044-5s.
Japanese Office Action in corresponding Japanese Application No. 2019-531607, dated Aug. 24, 2021 and English translation.
Kyohei Yamamoto, et al., "Cloning and characterization of the mouse pituitary adenylate cyclase-activating polypeptide (PACAP) gene," Gene, 211 (1998), pp. 63-69.
Nina Milosavijevic, et al., "Chemogenetic Activation of Melanospsin Retinal Ganglion Cells Induces Signatures of Arousal and/or Anxiety in Mice," Current Biology, 26, Sep. 12, 2016, pp. 2358-2363.
Japanese Office Action in corresponding Japanese Patent Application No. 2019-531607, dated Apr. 5, 2022 (English translation).
Non Final Office Action in U.S. Appl. No. 16/329,557, mailed Sep. 24, 2021.
Wess (2013, Trends in Pharmacological Sciences, 34:385-392).
Breton-Provencher (Jun. 2021, Front. Neural Circuits, 15:638007; 1-11).
Bowrey (2017, Depress Anxiety, 34:588-595).
Notice of Allowance in U.S. Appl. No. 16/329,557, mailed Aug. 31, 2022.
Milosavljevic, Sep. 12, 2016, Current Biology, 26:2358-2363.

* cited by examiner

Primary Examiner — Valarie E Bertoglio
(74) Attorney, Agent, or Firm — Leason Ellis LLP

(57) ABSTRACT

Methods and compositions for treating diseases or disorders of the nervous system using promoter-driven Designer Receptor Exclusively Activated by Designer Drugs (DREADDs) and DREADD agonists are disclosed.

2 Claims, 6 Drawing Sheets

Figure 1:
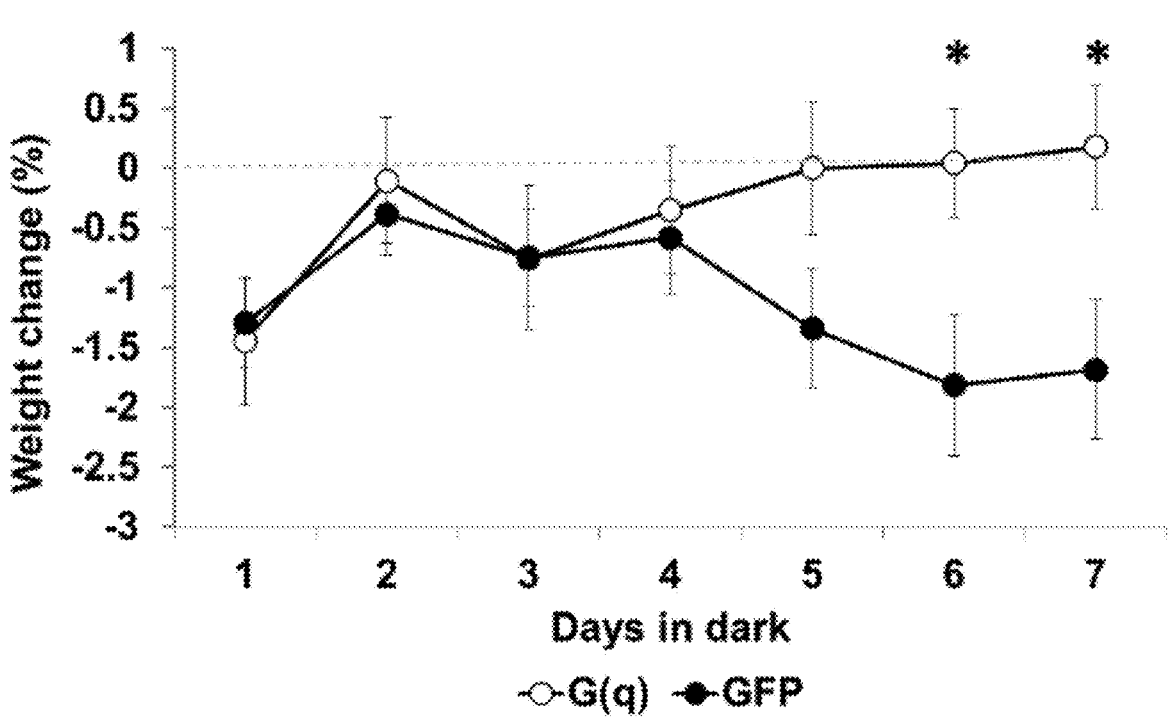

Specification includes a Sequence Listing.

FIG. 2A

CNO IP injection

FIG. 2B

CNO eye drops

FIG. 4A            FIG. 4B            FIG. 4C            FIG. 4D
DD-Control       DD-GFP          DD-Hm3Dq        DL-Control
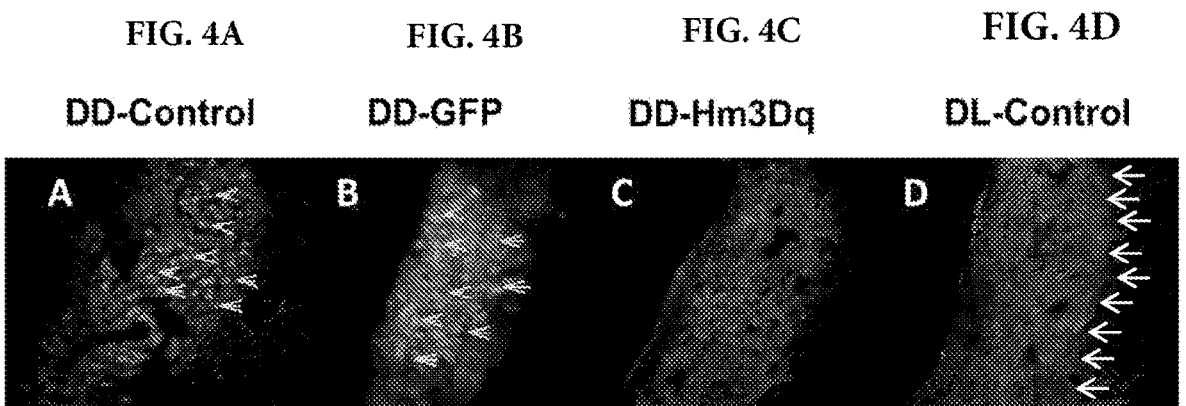
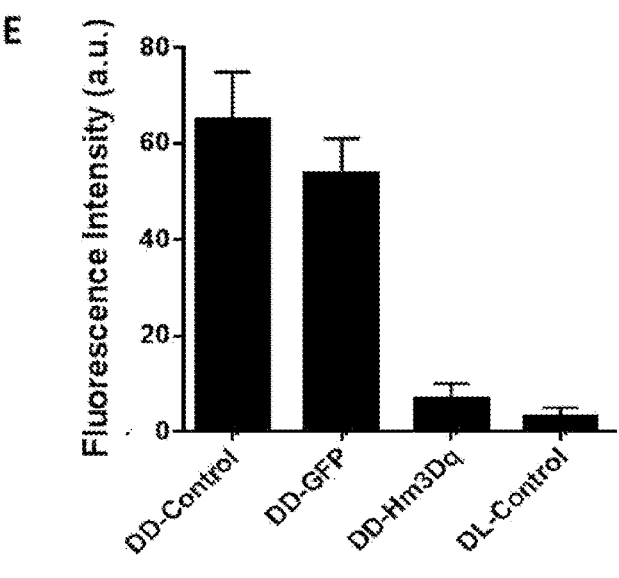
FIG. 4E

SEQUENCE LISTING

```
Sequence total quantity: 11
SEQ ID NO: 1           moltype = DNA  length = 4711
FEATURE                Location/Qualifiers
source                 1..4711
                       mol_type = other DNA
                       organism = synthetic construct
                       note = PACAP- hM3D(Gq)-mCherry Construct
SEQUENCE: 1
caatcttaaa ttttcaatta ttgcagaaaa cacagtgaca tggtttcaat ttttaaaact   60
agtaagagcc acggagagtg tgaaagtgtg tagacaggaa aggtaaagat ccatctgaat  120
actaggacta actcagaaga aaaagctttg cactgaggca gggattaagc aggttctgag  180
cactgggaca ttcgtggaca cagaatccaa gggaagatta atatgaacag cggggtgatt  240
tagacaatga actcccacag taagagcacc actgccaaag cttcaaattt agaggctgtg  300
gtgaaaatta aaccagtggc aaatttcaac atttgcagca tctgcgccca aatagttcag  360
caccaagagc ctggacagca ccacaggctc tcatcctagt ctcatccatc aatctattca  420
gagacagact gtcaacccag ccagactcat tagatattta ctgaaaatcc ttataattct  480
ttcctttaaa acacaaaacg acttccatgt ttagtagcct atttgaaaaa gcatatgcaa  540
ggaattgaga gatcaaaatt aaaattatta ataggagatc ttgatggtgc ttaaatctag  600
agatcagagt tgtcattggt gggggttgag tgaaaattaa gaaaaattag ggactcaata  660
aaaacatgac ttcaccattc tctaaattct acgagttctt tacttgtctt tgagaaatca  720
gtgaaatcga aaaccatcaa aataattgga cttcttaaaa attggattgt gtgagtgaaa  780
ggtgtttatc agaagcggat gactccggat cttatcatcc tggaggactg cacagaatag  840
ttaatatgtt ccttgaggga ctaggatgct gacgtctttt actgataccg gatcattacg  900
tgactggggg agaaaaaaaa ggaagtcata tcatgaataa aaatcggagt gcaacagtgc  960
aaccaaaata ttctgtactt gaaggcagaa agatgttgac aaagaggtgt ctcctgaaac 1020
cacgttcgga cagcttattt tgttaactgc atatataaaa acgagcagaa ggccagtgtc 1080
gacgccacca tgaccttgca caataacagt acaacctcgc ctttgtttcc aaacatcagc 1140
```

```
tcctcctgga tacacagccc ctccgatgca gggctgcccc cgggaaccgt cactcatttc   1200
ggcagctaca atgtttctcg agcagctggc aatttctcct ctccagacgg taccaccgat   1260
gaccctctgg gaggtcatac cgtctggcaa gtggtcttca tcgctttctt aacgggcatc   1320
ctggccttgg tgaccatcat cggcaacatc ctggtaattg tgtcatttaa ggtcaacaag   1380
cagctgaaga cggtcaacaa ctacttcctc ttaagcctgg cctgtgccga tctgattatc   1440
ggggtcattt caatgaatct gtttacgacc tacatcatca tgaatcgatg ggccttaggg   1500
aacttggcct gtgacctctg gcttgccatt gactgcgtag ccagcaatgc ctctgttatg   1560
aatcttctgg tcatcagctt tgacagatac ttttccatca cgaggccgct cacgtaccga   1620
gccaaacgaa caacaaagag agccggtgtg atgatcggtc tggcttgggt catctccttt   1680
gtcctttggg ctcctgccat cttgttctgg caatactttg ttggaaagac aactgtgcct   1740
ccgggagagt gcttcattca gttcctcagt gagcccacca ttactttggg cacagccatc   1800
gctggttttt atatgcctgt caccattatg actattttat actggaggat ctataaggaa   1860
actgaaaagc gtaccaaaga gcttgctggc ctgcaagcct ctgggacaga ggcagagaca   1920
gaaaactttg tccaccccac gggcagttct cgaagctgca gcagttacga acttcaacag   1980
caaagcatga aacgctccaa caggaggaag tatggccgct gccacttctg gttcacaacc   2040
aagagctgga aacccagctc cgagcagatg gaccaagacc acagcagcag tgacagttgg   2100
aacaacaatg atgctgctgc ctccctggag aactccgcct cctccgacga ggaggacatt   2160
ggctccgaga cgagagccat ctactccatc gtgctcaagc ttccgggtca cagcaccatc   2220
ctcaactcca ccaagttacc ctcatcggac aacctgcagg tgcctgagga gggagctggg   2280
atggtggact tggagaggaa agccgacaag ctgcaggccc agaagagcgt ggacgatgga   2340
ggcagttttc caaaaagctt ctccaagctt cccatccagc tagagtcagc cgtggacaca   2400
gctaagactt ctgacgtcaa cctccagtg ggtaagagca cggccactct acctctgtcc   2460
ttcaaggaag ccactctggc caagaggttt gctctgaaga ccagaagtca gatcactaag   2520
cggaaaagga tgtccctggt caaggagaag aaagcggccc agaccctcag tgcgatcttg   2580
cttgccttca tcatcacttg gaccccatac aacatcatgg ttctggtgaa cacctttttgt   2640
gacagctgca tacccaaaac cttttggaat ctgggctact ggctgtgcta catcaacagc   2700
accgtgaacc ccgtgtgcta tgctctgtgc aacaaaacat tcagaaccac tttcaagatg   2760
ctgctgctgt gccagtgtga caaaaaaaag aggcgcaagc agcagtacca gcagagacag   2820
tcggtcattt ttcacaagcg cgcacccgag caggccttga aggatccccc ggtcgccacc   2880
atggtgagca agggcgagga ggataacatg gccatcatca aggagttcat gcgcttcaag   2940
gtgcacatgg agggctccgt gaacggccac gagttcgaga tcgagggcga gggcgagggc   3000
cgcccctacg agggcaccca gaccgccaag ctgaaggtga ccaagggtgg ccccctgccc   3060
ttcgcctggg acatcctgtc ccctcagttc atgtacggct ccaaggccta cgtgaagcac   3120
cccgccgaca tccccgacta cttgaagctg tccttccccg agggcttcaa gtgggagcgc   3180
gtgatgaact tcgaggacgg cggcgtggtg accgtgaccc aggactcctc cctgcaggac   3240
ggcgagttca tctacaaggt gaagctgcgc ggcaccaact cccctccga cggccccgta   3300
atgcagaaga agaccatggg ctgggaggcc tcctccgagc ggatgtaccc cgaggacggc   3360
gccctgaagg gcgagatcaa gcagaggctg aagctgaagg acgcggcca ctacgacgct   3420
gaggtcaaga ccacctacaa ggccaagaag cccgtgcaag tgcccggcgc ctacaacgtc   3480
aacatcaagt tggacatcac ctcccacaac gaggactaca ccatcgtgga acagtacgaa   3540
cgcgccgagg gccgccactc caccggcggc atggacgagc tgtacaagta agaattcgat   3600
atcaagctta tcgataatca acctctggat tacaaaattt gtgaaagatt gactggtatt   3660
cttaactatg ttgctccttt tacgctatgt ggatacgctg ctttaatgcc tttgtatcat   3720
gctattgctt cccgtatggc tttcatttc tcctccttgt ataaatcctg gttgctgtct   3780
ctttatgagg agttgtggcc cgttgtcagg caacgtggcg tggtgtgcac tgtgtttgct   3840
gacgcaaccc ccactggttg gggcattgcc accacctgtc agctcctttc cgggactttc   3900
gctttccccc tccctattgc cacggcggaa ctcatcgccg cctgccttgc ccgctgctgg   3960
acaggggctc ggctgttggg cactgacaat tccgtggtgt tgtcggggaa atcatcgtcc   4020
tttccttggc tgctcgccta tgttgccacc tggattctgc gcgggacgtc cttctgctac   4080
gtcccttcgg ccctcaatcc agcggacctt ccttcccgcg cctgctgcc ggctctgcgg   4140
cctcttccgc gtcttcgcct tcgccctcag acgagtcgga tctccctttg ggccgcctcc   4200
ccgcatcgat accgagcgct gctcgagaga tctacgggtg gcatccctgt gacccctccc   4260
cagtgcctct cctggccctg gaagttgcca ctccagtgcc caccagcctt gtcctaataa   4320
aattaagttg catcattttg tctgactagg tgtccttcta taatattatg gggtggaggg   4380
gggtggtatg gagcaagggg caagttggga agacaacctg tagggcctgc ggggtctatt   4440
gggaaccaag ctggagtgca gtggcacaat cttggctcac tgcaatctcc gcctcctggg   4500
ttcaagcgat tctcctgcct cagcctcccg agttgttggg attccaggca tgcatgacca   4560
ggctcagcta attttttgttt ttttggtaga cacggggttt caccatattg gccaggctgg   4620
tctccaactc ctaatctcag gtgatctacc caccttggcc tcccaaattg ctgggattac   4680
aggcgtgaac cactgctccc ttccctgtcc t                                    4711
```

```
SEQ ID NO: 2              moltype = DNA   length = 4384
FEATURE                  Location/Qualifiers
source                   1..4384
                         mol_type = other DNA
                         organism = synthetic construct
                         note = TAC-1-hM4D(Gi)-mCherry Construct
SEQUENCE: 2
tgctgcagca attcaaagga gaatcttgct gttcgggcag aagaaattca atcaccttgt   60
ggagataatg aaaaagcttc atacttttaa tcagatattg atcgattacc ataatattct   120
cccatagcaa tagctgcagg cataagaaac ggaaagaatg gaagagattt ttaggagaat   180
acaaaaataa ataagtattt gagacttaga tactgccttt agtgacaagg gtgaggatcc   240
tacacactat gttgctggtt tcctagtctt cagcaagaaa gtgtaggaga gaagcaaaaa   300
acgtcctgtt caacccctgc tcctggatgt ggcaaggaag aggagttacc cggcttgaaa   360
caaaagaaat cctaagtctg acacacaatg tcatgtttaa attccccttt ctccaaaatg   420
taaaataaat ctgcttccat cttctaaaat actatgggac taaacatcct tttgttatgc   480
taaggaaaag ccagtattcg cgttgattta aagagggat gttctggtta tagaacgatg   540
ctgtgtctca gaaacactta aatactatta agctagaaat agaagggaaa ataatgcttc   600
cccgcatctc ccctcaagtg tagtcctctt tttttagcct gatttccgac gaaatgtctg   660
```

-continued

```
aatgcctaca gttatttggc catcctgaaa agtgcaactt atcctgacgt ctcgagggac  720
ggaaaagtta ccgaagtcca aggaatgagt cactttgctc aaatttgatg agtaatatca  780
ggtgtcatga aacccagttt cgaaggagag gggagggggc gtcagatctg cagacggaag  840
caggccgctc cggattggat ggcgagacct cgattttcct aaaattgcgt catttagaac  900
ccaattgggt ccagatgtta tgggcatcga cgagttaccg tctcggaaac tctcaatcac  960
gcaagcgaaa ggagaggagg cggctaatta aatattgagc agaaagtcgc gtggggagaa  1020
tgtcacgtgg gtctggaggc tcaaggaggc tgggataaat accgcaaggc actgagcagg  1080
cgaaagagcg cgctcggacc tccttcccgg cggcagctac cgagagtgcg gagcgaccag  1140
cgtgcgctcg gaggaaccag agaaactcag caccccgcgg gactgtccgt cgcagtaagt  1200
gggtaccgtc gacgccacca tggccaactt cacacctgtc aatggcagct cgggcaatca  1260
gtccgtgcgc ctggtcacgt catcatccca caatcgctat gagacggtgg aaatggtctt  1320
cattgccaca gtgacaggct ccctgagcct ggtgactgtc gtgggcaaca tcctggtgat  1380
gctgtccatc aaggtcaaca ggcagctgca gacagtcaac aactacttcc tcttcagcct  1440
ggcgtgtgct gatctcatca taggcgcctt ctccatgaac ctctacaccg tgtacatcat  1500
caagggctac tggcccctgg gcgcgccgtggt ctgcgacctg tggctggccc tggactgcgt  1560
ggtgagcaac gcctccgtca tgaaccttct catcatcagc tttgaccgct acttctgcgt  1620
caccaagcct ctcacctacc ctgcccggcg caccaccaag atggcaggcc tcatgattgc  1680
tgctgcctgg gtactgtcct tcgtgctctg ggcgcctgcc atcttgttct ggcagtttgt  1740
ggtgggtaag cggacggtgc ccgacaacca gtgcttcatc cagttcctgt ccaacccagc  1800
agtgacctttt ggcacagcca ttgctggctt ctacctgcct gtggtcatca tgacggtgct  1860
gtacatccac atctccctgg ccagtcgcag ccgagtccac aagcaccggc ccgagggccc  1920
gaaggagaag aaagccaaga cgctggcctt cctcaagagc ccactaatga agcagagcgt  1980
caagaagccc ccgccgggg aggccgcccg ggaggagctg cgcaatggca agctggagga  2040
ggccccccg ccagcgctgc caccgccacc gcgcccccgtg gctgataagg acacttccaa  2100
tgagtccagc tcaggcagtg ccacccagaa caccaaggaa cgcccagcca cagagctgtc  2160
caccacagag gccaccacgc ccgccatgcc cgcccctccc ctgcagccgc gggccctcaa  2220
cccagcctcc agatggtcca agatccagat tgtgacgaag cagacaggca atgagtgtgt  2280
gacagccatt gagattgtgc ctgccacgcc ggctggcatg cgccctgcgg ccaacgtggc  2340
ccgcaagttc gccagcatcg ctcgcaacca ggtgcgcaag aagcggcaga tggcggcccg  2400
ggagcgcaaa gtgacacgaa cgatctttgc cattctgctg gccttcatcc tcacctggac  2460
gcctacaac gtcatggtcc tggtgaacac cttctgccag agctgcatcc ctgacacggt  2520
gtggtccatt ggctactggc tctgctacgt caacagcacc atcaaccctg cctgctatgc  2580
tctgtgcaac gccacctttta aaaagacctt ccggcacctg ctgctgtgcc agtatcggaa  2640
catcggcact gccaggcggg atccaccggt cgccaccatg gtgagcaagg gcgaggagga  2700
taacatggcc atcatcaagg agttcatgcg cttcaaggtg cacatggagg gctccgtgaa  2760
cggccacgag ttcgagatcg agggcgaggg cgagggccgc ccctacgagg gcacccagac  2820
cgccaagctg aaggtgacca agggtggccc cctgcccttc gcctgggaca tcctgtcccc  2880
tcagttcatg tacggctcca aggcctacgt gaagcacccc gccgacatcc ccgactactt  2940
gaagctgtcc ttccccgagg gcttcaagtg ggagcgcgtg atgaacttcg aggacggcgg  3000
cgtggtgacc gtgacccagg actcctccct gcaggacgtgc gagttcatct acaaggtgaa  3060
gctgcgcggc accaacttcc cctccgacgg ccccgtaatg cagaagaaga ccatgggctg  3120
ggaggcctcc tccgagcgga tgtaccccga ggacggcgcc ctgaagggcg agatcaagca  3180
gaggctgaag ctgaaggacg gcggccacta cgacgctgag gtcaagacca cctacaaggc  3240
caagaagccc gtgcagctgc ccggcgccta caacgtcaac atcaagttgg acatcacctc  3300
ccacaacgag gactacacca tcgtggaaca gtacgaacgc gccgagggcc gccactccac  3360
cggcggcatg gacgagctgt acaagtaaga attcgatatc cagcacagtg gcggccgctc  3420
gagtctagag ggcccttcga aggtaagcct atccctaacc ctctcctcgg tctcgattct  3480
acgcgtaccg gttaatcgat aatcaacctc tggattacaa aatttgtgaa agattgactg  3540
gtattcttaa ctatgttgct cctttttacgc tatgtggata cgctgcttta atgcctttgt  3600
atcatgctat tgcttcccgt atggctttca ttttctcctc cttgtataaa tcctggttgc  3660
tgtctcttta tgaggagttg tggcccgttg tcaggcaacg tggcgtggtg tgcactgtgt  3720
ttgctgacgc aacccccact ggttggggca ttgccaccac ctgtcagctc ctttccggga  3780
ctttcgcttt ccccctccct attgccacgg cggaactcat cgccgcctgc cttgcccgct  3840
gctggacagg ggctcggctg ttgggcactg acaattccgt ggtgttgtcg gggaaatcat  3900
cgtcctttcc ttggctgctc gcctgtgttg ccacctggat tctgcgcggg acgtccttct  3960
gctacgtccc ttcggccctc aatccagcgg accttccttc ccgcggcctg ctgccggctc  4020
tgcggcctct ccgcgtcttcg ccttcgcc ctcagacgag tcggatctcc ctttgggccg  4080
cctccccgca tcgaacccg ctgatcagcc ggtcatcatc accatcacca ttgagtttaa  4140
acccgctgat cagcctcgac tgtgccttct agttgccagc catctgttgt ttgcccctcc  4200
cccgtgcctt ccttgaccct ggaaggtgcc actcccactg tcctttccta ataaaatgag  4260
gaaattgcat cgcattgtct gagtaggtgt cattctattc tggggggtgg ggtggggcag  4320
gacagcaagg gggaggattg ggaagacaat agcaggcatg ctggggatgc ggtgggctct  4380
atgg                                                                4384
```

```
SEQ ID NO: 3          moltype = DNA  length = 2370
FEATURE               Location/Qualifiers
source                1..2370
                      mol_type = other DNA
                      organism = synthetic construct
                      note = PRSx8-HA-hM3D(Gq) Construct
SEQUENCE: 3
taaaaacgcg tataagcttc cgctagacaa atgtgattac ccccgctaga caaatgtgat  60
tacccgcgct agacaaatgt gattaccccg ctagacaaat gtgattaccc cccgctagac  120
aaatgtgatt accccgcta gacaaatgtg attaccccgc ctagacaaat gtgattaccc  180
cgctagacaa atgtgattac ccccgaccag ggcataaatg gccaggtggg accagagagc  240
tcaccccagc cgactctaga accgggatcc accatgtacc catacgatgt tccagattac  300
gctatgacct tgcacaataa cagtacaacc tcgcctttgt ttccaaacat cagctcctcc  360
tggatacaca gcccctccga tgcagggctg ccccgggaa ccgtcactca tttcggcagc  420
tacaatgttt ctcgagcagc tggcaatttc tcctctccag acggtaccac cgatgaccct  480
```

```
ctgggaggtc ataccgtctg gcaagtggtc ttcatcgctt tcttaacggg catcctggcc    540
ttggtgacca tcatcggcaa catcctggta attgtgtcat ttaaggtcaa caagcagctg    600
aagacggtca acaactactt cctcttaagc ctggcctgtg ccgatctgat tatcgggtc     660
atttcaatga atctgtttac gacctacatc atcatgaatc gatgggcctt agggaacttg    720
gcctgtgacc tctggcttgc cattgactgc gtagccagca atgcctctgt tatgaatctt    780
ctggtcatca gctttgacag atactttttcc atcacgaggc cgctcacgta ccgagccaaa    840
cgaacaacaa agagagccgg tgtgatgatc ggtctggctt gggtcatctc ctttgtcctt     900
tgggctcctg ccatcttgtt ctggcaatac tttgttggaa agagaactgt gcctccggga    960
gagtgcttca ttcagttcct cagtgagccc accattactt ttggcacagc catcgctggt   1020
ttttatatgc ctgtcaccat tatgactatt ttatactgga ggatctataa ggaaactgaa   1080
aagcgtacca aagagcttgc tggcctgcaa gcctctggga cagaggcaga gacagaaaac   1140
tttgtccacc ccacgggcag ttctcgaagc tgcagcagtt acgaacttca acagcaaagc   1200
atgaaacgct ccaacaggag gaagtatggc cgctgccact tctggttcac aaccaagagc   1260
tggaaaccca gctccgagca gatggaccaa gaccacagca gcagtgacag ttggaacaac   1320
aatgatgctg ctgcctccct ggagaactcc gcctcctccg acgaggagga cattggctcc   1380
gagacgagag ccatctactc catcgtgctc aagcttccgg gtcacagcac catcctcaac   1440
tccaccaagt taccctcatc ggacaacctg caggtgcctg aggaggagct ggggatggtg   1500
gacttggaga ggaaagccga caagctgcag gcccagaaga gcgtggacga tggaggcagt   1560
tttccaaaaa gcttctccaa gcttcccatc cagctagagt cagccgtgga cacagctaag   1620
acttctgacg tcaactcctc agtgggtaag agcacggcca ctctacctct gtccttcaag   1680
gaagccactc tggccaagag gtttgctctg aagaccagaa gtcagatcac taagcggaaa   1740
aggatgtccc tggtcaagga gaagaaagcg gcccagaccc tcagtgcgat cttgcttgcc   1800
ttcatcatca cttggacccc atacaacatc atggttctgg tgaacacctt ttgtgacagc   1860
tgcataccca aaaccttttg gaatctgggc tactggctgt gctacatcaa cagcaccgtg   1920
aaccccgtgt gctatgctct gtgcaacaaa acattcagaa ccactttcaa gatgctgctg   1980
ctgtgccagt gtgacaaaaa aaagaggcgc aagcagcagt accacagag acagtcggtc   2040
attttttcaca agcgcgcacc cgagcaggcc ttgtaggcgg ccgtacaagt aataggaatt   2100
cacgcgtggt acctctagag tcgacccggg cggccgcttc gagcagacat gataagatac   2160
attgatgagt ttggacaaac cacaactaga atgcagtgaa aaaaatgctt tatttgtgaa   2220
atttgtgatg ctattgcttt atttgtaacc attataagct gcaataaaca agttaacaac   2280
aacaattgca ttcattttat gtttcaggtt caggggagga tgtgggaggt tttttaaagc   2340
aagtaaaacc tctacaaatg tggtaaaatc                                     2370
```

```
SEQ ID NO: 4              moltype = DNA  length = 2030
FEATURE                   Location/Qualifiers
source                    1..2030
                          mol_type = other DNA
                          organism = synthetic construct
                          note = PRSx8-HA-hM4D(Gi) Construct
SEQUENCE: 4
taaaaacgcg tataagcttc cgctagacaa atgtgattac ccccgctaga caaatgtgat     60
tacccgcgct agacaaatgt gattaccccg ctagacaaat gtgattaccc cccgctagac    120
aaatgtgatt accccgcta gacaaatgtg attaccccg ctagacaaat gtgattaccc     180
cgctagacaa atgtgattac ccccgaccag ggcatataatg gccaggtggg accagagagc    240
tcaccccagc cgactctaga accgggatcc accatgtacc catacgatgt tccagattac    300
gctatgtacc catacgatgt tccagattac gctgatgcca acttcacacc tgtcaatggc    360
agctcgggca atcagtccgt gcgcctggtc acgtcatcat cccacaatcg ctatgagacg    420
gtggaaatgg tcttcattgc cacagtgaca ggctccctga gcctggtgac tgtcgtgggc    480
aacatcctgg tgatgctgtc catcaaggtc aacaggcagc tgcagacagt caacaactac    540
ttcctcttca gcctggcgtg tgctgatctc atcataggcg ccttctccat gaacctctac    600
accgtgaca tcatcaaggg ctactggccc ctgggcgcg tggtctgcga cctgtggctg     660
gccctggact gcgtggtgag caacgcctcc gtcatgaacc ttctcatcat cagctttgac    720
cgctacttct gcgtcaccaa gcctctcacc taccctgccc ggcgcaccac caagatggca    780
ggcctcatga ttgctgctgc ctgggtactg tccttcgtgc tctgggcgcc tgccatcttg    840
ttctgcggac gttgtggtgga taagcggacg gtgcccgaca accagtgctt catccagttc    900
ctgtccaacc cagcagtgac ctttggcaca gccattgctg gcttctacct gcctgtggtc    960
atcatgacgg tgctgtacat ccacatctcc ctggccagtc gcagccgagt ccacaagcac   1020
cggcccgagg gcccgaagga gaagaaagcc aagacgctgg ccttcctcaa gagcccacta   1080
atgaagcaga gcgtcaagaa gccccgcccc ggggaggccg cccgggagga gctgcgcaat   1140
ggcaagctgg aggaggcccc ccgccagcg ctgccaccgc caccgcgcgcc cgtggctgat   1200
aaggacactt ccaatgagtc cagctcaggc agtgccaccc agaacaccaa ggaacgccca   1260
gccacagagc tgtccaccac agaggccacc acgcccgcca tgcccgcccc tccctgcag    1320
ccgcgggccc tcaacccagc ctccagatgg tccaagatcc agattgtgac gaagcagaca   1380
ggcaatgagt gtgtgacagc cattgagatt gtgcctgaca cgcggcgtgg catgcgcccct   1440
gcggccaacg tggcccgcaa gttcgccagc atcgctcgca accaggtgcg caagaagcgg   1500
cagatggcgc cccgggagcg caaagtgaca cgaacgatct ttgccattct gctagccttc   1560
atcctcacct ggacgcccta caacgtcatg gtcctggtga cacccttctg ccagagctgc   1620
atccctgaca cggtgtggtc cattggctac tggctctgct acgtcaacag caccatcaac   1680
cctgctgct atgctctgtg caacgccacc tttaaaaaga ccttccggca cctgctgctg   1740
tgccagtatc ggaacatcgg cactgccagg taggaattcg tcgacccggg cggccgcttc   1800
gagcagacat gataagatac attgatgagt ttggacaaac cacaactaga atgcagtgaa   1860
aaaaatgctt tatttgtgaa atttgtgatg ctattgcttt atttgtaacc attataagct   1920
gcaataaaca agttaacaac aacaattgca ttcattttat gtttcaggtt caggggagga   1980
tgtgggaggt tttttaaagc aagtaaaacc tctacaaatg tggtaaaatc               2030
```

```
SEQ ID NO: 5              moltype = DNA  length = 1077
FEATURE                   Location/Qualifiers
source                    1..1077
                          mol_type = other DNA
```

```
                        organism = synthetic construct
                        note = Pituitary Adenylate Cyclase Activating Polypeptide
                        (PACAP) promoter.
SEQUENCE: 5
caatcttaaa ttttcaatta ttgcagaaaa cacagtgaca tggtttcaat ttttaaaact    60
agtaagagcc acggagagtg tgaaagtgtg tagacaggaa aggtaaagat ccatctgaat   120
actaggacta actcagaaga aaaagctttg cactgaggca gggattaagc aggttctgag   180
cactgggaca ttcgtggaca cagaatccaa gggaagatta atatgaacag cggggtgatt   240
tagacaatga actcccacag taagagcacc actgccaaag cttcaaattt agaggctgtg   300
gtgaaaatta aaccagtggc aaatttcaac atttgcagca tctgcgccca aatagttcag   360
caccaagagc ctggacagca ccacaggctc tcatcctagt ctcatccatc aatctattca   420
gagacagact gtcaacccag ccagactcat tagatattta ctgaaaatcc ttataattct   480
ttcctttaaa acacaaaacg acttccatgt ttagtagcct atttgaaaaa gcatatgcaa   540
ggaattgaga gatcaaaatt aaaattatta ataggagatc ttgatggtgc ttaaatctag   600
agatcagagt tgtcattggt gggggttgag tgaaaattaa gaaaaattag ggactcaata   660
aaaacatgac ttcaccattc tctaaattct acgagttctt tacttgtctt tgagaaatca   720
gtgaaatcga aaaccatcaa aataattgga cttcttaaaa attggattgt gtgagtgaaa   780
ggtgtttatc agaagcggat gactccggat cttatcatcc tggaggactg cacagaatag   840
ttaatatgtt ccttgaggga ctaggatgct gacgtctttt actgataccg gatcattacg   900
tgactggggg agaaaaaaaa ggaagtcata tcatgaataa aaatcggagt gcaacagtgc   960
aaccaaaata ttctgtactt gaaggcagaa agatgttgac aaagaggtgt ctcctgaaac  1020
cacgttcgga cagcttattt tgttaactgc atatataaaa acgagcagaa ggccagt      1077

SEQ ID NO: 6                    moltype = DNA   length = 3981
FEATURE                         Location/Qualifiers
source                          1..3981
                                mol_type = other DNA
                                organism = synthetic construct
                                note = PACAP-hM3D(Gq) Construct
SEQUENCE: 6
caatcttaaa ttttcaatta ttgcagaaaa cacagtgaca tggtttcaat ttttaaaact    60
agtaagagcc acggagagtg tgaaagtgtg tagacaggaa aggtaaagat ccatctgaat   120
actaggacta actcagaaga aaaagctttg cactgaggca gggattaagc aggttctgag   180
cactgggaca ttcgtggaca cagaatccaa gggaagatta atatgaacag cggggtgatt   240
tagacaatga actcccacag taagagcacc actgccaaag cttcaaattt agaggctgtg   300
gtgaaaatta aaccagtggc aaatttcaac atttgcagca tctgcgccca aatagttcag   360
caccaagagc ctggacagca ccacaggctc tcatcctagt ctcatccatc aatctattca   420
gagacagact gtcaacccag ccagactcat tagatattta ctgaaaatcc ttataattct   480
ttcctttaaa acacaaaacg acttccatgt ttagtagcct atttgaaaaa gcatatgcaa   540
ggaattgaga gatcaaaatt aaaattatta ataggagatc ttgatggtgc ttaaatctag   600
agatcagagt tgtcattggt gggggttgag tgaaaattaa gaaaaattag ggactcaata   660
aaaacatgac ttcaccattc tctaaattct acgagttctt tacttgtctt tgagaaatca   720
gtgaaatcga aaaccatcaa aataattgga cttcttaaaa attggattgt gtgagtgaaa   780
ggtgtttatc agaagcggat gactccggat cttatcatcc tggaggactg cacagaatag   840
ttaatatgtt ccttgaggga ctaggatgct gacgtctttt actgataccg gatcattacg   900
tgactggggg agaaaaaaaa ggaagtcata tcatgaataa aaatcggagt gcaacagtgc   960
aaccaaaata ttctgtactt gaaggcagaa agatgttgac aaagaggtgt ctcctgaaac  1020
cacgttcgga cagcttattt tgttaactgc atatataaaa acgagcagaa ggccagtgtc  1080
gacgccacca tgaccttgca caataacagt acaacctcgc ctttgtttcc aaacatcagc  1140
tcctcctgga tacacagccc ctccgatgca gggctgcccc cgggaaccgt cactcatttc  1200
ggcagctaca atgtttctcg agcagctggc aatttctcct ctccagacgg taccaccgat  1260
gaccctctgg gaggtcatac cgtctggcaa gtggtcttca tcgctttctt aacgggcatc  1320
ctggccttgg tgaccatcat cggcaacatc ctggtaattg tgtcatttaa ggtcaacaag  1380
cagctgaaga cggtcaacaa ctacttcctc ttaagcctgg cctgtgccga tctgattatc  1440
ggggtcattt caatgaatct gtttacgacc tacatcatca tgaatcgatg ggccttaggg  1500
aacttggcct gtgacctctg gcttgccatt gactgcgtag ccagcaatgc ctctgttatg  1560
aatcttctgg tcatcagctt tgacagatac ttttccatca cgaggccgct cacgtaccga  1620
gccaaacgaa caacaaagag agccggtgtg atgatcggtc tggcttgggt catctccttt  1680
gtcctttggg ctcctgccat cttgttctgg caatactttg ttggaaagag aactgtgcct  1740
ccgggagagt gcttcattca gttcctcagt gagcccacca ttacttttgg cacagccatc  1800
gctggttttt atatgcctgt caccattatg actattttat actggaggat ctataaggaa  1860
actgaaaagc gtaccaaaga gcttgctggc ctgcaagcct ctgggacaga ggcagagaca  1920
gaaaactttg tccaccccac gggcagttct cgaagctgca gcagttacga acttcaacag  1980
caaagcatga aacgctccaa caggaggaag tatggccgct gccacttctg gttcacaacc  2040
aagagctgga acccagctc cgagcagatg gaccaagacc acagcagcag tgacagttgg  2100
aacaacaatg atgctgctgc ctccctggag aactccgcct cctccgacga ggaggacatt  2160
ggctccgaga cgagagccat ctactccatc gtgctcaagc ttccgggtca cagcaccatc  2220
ctcaactcca ccaagttacc ctcatcggac aacctgcagg tgcctgagga ggagctgggg  2280
atggtggact tggagaggaa agccgacaag ctgcagaacc agaagagcgt ggacgatgga  2340
ggcagttttc caaaaagctt ctccaagctt cccatccagc tagagtcagc cgtggacaca  2400
gctaagactt ctgacgtcaa ctcctcagtg ggtaagagca cggccactct acctctgtcc  2460
ttcaaggaag ccactctggc caagaggttt gctctgaaga ccagaagtca gatcactaag  2520
cggaaaagga tgtccctggt caaggagaag aaagcggccc agaccctcag tgcgatcttg  2580
cttgcctca tcatcacttg gaccccatac aacatcatgg ttctggtgaa cacctttgt  2640
gacagctgca tacccaaaac cttttgggat ctgggctact ggctgtgcta tatcaacagc  2700
accgtgaacc ccgtgtgcta tgctctgtgc aacaaaacat tcagaaccac tttcaagatg  2760
ctgctgctgt gccagtgtga caaaaaaaag aggcgcaagc agcagtacca gcagagacag  2820
tcggtcattt ttcacaagcg cgcacccgag caggccttga gaattcgat atcaagctta  2880
tcgataatca acctctggat tacaaaattt gtgaaagatt gactggtatt cttaactatg  2940
```

-continued

```
ttgctccttt tacgctatgt ggatacgctg ctttaatgcc tttgtatcat gctattgctt   3000
cccgtatggc tttcattttc tcctccttgt ataaatcctg gttgctgtct ctttatgagg   3060
agttgtggcc cgttgtcagg caacgtggcg tggtgtgcac tgtgtttgct gacgcaaccc   3120
ccactggttg gggcattgcc accacctgtc agctcctttc cgggactttc gctttccccc   3180
tccctattgc cacggcggaa ctcatcgccg cctgccttgc ccgctgctgg acaggggctc   3240
ggctgttggg cactgacaat tccgtggtgt tgtcggggaa atcatcgtcc tttccttggc   3300
tgctcgccta tgttgccacc tggattctgc gcgggacgtc cttctgctac gtcccttcgg   3360
ccctcaatcc agcggacctt ccttcccgcg gcctgctgcc ggctctgcgg cctcttccgc   3420
gtcttcgcct tcgccctcag acgagtcgga tctccctttg ggccgcctcc ccgcatcgat   3480
accgagcgct gctcgagaga tctacgggtg gcatccctgt gacccctccc cagtgcctct   3540
cctggccctg gaagttgcca ctccagtgcc caccagcctt gtcctaataa aattaagttg   3600
catcattttg tctgactagg tgtccttcta taatattatg gggtggaggg gggtggtatg   3660
gagcaagggg caagttggga agacaacctg tagggcctgc ggggtctatt gggaaccaag   3720
ctggagtgca gtggcacaat cttggctcac tgcaatctcc gcctcctggg ttcaagcgat   3780
tctcctgcct cagcctcccg agttgttggg attccaggca tgcatgacca ggctcagcta   3840
attttttgtt ttttggtaga cacggggttt caccatattg gccaggctgg tctccaactc   3900
ctaatctcag gtgatctacc caccttggcc tcccaaattg ctgggattac aggcgtgaac   3960
cactgctccc ttccctgtcc t   3981
```

SEQ ID NO: 7          moltype = DNA  length = 2343
FEATURE             Location/Qualifiers
source              1..2343
                      mol_type = other DNA
                      organism = synthetic construct
                      note = PRSx8-hM3D(Gq) Construct
SEQUENCE: 7

```
taaaaacgcg tataagcttc cgctagacaa atgtgattac ccccgctaga caaatgtgat   60
tacccgcgct agacaaatgt gattaccccg ctagacaaat gtgattaccc cccgctagac   120
aaatgtgatt accccgcta gacaaatgtg attacccgcg ctagacaaat gtgattaccc   180
cgctagacaa atgtgattac ccccgaccag ggcataaatg gccaggtggg accagagac   240
tcaccccagc cgactctaga accgggatcc accatgatga ccttgcacaa taacagtaca   300
acctcgcctt tgtttccaaa catcagctcc tcctggatac acagccctc cgatgcaggg   360
ctgcccccgg gaaccgtcac tcatttcggc agctacaatg tttctcgagc agctggcaat   420
ttctcctctc cagacggtac caccgatgac cctctgggag gtcataccgt ctggcaagtg   480
gtcttcatcg ctttcttaac gggcatcctg gccttggtga ccatcatcgg caacatcctg   540
gtaattgtgt catttaaggt caacaagcag ctgaagacgg tcaacaacta cttcctctta   600
agcctggcct gtgccgatct gattatcggg gtcatttcaa tgaatctgtt tacgacctac   660
atcatcatga atcgatgggc cttagggaac ttggcctgtg acctctggct tgccattgac   720
tgcgtagcca gcaatgcctc tgttatgaat cttctggtca tcagctttga cagatacttt   780
tccatcacga ggccgctcac gtaccgagcc aaacgaacaa caaagagagc cggtgtgatg   840
atcggtctgg cttgggtcat ctcctttgtc ctttgggctc ctgccatctt gttctggcaa   900
tactttgttg gaaagagaac tgtgcctccg ggagagtgct tcattcagtt cctcagtgag   960
cccaccatta cttttggcac agccatcgct ggttttata tgcctgtcac cattatgact   1020
attttatact ggaggatcta taaggaaact gaaaagcgta ccaaagagct tgctggcctg   1080
caagcctctg ggacagaggc agagacagaa aactttgtcc accccacggg cagttctcga   1140
agctgcagca gttacgaact tcaacagcaa agcatgaaac gctccaacag gaggaagtat   1200
ggccgctgcc acttctggtt cacaaccaag agctggaaac cctccga gcagatggac   1260
caagaccaca gcagcagtga cagttggaac aacaatgatg ctgctgcctc cctggagaac   1320
tccgcctcct ccgacgagga ggacattggc tccgagacga gagccatcta ctccatcgtg   1380
ctcaagcttc cgggtcacag caccatcctc aactccacca agttaccctc atcggacaac   1440
ctgcaggtgc ctgaggagga gctgcaggat gtggacttgg agaggaaagc cgacaagctg   1500
caggcccaga gagcgtgga cgatggaggc agtttccaa aaagcttctc caagcttccc   1560
atccagctag agtcagccgt ggacacagct aagacttctg acgtcaactc ctcagtgggt   1620
aagagcacgg ccactctacc tctgtccttc aaggaagcca ctctggccaa gaggtttgct   1680
ctgaagacca gaagtcagat cactaagcgg aaaaggatgt ccctggtcaa ggagaagaaa   1740
gcggcccaga ccctcagtgc gatcttgctt gccttcatca tcacttggac cccatacaac   1800
atcatggttc tggtgaacac cttttgtgac agctgcatac ccaaaacctt ttggaatctg   1860
ggctactggc tgtgctacat caacagcacc gtgaaccccg tgtgctatgc tctgtgcaac   1920
aaaacattca gaaccacttt caagatgctg ctgctgtgcc agtgtgacaa aaaaaagagg   1980
cgcaagcagc agtaccagca gagacagtcg gtcatttttc acaagcgcgc acccgagcag   2040
gccttgtagg cggccgtaca agtaatagga attcacgcgt ggtacctcta gagtcgaccc   2100
gggcggccgc ttcgagcaga catgataaga tacattgatg agtttggaca aaccacaact   2160
agaatgcagt gaaaaaatg ctttatttgt gaaatttgtg atgctattgc tttatttgta   2220
accattataa gctgcaataa acaagttaac aacaacaatt gcattcattt tatgtttcag   2280
gttcagggggg agatgtggga ggttttttaa agcaagtaaa acctctacaa atgtggtaaa   2340
atc   2343
```

SEQ ID NO: 8          moltype = DNA  length = 2002
FEATURE             Location/Qualifiers
source              1..2002
                      mol_type = other DNA
                      organism = synthetic construct
                      note = PRSx8-hM4D(Gi) Construct
SEQUENCE: 8

```
aaaaacgcgt ataagcttcc gctagacaaa tgtgattacc cccgctagac aaatgtgatt   60
acccgcgcta gacaaatgtg attaccccgc tagacaaatg tgattacccc cgctagacaca   120
aatgtgatta ccccgctag acaaatgtga ttacccgcgc tagacaaatg tgattacccc   180
gctagacaaa tgtgattacc cccgaccagg gcataaatgg ccaggtggga ccagagagct   240
caccccagcc gactctagaa ccgggatcca ccatgatgta cccatacgat gttccagatt   300
```

```
acgctgatgc caacttcaca cctgtcaatg gcagctcggg caatcagtcc gtgcgcctgg    360
tcacgtcatc atcccacaat cgctatgaga cggtggaaat ggtcttcatt gccacagtga    420
caggctccct gagcctggtg actgtcgtgg gcaacatcct ggtgatgctg tccatcaagg    480
tcaacaggca gctgcagaca gtcaacaact acttcctctt cagcctggcg tgtgctgatc    540
tcatcatagg cgccttctcc atgaacctct acaccgtgta catcatcaag ggctactggc    600
ccctgggcgc cgtggtctgc gacctgtggc tggccctgga ctgcgtggtg agcaacgcct    660
ccgtcatgaa ccttctcatc atcagctttg accgctactt ctgcgtcacc aagcctctca    720
cctaccctgc ccggcgcacc accaagatgg caggcctcat gattgctgct gcctgggtac    780
tgtccttcgt gctctgggcg cctgccatct tgttctggca gtttgtggtg ggtaagcgga    840
cggtgcccga caaccagtgc ttcatccagt tcctgtccaa cccagcagtg acctttggca    900
cagccattgc tggcttctac ctgcctgtgg tcatcatgac ggtgctgtac atccacatct    960
ccctggccag tcgcagccga gtccacaagc accggcccga gggcccgaag gagaagaaag   1020
ccaagacgct ggccttcctc aagagcccac taatgaagca gagcgtcaag aagcccccgc   1080
ccgggaggc cgcccgggag gagctgcgca atggcaagct ggaggaggcc ccccgccag   1140
cgctgccacc gccaccggcgc cccgtggctg ataaggacac ttccaatgag tccagctcag   1200
gcagtgccac ccagaacacc aaggaacgcc cagccacaga gctgtccacc acagaggcca   1260
ccacgcccgc catgcccgcc cctccctgc agccgcgggc cctcaaccca gcctccagat   1320
ggtccaagat ccagattgtg acgaagcaga caggcaatga gtgtgtgaca gccattgaa   1380
ttgtgcctgc cacgccggct ggcatgcgc ctgcggccaa cgtgtgccgc aagttcgcca   1440
gcatcgctcg caaccaggtg cgcaagaagc ggcagatggc ggcccgggag cgcaaagtga   1500
cacgaacgat ctttgccatt ctgctagcct tcatcctcac ctggacgccc tacaacgtca   1560
tggtcctggt gaacaccttc tgccagagct gcatccctga caggtgtgg tccattgaga   1620
actggctctg ctacgtcaac agcaccatca accctgcctg ctatgctctg tgcaacgcca   1680
cctttaaaaa gaccttccgg cacctgctgc tgtgccagta tcggaacatc ggcactgcca   1740
ggtaggaatt cgtcgacccg ggcggccgct tcgagcagac atgataagat acattgatga   1800
gtttggacaa accacaacta gaatgcagtg aaaaaaatgc tttatttgtg aaatttgtga   1860
tgctattgct ttatttgtaa ccattataag ctgcaataaa caagttaaca acaacaattg   1920
cattcatttt atgtttcagg ttcaggggga gatgtgggag gttttttaaa gcaagtaaaa   1980
cctctacaaa tgtggtaaaa tc                                            2002
```

SEQ ID NO: 9    moltype = DNA length = 3654
FEATURE      Location/Qualifiers
source       1..3654
          mol_type = other DNA
          organism = synthetic construct
          note = TAC-1-hM4D(Gi) Construct
SEQUENCE: 9

```
tgctgcagca attcaaagga gaatcttgct gttcgggcag aagaaattca atcaccttgt     60
ggagataatg aaaaagcttc atacttttaa tcagatattg atcgattacc ataatattct    120
cccatagcaa tagctgcagg cataagaaac ggaaagaatg gaagagattt ttaggagaat    180
acaaaaataa ataagtattt gagacttaga tactgccttt agtgacaagg gtgaggatcc    240
tacacactat gttgctggtt tcctagtctt cagcaagaaa gtgtaggaga gaagcaaaaa    300
acgtcctgtt caaccctgc tcctggatgt ggcaaggaag aggagttacc cggcttgaaa    360
caaaagaaat cctaagtctg acacacaatg tcatgtttaa attccccttt ctccaaaatg    420
taaaataaat ctgcttccat cttctaaaat actatgggac taaacatcct tttgttatgc    480
taaggaaaag ccagtattcg cgttgattta gaagagggat gttctggtta tagaacgatg    540
ctgtgtctca gaaacactta aatactatta agctagaaat agaagggaaa ataatgcttc    600
cccgcatctc ccctcaagtg tagtcctctt tttttagcct gatttccgac gaaatgtctg    660
aatgcctaca gttatttggc catcctgaaa agtgcaactt atcctgacgt ctcgagggac    720
ggaaaagtta ccgaagtcca aggaatgagt cactttgctc aaatttgatg agtaatatca    780
ggtgtcatga aacccagttt cgaaggagag gggaggggc gtcagatctg cagacggaag    840
caggccgctc cggattggat ggcgagacct cgatttttcct aaaattgcgt catttagaac    900
ccaattgggt ccagatgtta tgggcatcga cgagttaccg tctcggaaac tctcaatcac    960
gcaagcgaaa ggagaggagg cggctaatta aatattgagc agaaagtcgc gtggggagaa   1020
tgtcacgtgg gtctggaggc tcaaggaggc tgggataaat accgcaaggc actgagcagg   1080
cgaaagagcg cgctcggacc tccttcccgg cggcagctac cgagagtgcg gagcgaccag   1140
cgtgcgctcg gaggaaccag agaaactcag caccccgcgg gactgccgt cgcagtaagt   1200
gggtaccgtc gacgccacca tggccaactt cacacctgtc aatggcagct cgggcaatca   1260
gtccgtgcgc ctggtcacgt catcatccca aatcgctat gagacggtgg aaatggtctt   1320
cattgccaca gtgacaggct ggtgactgct ggtgactgtc gtgggcaaca tcctggtgat   1380
gctgtccatc aaggtcaaca ggcagctgca gacagtcaac aactacttcc tcttcagcct   1440
ggcgtgtgct gatctcatca taggcgcctt ctccatgaac ctctacaccg tgtacatcat   1500
caagggctac tggcccctgg gcgccgtggt ctgcgacctg tggctggccc tggactgcgt   1560
ggtgagcaac gcctccgtca tgaaccttct catcatcagc tttgaccgct acttctgcgt   1620
caccaagcct ctcacctacc ctgcccggcg caccaccaag atggcaggcc tcatgattgc   1680
tgctgcctgg gtactgtcct tcgtgctctg ggcgcctgcc atcttgttct ggcagtttgt   1740
ggtgggtaag cggacggtgc ccgacaacca gtgcttcatc agttcctgt ccaacccagc   1800
agtgaccttt ggcacagcca ttgctggctt ctacctgcct gtggtcatca tgacggtgct   1860
gtacatccac atctccctgg ccagtcgcag ccgagtccac aagcaccggc ccgagggccc   1920
gaaggagaag aaagccaaga cgctggcctt cctcaagagc ccactaatga agcagagcgt   1980
caagaagccc cgcccggggg aggccgcccg ggaggagctg cgcaatggca gctggagga   2040
ggcccccccg ccagcgctgc caccgccacc gcgcccgtg gctgataagg acacttccaa   2100
tgagtccagc tcaggcagtg ccaccagaa caccaaggaa cgcccagcca cagagctgtc   2160
caccacagag gccaccacgc ccgccatgcc cgccctccc tgcagccgcg gggccctcaa   2220
cccagcctcc agatggtcca agatccagat tgtgacgaag cagacaggca atgagtgtgt   2280
gacagccatt gagattgtgc ctgccacgcc ggctggcatg cgccctgcg ccaacgtggc   2340
ccgcaagttc gccagcatcg ctcgcaacca ggtgcgcaag aagcggcaga tggcggcccg   2400
ggagcgcaaa gtgacacgaa cgatctttgc cattctgctg ccttcatcc tcacctggac   2460
gccctacaac gtcatggtcc tggtgaacac cttctgccag agctgcatcc ctgacacggt   2520
```

```
gtggtccatt ggctactggc tctgctacgt caacagcacc atcaaccctg cctgctatgc   2580
tctgtgcaac gccaccttta aaaagacctt ccggcacctg ctgctgtgcc agtatcggaa   2640
catcggcact gccaggcgga attcgatatc cagcacagtg gcggccgctc gagtctagag   2700
ggcccttcga aggtaagcct atccctaacc ctctcctcgg tctcgattct acgcgtaccg   2760
gttaatcgat aatcaacctc tggattacaa aatttgtgaa agattgactg gtattcttaa   2820
ctatgttgct cctttacgc tatgtggata cgctgcttta atgcctttgt atcatgctat    2880
tgcttcccgt atggctttca ttttctcctc cttgtataaa tcctggttgc tgtctcttta   2940
tgaggagttg tggcccgttg tcaggcaacg tggcgtggtg tgcactgtgt ttgctgacgc   3000
aaccccact ggttgggggca ttgccaccac ctgtcagctc ctttccggga ctttcgcttt   3060
ccccctccct attgccacgg cggaactcat cgccgcctgc cttgcccgct gctggacagg   3120
ggctcggctg ttgggcactg acaattccgt ggtgttgtcg gggaaatcat cgtcctttcc   3180
ttggctgctc gcctgtgttg ccacctggat tctgcgcggg acgtccttct gctacgtccc   3240
ttcggccctc aatccagcgg accttccttc ccgcggcctg ctgccggctc tgcggcctct   3300
tccgcgtctt cgccttcgcc ctcagacgag tcggatctcc ctttgggccg cctccccgca   3360
tcgaaacccg ctgatcagcc ggtcatcatc accatcacca ttgagtttaa acccgctgat   3420
cagcctcgac tgtgccttct agttgccagc catctgttgt ttgcccctcc cccgtgcctt   3480
ccttgaccct ggaaggtgcc actcccactg tcctttccta ataaaatgag gaaattgcat   3540
cgcattgtct gagtaggtgt cattctattc tggggggtgg ggtggggcag gacagcaagg   3600
gggaggattg ggaagacaat agcaggcatg ctggggatgc ggtgggctct atgg          3654
```

```
SEQ ID NO: 10           moltype = DNA  length = 4424
FEATURE                 Location/Qualifiers
source                  1..4424
                        mol_type = other DNA
                        organism = synthetic construct
                        note = TAC-1-hM3D(Gq)-mCherry Construct
SEQUENCE: 10
tgctgcagca attcaaagga gaatcttgct gttcgggcag aagaaattca atcaccttgt    60
ggagataatg aaaaagcttc atactttaa tcagatattg atcgattacc ataatattct    120
cccatagcaa tagctgcagg cataagaaac ggaaagaatg gaagagattt ttaggagaat    180
acaaaaataa ataagtattt gagacttaga tactgccttt agtgacaagg gtgaggatcc    240
tacacactat gttgctggtt tcctagtctt cagcaagaaa gtgtaggaga gaagcaaaaa    300
acgtcctgtt caaccctgc tcctggatgt ggcaaggaag aggagttacc cggcttgaaa     360
caaagaaat cctaagtctg acacacaatg tcatgtttaa attcccttt ctccaaaatg      420
taaaataaat ctgcttccat cttctaaaat actatgggac taaacatcct tttgttatgc    480
taaggaaaag ccagtattcg cgttgattta gaagagggat gttctggtta tagaacgatg    540
ctgtgtctca gaaacactta aatactatta agctagaaat agaagggaaa ataatgcttc    600
cccgcatctc ccctcaagtg tagtcctctt tttttagcct gatttccgac gaaatgtctg    660
aatgcctaca gttatttggc catcctgaaa agtgcaactt atcctgacgt ctcgagggac    720
ggaaaagtta ccgaagtcca aggaatgagt cactttgctc aaatttgatg agtaatatca    780
ggtgtcatga aacccagttt cgaaggagag gggaggggc gtcagatctg cagacggaag     840
caggccgctc cggattggat ggcgagacct cgattttcct aaaattgcgt catttagaac    900
ccaattgggt ccagatgtta tgggcatcga cgagttaccg tctcggaaac tctcaatcac    960
gcaagcgaaa ggagaggagg cggctaatta aatattgagc agaaagtcgc gtggggagaa   1020
tgtcacgtgg gtctggaggc tcaaggaggc tgggataaat accgcaaggc actgagcagg   1080
cgaaagagc cgctccggacc tccttccggg cggcagctac cgagagtgcg gagcgaccag    1140
cgtgcgctcg gaggaaccag agaaactcag cacccgccg gactgtccgt gcagtaagt     1200
gggtaccgtc gacgccacca tgaccttgca caataacagt acaacctcgc ctttgtttcc   1260
aaacatcagc tcctcctgga tacacagccc ctccgatgca gggctgcccc cgggaaccgt   1320
cactcatttc ggcagctaca atgtttctcg agcagctggc aatttctcct ctccagacgg   1380
taccaccgat gaccctctgg gaggtcatac cgtctggcaa gtggtcttca tcgctttctt   1440
aacgggcatc ctggccttgg tgaccatcat cggcaacatc ctggtaattg tgtcatttaa   1500
ggtcaacaag cagctgaaga cggtcaacaa ctacttcctc ttaagcctgg cctgtgccga   1560
tctgattatc ggggtcattt caatgaatct gtttacgacc tacatcatca tgaatcgatg   1620
ggccttaggg aacttggcct gtgacctctg gcttgccatt gactgcgtag ccagcaatgc   1680
ctctgttatg aatcttctgg tcatcagctt tgacagatac ttttccatca cgaggccgct   1740
cacgtaccga gccaaacgaa caacaaagag agccggtgtg atgatcggtc tggcttgggt   1800
catctccttt gtcctttggg ctcctgccat cttgttctgg caatactttg ttggaaagag   1860
aactgtgcct ccgggagagt gcttcattca gttcctcagt gagcccacca ttacttttgg   1920
cacagccatc gctggttttt atatgcctgt caccattatg actatttat actggaggat    1980
ctataaggaa actgaaaagc gtaccaaaga gcttgctggc ctgcaagcct ctgggacaga   2040
ggcagagaca gaaaactttg tccaccccac gggcagttct cgaagctgca gcagttacga   2100
acttcaacag caaagcatga aacgctccaa caggaggaag tatggccgct gccacttctg   2160
gttcacaacc aagagctgga aacccagctc cgagcagatg acccaagacc acagcagcga   2220
tgacagttgg aacaacaatg atgctgctgc ctccctggag aactccgcct cctccgacga   2280
ggaggacatt ggctccgaga cgagagccat ctactccatc gtgctcaagc ttccgggtca   2340
cagcaccatc ctcaactcca ccaagttacc ctcatcggac aacctgcagg tgcctgagga   2400
ggagctgggg atggtggact tggagaggaa agccgacaag ctgcaggccc agaagagcgt   2460
ggacgatgga ggcagttttc caaaaagctt cccatccagc tagagtcgac cgtgcacaca   2520
cgtggcacaca gctaagactt ctgacgtcaa ctcctcagtg ggtaagagca cggccactct   2580
acctctgtcc ttcaaggaag ccactctggc caagaggttt gctctgaaga ccagaagtca   2640
gatcactaag cggaaaagga tgtccctggt caaggagaag aaagcggccc agaccctcag   2700
tgcgatcttg cttgccttca tcatcacttg gacccccatac aacatcatgg ttctggtgaa   2760
cacctttttgt gacagctgca tacccaaaac cttttgggct ggtggctgtgcta          2820
catcaacagc accgtgaacc ccgtgtgcta tgctctgtgc aacaaaacat tcagaaccac   2880
tttcaagatg ctgctgctgt gccagtgtga caaaaaaaag aggcgcaagc agcagtacca   2940
gcagagacag tcggtcattt ttcacaagcg cgcacccgag caggccttga aggatccacc   3000
ggtcgccacc atggtgagca aaggcgagga ggataacatg gccatcatca aggagttcat   3060
gcgcttcaag gtgcacatgg agggctccgt gaacggccac gagttcgaga tcgagggcga   3120
```

-continued

```
gggcgagggc cgcccctacg agggcaccca gaccgccaag ctgaaggtga ccaagggtgg   3180
ccccctgccc ttcgcctggg acatcctgtc ccctcagttc atgtacggct ccaaggccta   3240
cgtgaagcac ccgccgaca tccccgacta cttgaagctg tccttccccg agggcttcaa   3300
gtgggagcgc gtgatgaact tcgaggacgg cggcgtggtg accgtgaccc aggactcctc   3360
cctgcaggac ggcgagttca tctacaaggt gaagctcgc ggcaccaact tcccctccga   3420
cggcccgta atgcagaaga agaccatggg ctgggaggcc tcctccgagc ggatgtaccc   3480
cgaggacggc gccctgaagg gcgagatcaa gcagaggctg aagctgaagg acggcggcca   3540
ctacgacgct gaggtcaaga ccacctacaa ggccaagaag cccgtgcagc tgcccggcgc   3600
ctacaacgtc aacatcaagt tggacatcac ctcccacaac gaggactaca ccatcgtgga   3660
acagtacgaa cgcgccgagg gccgccactc caccggcggc atggacgagc tgtacaagta   3720
agaattcgat atccagcaca gtggcggccg ctcgagtcta gagggccctt cgaaggtaag   3780
cctatcccta accctctcct cggtctcgat tctacgcgta ccggttaatc gataatcaac   3840
ctctggatta caaaatttgt gaaagattga ctggtattct taactatgtt gctcctttta   3900
cgctatgtgg atacgctgct ttaatgcctt tgtatcatgc tattgcttcc cgtatggctt   3960
tcattttctc ctccttgtat aaatcctggt tgctgtctct ttatgaggag ttgtggcccg   4020
ttgtcaggca acgtggcgtg gtgtgcactg tgtttgctga cgcaacccccc actggttggg   4080
gcattgccac cacctgtcag ctcctttccg ggactttcgc tttccccctc cctattgcca   4140
cggcggaact catcgccgcc tgccttgccc gctgctggac aggggctcgg ctgttgggca   4200
ctgacaattc cgtggtgttg tcggggaaat catcgtcctt ccttggctg ctcgcctgtg   4260
ttgccacctg gattctgcgc gggacgtcct tctgctacgt ccccttcggcc ctcaatccag   4320
cggaccttcc ttcccgcggc ctgctgccgg ctctgcggcc tcttccgcgt cttcgccttc   4380
gccctcagac gagtcggatc tccctttggg ccgcctcccc gcat   4424
```

```
SEQ ID NO: 11              moltype = DNA   length = 4379
FEATURE                    Location/Qualifiers
source                     1..4379
                           mol_type = other DNA
                           organism = synthetic construct
                           note = PACAP-hM4D(Gi)-mCherry Construct
SEQUENCE: 11
caatcttaaa ttttcaatta ttgcagaaaa cacagtgaca tggtttcaat ttttaaaact   60
agtaagagcc acggagagtg tgaaagtgtg tagacaggaa aggtaaagat ccatctgaat   120
actaggacta actcagaaga aaaagctttg cactgaggca gggattaagc aggttctgag   180
cactgggaca ttcgtggaca cagaatccaa gggaagatta atatgaacag cggggtgatt   240
tagacaatga actcccacag taagagcacc actgccaaag cttcaaattt agaggctgtg   300
gtgaaaatta aaccagtggc aaatttcaac atttgcagca tctgcgccca aatagttcag   360
caccaagagc ctggacagca ccacaggctc tcatcctagt ctcatccatc aatctattca   420
gagacagact gtcaacccag ccagactcat tagatattta ctgaaaatcc ttataattct   480
ttcctttaaa acacaaaacg acttccatgt ttagtagcct atttgaaaaa gcatatgcaa   540
ggaattgaga gatcaaaatt aaaattatta ataggagatc ttgatggtgc ttaaatctag   600
agatcagagt tgtcattggt gggggttgag tgaaaattaa gaaaaattag ggactcaata   660
aaaacatgac ttcaccattc tctaaattct acgagttctt tacttgtctt tgagaaatca   720
gtgaaatcga aaccatcaa aataattgga cttcttaaaa attggattgt gtgagtgaaa   780
ggtgtttatc agaagcggat gactccggat cttatcatcc tggaggactg cacagaatag   840
ttaatatgtt ccttgaggga ctaggatgct gacgtcttt actgataccg gatcattacg   900
tgactggggg agaaaaaaaa ggaagtcata tcatgaataa aaatcggagt gcaacagtgc   960
aaccaaaata ttctgtactt gaaggcagaa agatgttgac aaagaggtgt ctcctgaaac   1020
cacgttcgga cagcttattt tgttaactgc atatataaaa acgagcagaa ggccagtgtc   1080
gacgccacca tggccaactt cacacctgtc aatggcagct cggcaatca gtccgtgcgc   1140
ctggtcacgt catcatccca caatcgctat gagacggtgg aaatggtctt cattgccaca   1200
gtgacagcct ccctgagcct ggtgactgtc gtgggcaaca tcctggtgat gctgtccatc   1260
aaggtcaaca ggcagctgca gacagtcaac aactacttcc tcttcagcct ggcgtgtgct   1320
gatctcatca taggcgcctt ctccatgaac ctctacaccg tgtacatcat caagggctac   1380
tggcccctgg gcgccgtggt ctgcgacctg tggctggccc tggactgcgt ggtgagcaac   1440
gcctccgtca tgaaccttct catcatcagc tttgaccgct acttctgcgt caccaagcct   1500
ctcacctacc ctgcccggcg caccaccaag atggcaggcc tcatgattgc tgctgcctgg   1560
gtactgtcct tcgtgctctg ggcgcctgcc atcttgttct ggcagtttgt ggtgggtaag   1620
cggacggtgc ccgacaacca gtgcttcatc cagttcctgt ccaacccagc agtgaccttt   1680
ggcacagcca ttgctggctt ctacctgcct gtggtcatca tgacggtgct gtacatccac   1740
atctccctgg ccagtcgcag ccgagtccac aagcaccggc agggggccc gaaggagaag   1800
aaagccaaga cgctggcctt cctcaagagc ccactaatga agcagagcgt caagaagccc   1860
ccgcccgggg aggccgcccg ggaggagctg cgcaatggca agctggagga ggccccccg   1920
ccagcgctgc caccgccacc gcgccccgtg gctgataagg acacttccaa tgagtccagc   1980
tcaggcaggc ccaccagaa caccaaggaa cgcccagcca cagctgtc caccacagag   2040
gccaccacgc ccgccatgcc cgcccctccc ctgcagccgc gggccctcaa cccagcctcc   2100
agatggtcca agatccagat tgtgacgaag cagacaggca atgagtgtgt gacagccatt   2160
gagattgtgc tgccacgcc ggctggcatg cgccctgcgg ccaacgtggc ccgcaagttc   2220
gccagcatcg ctcgcaacca ggtgcgcaag aagcggcaga tggccgcccg ggagcgcaaa   2280
gtgacacgaa cgatcttgc cattctgctg gccttcatcc tcacctggac gccctacaac   2340
gtcatggtcc tggtgaacac cttctgccag agctgcatcc ctgacacggt gtggtccatt   2400
ggctactggc tctgctacgt caacagcacc atcaaccctg cctgctatgc tctgtgcaac   2460
gccacctta aaaagacctt ccggcacctg ctgctgtgcc agtatcggaa catcggcact   2520
gccaggcggg gatcccccgg tcgccaccat ggtgagcaag ggcgaggagg ataacatggc   2580
catcatcaag gagttcatgc gcttcaaggt gcacatggag ggctccgtga acggccacga   2640
gttcgagatc gagggcgagg gcgagggccg cccctacgag ggcacccaga ccgccaagct   2700
gaaggtgacc aagggtggcc ccctgccctt cgcctgggac atcctgtccc ctcagttcat   2760
gtacggctcc aaggcctacg tgaagcaccc cgccgacatc cccgactact gaagctgtc   2820
cttcccccag ggcttcaagt gggagcgcgt gatgaacttc gaggacggcg cgtggtgac   2880
cgtgacccag gactcctccc tgcaggacgg cgagttcatc tacaaggtga agctgcgcgg   2940
```

-continued

```
caccaacttc ccctccgacg gccccgtaat gcagaagaag accatgggct gggaggcctc  3000
ctccgagcgg atgtaccccg aggacggcgc cctgaagggc gagatcaagc agaggctgaa  3060
gctgaaggac ggcggccact acgacgctga ggtcaagacc acctacaagg ccaagaagcc  3120
cgtgcagctg cccggcgcct acaacgtcaa catcaagttg gacatcacct cccacaacga  3180
ggactacacc atcgtggaac agtacgaacg cgccgagggc cgccactcca ccggcggcat  3240
ggacgagctg tacaagtaag aattcgatat caagcttatc gataatcaac ctctggatta  3300
caaaatttgt gaaagattga ctggtattct taactatgtt gctcctttta cgctatgtgg  3360
atacgctgct ttaatgcctt tgtatcatgc tattgcttcc cgtatggctt tcattttctc  3420
ctccttgtat aaatcctggt tgctgtctct ttatgaggag ttgtggcccg ttgtcaggca  3480
acgtggcgtg gtgtgcactg tgtttgctga cgcaaccccc actggttggg gcattgccac  3540
cacctgtcag ctcctttccg ggactttcgc tttccccctc cctattgcca cggcggaact  3600
catcgccgcc tgccttgccc gctgctggac aggggctcgg ctgttgggca ctgacaattc  3660
cgtggtgttg tcggggaaat catcgtcctt tccttggctg ctcgcctatg ttgccacctg  3720
gattctgcgc gggacgtcct tctgctacgt cccttcggcc ctcaatccag cggaccttcc  3780
ttcccgcggc ctgctgccgg ctctgcggcc tcttccgcgt cttcgccttc gccctcagac  3840
gagtcggatc tccctttggg ccgcctcccc gcatcgatac cgagcgctgc tcgagagatc  3900
tacgggtggc atccctgtga cccctcccca gtgcctctcc tggccctgga agttgccact  3960
ccagtgccca ccagccttgt cctaataaaa ttaagttgca tcattttgtc tgactaggtg  4020
tccttctata atattatggg gtggaggggg gtggtatgga gcaaggggca agttgggaag  4080
acaacctgta gggcctgcgg ggtctattgg gaaccaagct ggagtgcagt ggcacaatct  4140
tggctcactg caatctccgc ctcctgggtt caagcgattc tcctgcctca gcctcccgag  4200
ttgttgggat tccaggcatg catgaccagg ctcagctaat ttttgttttt ttggtagaga  4260
cggggtttca ccatattggc caggctggtc tccaactcct aatctcaggt gatctaccca  4320
ccttggcctc ccaaattgct gggattacag gcgtgaacca ctgctccctt ccctgtcct   4379
```

METHODS AND COMPOSITIONS FOR TREATING DISEASES AND DISORDERS OF THE NERVOUS SYSTEM

CROSS-REFERENCE TO RELATED APPLICATIONS

This application claims priority to U.S. Provisional Patent Application Ser. No. 62/381,883, filed Aug. 31, 2016, which is incorporated herein by reference in its entirety.

SEQUENCE LISTING

The instant application contains a Sequence Listing which has been submitted electronically in XML format and is hereby incorporated by reference in its entirety. Said XML copy, created on Jan. 19, 2023, is named, 10491_006090-US1_SL.xml and is 48,067 bytes in size.

FIELD OF THE INVENTION

The present invention relates to the field of diseases and disorders of the nervous system. Methods and compositions for treating diseases or disorders of the nervous system using promoter-driven Designer Receptor Exclusively Activated by Designer Drugs (DREADDs) and DREADD agonists are disclosed.

BACKGROUND OF THE INVENTION

Diseases and disorders of the nervous system create a significant burden of morbidity and mortality worldwide. Therapeutic treatments are often ineffective because they lack cell-type specificity, even when combined with psychological intervention. Therefore, improved and effective therapeutic treatments are highly desired.

The present invention uses a cell-specific approach to treat diseases and disorders of the nervous system. It was found that neurological pathways associated with photic regulation can be controlled through the retina by leveraging Designer Receptors Exclusively Activated by Designer Drugs (DREADDs). The present invention provides a therapeutic treatment by targeting retinal cells for DREADD expression and circumventing neurosurgical problems associated with injecting DREADDs into the brain. The present invention also allows for stimulation of targeted neurological pathways, especially the brain nucleus locus coeruleus, by natural circuit inputs to provide manipulations of the locus coeruleus in a more physiologically natural manner, allowing a more clinically applicable treatment than occurs by direct stimulation of locus coeruleus neurons.

SUMMARY OF THE INVENTION

The present invention includes a method of treating a disease or disorder of the nervous system in a subject, comprising the steps of administering an effective amount of a viral vector to the eye of the subject, wherein the viral vector comprises a promoter, a DREADD, and a 3' untranslated region encoded by the nucleotide sequence selected from the group consisting of SEQ ID NO:1, SEQ ID NO:2, SEQ ID NO:3, SEQ ID NO:4, SEQ ID NO:6, SEQ ID NO:7, SEQ ID NO:8, SEQ ID NO:9, SEQ ID NO:10, and SEQ ID NO:11; expressing the DREADD prior to administration of an agonist to the DREADD; and administering to the subject an agonist to the expressed DREADD.

In one embodiment, the viral vector may be an adeno-associated viral vector (AAV) selected from the group consisting of: AAV1, AAV2, AAV3, AAV4, AAV5, AAV6, AAV7, AAV8, AAV9, AAV10, AAV11, AAV12, and hybrids thereof.

In a second embodiment, the viral vector can be administered intraocularly, intravitreally, sub-retinally, through the sub-internal limiting membrane or by other means know in the art to the eye of the subject.

In another embodiment, the agonist may be clozapine N-oxide, DREADD agonist 21, salvinorin B, clozapine, olanzapine, or perlapine. The agonist may be administered systemically or to the eye.

In another embodiment, the disease or disorder of the nervous system to be treated may be a neuropsychiatric disorder or a neurodegenerative disease. The neuropsychiatric disorder to be treated may be depression, seasonal affective disorder, anxiety, sleep and circadian disorders including desynchronosis, stress disorders including Post Traumatic Stress Disorder (PTSD), Attention Deficit Hyperactivity Disorder (ADHD), autism, addiction, epilepsy, or Intensive Care Unit (ICU) psychosis. The neurodegenerative disease to be treated may be amyotrophic lateral sclerosis (ALS), Parkinson's disease, Alzheimer's disease, or Huntington's disease.

In another embodiment, the disease or disorder of the nervous system is a cerebrovascular accident (CVA) or stroke.

In another embodiment, the method of the present invention may additionally include administering at least one additional therapeutic agent for treatment of the neuropsychiatric disorder or the neurodegenerative disease.

In another embodiment, the at least one additional therapeutic agent for treatment of the neuropsychiatric disorder or the neurodegenerative disease is a neurological drug selected from the group consisting of acamprosate, agomelatine, alimemazine, alprazolam, amantadine, amfetamine, amisulpride, amitriptyline, amobarbital, amoxapine, apomorphine, apomorphine, aripiprazole, asenapine, atomoxetine, atropine, baclofen, benperidol, benztropine, biperiden, bromazepam, bromocriptine, bromperidol, brotizolam, buprenorphine, bupropion, buspirone, butobarbital, cabergoline, carbamazepine, chloral hydrate, chlordiazepoxide, chlorpheniramine, chlorpromazine, chlorprothixene, citalopram, clobazam, clomethiazole, clomipramine, clonazepam, clonidine, clorazepate, clozapine, cyclobarbital, cyproheptadine, cytisine, desipramine, desvenlafaxine, dexamfetamine, dexmethylphenidate, dextromethorphan, diazepam, dicyclomine dimenhydrinate, diphenhydramine, disulfiram, divalproex sodium, donepezil, doxacurium, doxepin, doxylamine, duloxetine, edaravone, enanthate, escitalopram, estazolam, eszopiclone, ethosuximide, flunitrazepam, fluoxetine, flupenthixol, fluphenazine, flurazepam, fluspirilen, fluvoxamine, gabapentin, galantamine, glutethimide, glycopyrrolate, guanfacine, haloperidol, hexamethonium, hydrochloride, hydroxyzine, iloperidone, imipramine, ipratropium, lamotrigine, levetiracetam, levodopa, levomepromazine, levomilnacipran, lisdexamfetamine, lisuride, lithium salts, loprazolam, lorazepam, lormetazepam, mecamylamine, melatonin, melperone, memantine, meprobamate, metamfetamine, methadone, methylphenidate, mianserin, midazolam, mirtazapine, moclobemide, modafinil, modecate, motherwort, nalmefene, naltrexone, niaprazine, nimetazepam, nitrazepam, nortriptyline, olanzapine, omca, ondansetron, orphenadrine, oxazepam, oxcarbazepine, oxitropium, oxybutynin, paliperidone, paroxetine, penfluridol, pentobarbital, perazine, pergolide, pericyazine, perphenazine, phenazepam, phenelzine pheno-barbital, phenytoin, pimozide, piribedil, pramipexole, pre-gabalin, prolixin decanoate, promethazine, propantheline bromide, prothipendyl, protriptyline, quazepam, quetiapine, ramelteon, rasagiline, reboxetine, remacemide, reserpine, riluzole, risperidone, rivastigmine, ropinirole, rotigotine, rubidium chloride, safinamide, scopolamine, secobarbital, sediten, selecten, selegiline, selegiline, sertindole, sertraline, sertraline, sevinol, sinqualone enantat, siqualone, sirtal, sodium oxybate, sodium valproate, solifenacin, stazepine, stelazine, sulpiride, suvorexant, tacrine, tegretol, telesmin, temazepam, terfluzine, tetrabenazine, thioridazine, thiothix-ene, tianeptine, timonil, tiotropium, tizanidine, tofisopam, tolcapone, tolterodine, topiramate, trancin, tranylcypromine, trazodone, triazolam, trifluoperaz, trifluoperazine, triftazin, trihexyphenidyl, trimipramine, tropicamide, tubocurarine, valerian, valproate, valproic acid, varenicline, venlafaxine, vilazodone, vortioxetine, zaleplon, ziprasidone, zolpidem, zopiclone, zotepine, zuclopenthixol, and combinations thereof.

The present invention also includes an isolated nucleic acid promoter comprising SEQ ID NO:5, a fragment of SEQ ID NO:5, or a variant of SEQ ID NO: 5 having at least about 75% identity to SEQ ID NO: 5, that retains promoter activity in retinal cells.

The present invention also includes the use of a viral vector comprising a promoter, a DREADD, and a 3' untrans-lated region encoded by the nucleotide sequences SEQ ID NO:1, SEQ ID NO:2, SEQ ID NO:3, SEQ ID NO:4, SEQ ID NO:6, SEQ ID NO:7, SEQ ID NO:8, SEQ ID NO:9, SEQ ID NO:10, or SEQ ID NO:11 for the treatment of a a disease or disorder of the nervous system in a subject.

In one embodiment, the disease or disorder of the nervous system to be treated by the use of the viral vector may be a neuropsychiatric disorder or a neurodegenerative disease. The neuropsychiatric disorder to be treated may be depres-sion, seasonal affective disorder, anxiety, sleep and circadian disorders including desynchronosis, stress disorders includ-ing Post Traumatic Stress Disorder (PTSD), Attention Defi-cit Hyperactivity Disorder (ADHD), autism, addiction, epi-lepsy, or Intensive Care Unit (ICU) psychosis.

In a second embodiment, the neurodegenerative disease to be treated by the use of the viral vector may be amyotrophic lateral sclerosis (ALS), Parkinson's disease, Alzheimer's disease, or Huntington's disease.

In another embodiment, the disease or disorder of the nervous system to be treated by the use of the viral vector is a cerebrovascular accident (CVA) or stroke.

The present invention also includes a kit comprising a viral vector, wherein the viral vector comprises a promoter, a DREADD, and a 3' untranslated region encoded by the nucleotide sequence selected from the group consisting of SEQ ID NO:1, SEQ ID NO:2, SEQ ID NO:3, SEQ ID NO:4, SEQ ID NO:6, SEQ ID NO:7, SEQ ID NO:8, SEQ ID NO:9, SEQ ID NO:10, and SEQ ID NO:11; and includes an agonist to the DREADD.

BRIEF DESCRIPTIONS OF THE DRAWINGS

FIG. 1 provides a graph of the average weight change of rats expressing an excitatory DREADD (G(q)) or GFP (control) in the retina after the indicated number of days in darkness (n=7). An * indicates p<0.05.

Figures 2A, 2B, 2C, 2D:
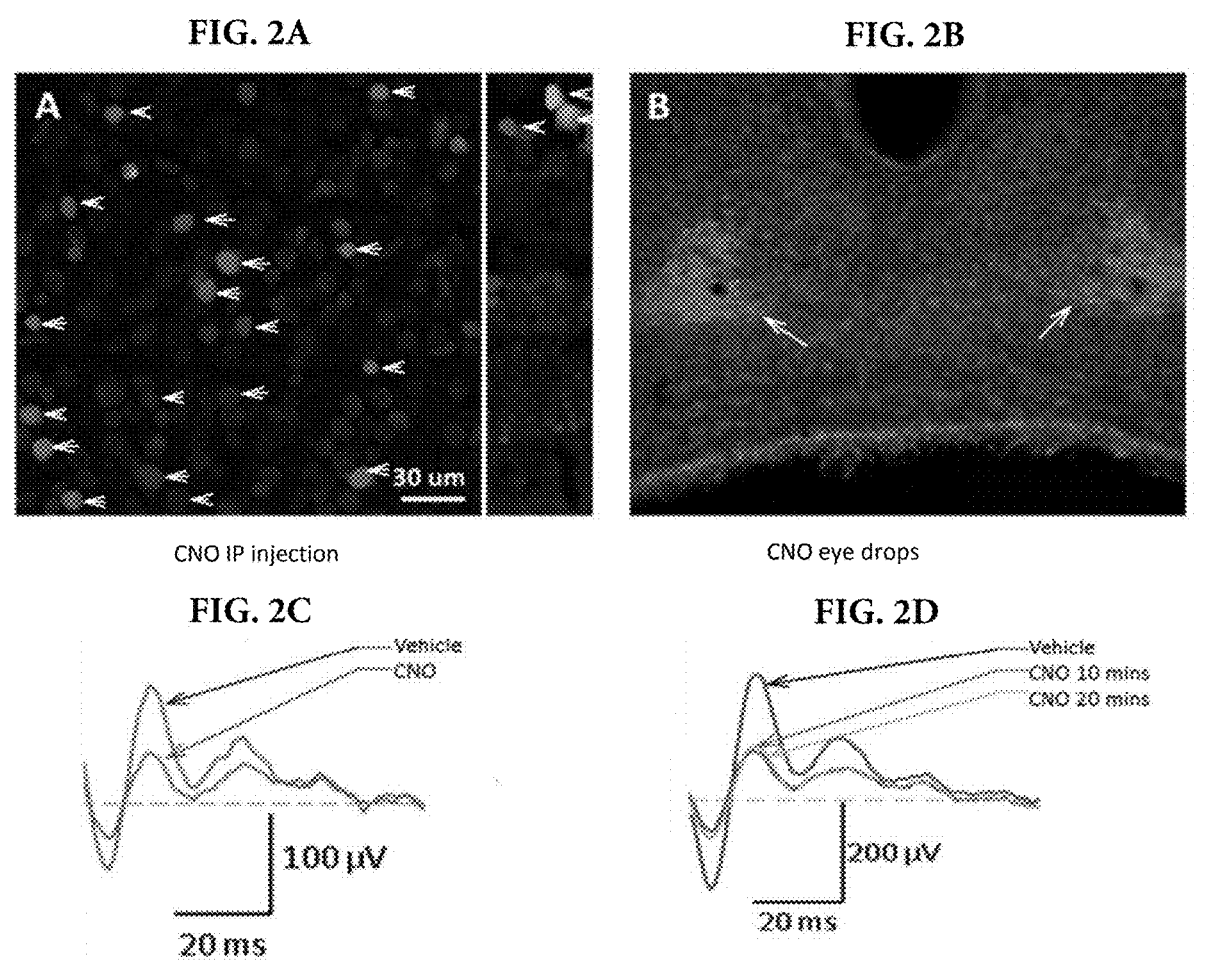

FIGS. 2A-D show DREADD expression and function in retinal cells via intravitreal injection (IVI). FIG. 2A shows expression of DREADD (arrows) in flat mounted retina. FIG. 2B shows expression of DREADD-terminal transport in suprachiasmatic nucleus (arrows). FIG. 2C shows CNO administered by intraperitoneal injection (i.p) reduced the size of the amplitude of the electroretinogram (ERG) in animals expressing the inhibitory hM4Di DREADD in retina. FIG. 2D shows CNO administered by CNO-contain-ing eye drops similarly decreased the amplitude of the electroretinogram (ERG).

Figures 3C, 3D:
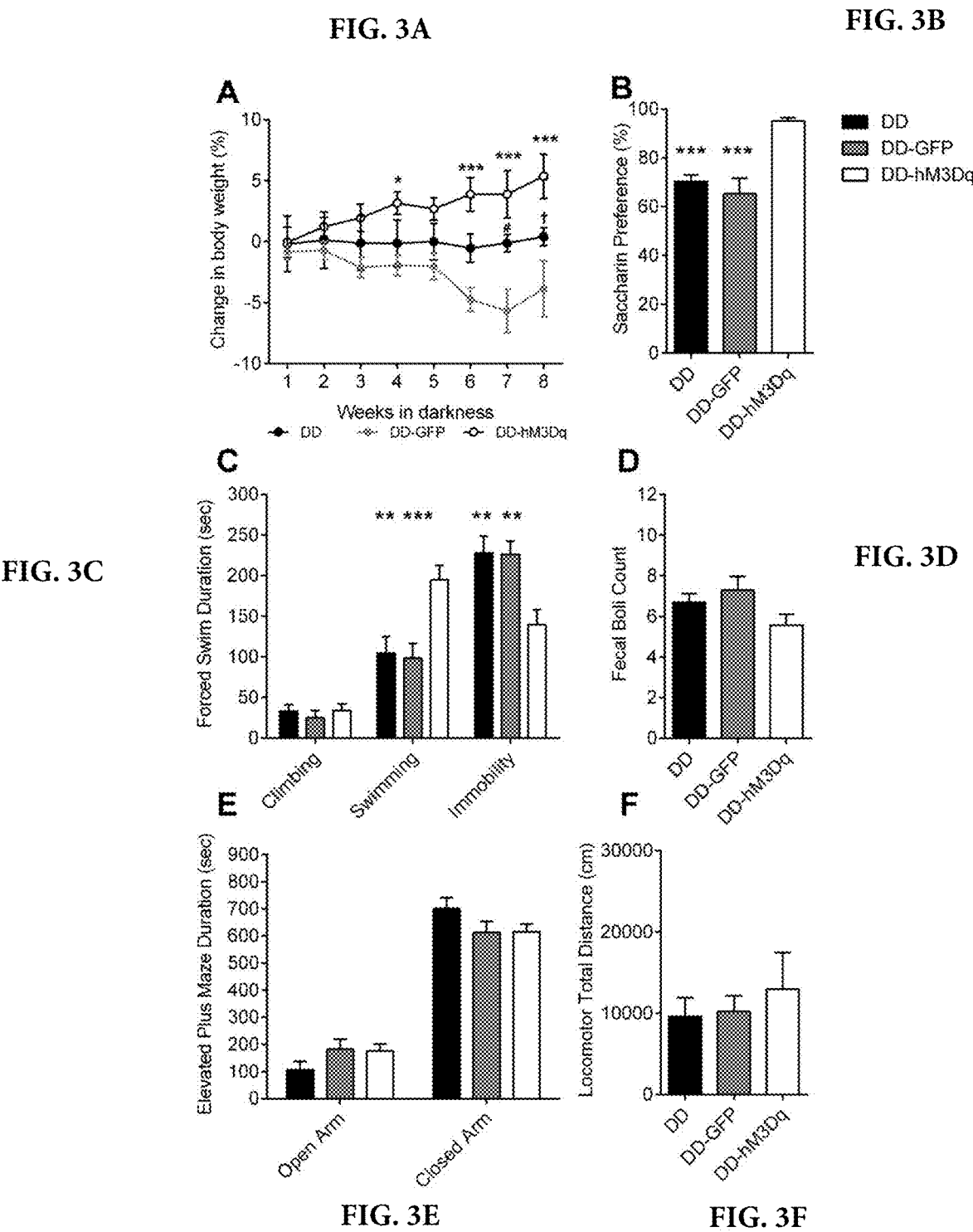

FIGS. 3A-F show DREADD receptor-mediated activation of retinal cells preventing the development of light depri-vation-induced depression-like behavior. FIG. 3A shows hM3Dq-hSyn activation prevents the relative weight loss that was induced by constant dark (DD) lighting conditions. FIG. 3B shows DREADD receptor-mediated activation of retinal cells leads to a reduction in an hedonic-like behavior, as measured by the saccharin preference test. FIG. 3C shows a reduction of depression-like behavior as measured by the forced swim test (FST) (C). FIG. 3D shows DD-hM3Dq-hSyn activation did not affect behavior typically interpreted as anxiety-like. There is no effect with respect to fecal boli count during the forced swim test. FIG. 3E shows no effect with respect to behaviors measured during the elevated plus maze (EPM) assay. FIG. 3F shows no effect with respect to locomotor activity. Abbreviations: chronic dark rearing (DD); chronic dark rearing with a control virus expressed in retinal cells (DD-GFP); DREADD receptor-mediated acti-vation of retinal cells during chronic darkness (DD-hM3Dq).

FIGS. 4A-E show that DREADD-mediated activation of retinal cells in constant darkness prevents apoptosis in locus coeruleus. FIG. 4A shows that chronic dark rearing (DD-Control) leads to apoptosis in locus coeruleus. FIG. 4B shows chronic dark rearing with a control virus expressed in retinal cells (DD-GFP) leads to apoptosis in locus coeruleus. Apoptosis is measured using the in situ marker of apoptosis recognizing the p85 fragment of PARP (arrows in FIG. 4A and FIG. 4B) within the locus coeruleus (shaded, gray). FIG. 4C shows that using an hSyn promoter, DREADD receptor-mediated activation of retinal cells during chronic darkness (DD-hM3Dq) prevents apoptosis in locus coeruleus to a level similar to control animals raised in standard dark/light conditions (DL-Control—FIG. 4D). There is arbitrary fluo-rescence intensity measured using the in situ marker of apoptosis recognizing the p85 fragment of PARP within the locus coeruleus boundary (arrows in FIG. 4D). FIG. 4E shows a comparison of the fluorescence intensity measure-ments of DD-Control, DD-GFP, DD-hM3Dq and DL-Con-trol.

Figures 5A, 5B, 5C:
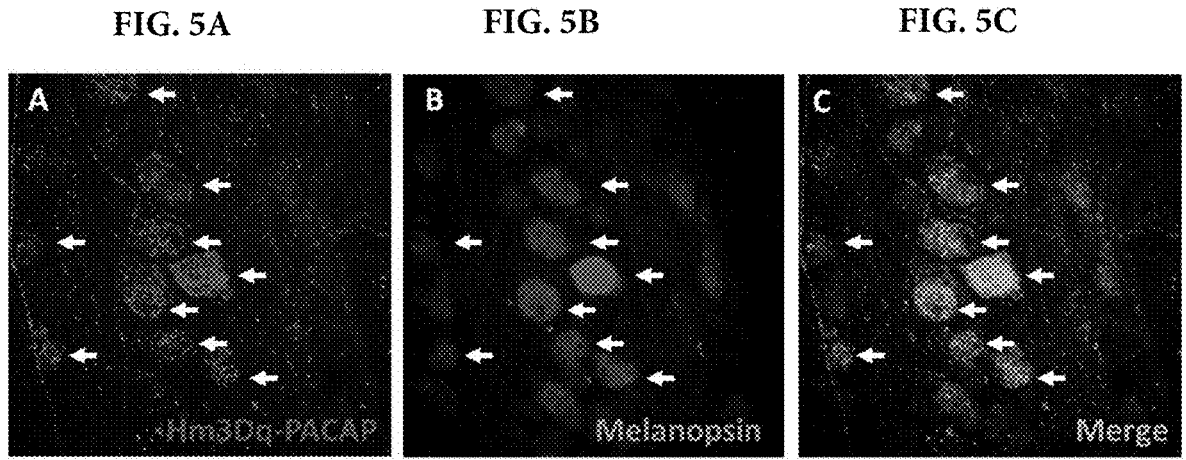

FIGS. 5A-C show PACAP promoter-driven DREADD expression in melanopsin (+) cells following intravitreal injection (IVI). Retinae were double stained by fluorescence immunohistochemistry for mCherry (the fluorescent tag fused to the hM3Dq gene in the Hm3Dq-PACAP construct) and melanopsin. FIG. 5A is the image of Hm3Dq-PACAP expressed in retinal cells. FIG. 5B is the image of melan-opsin expressed in retinal cells. The images of FIGS. 5A and 5B were co-localized to provide the image of FIG. 5C where cells that are overlapping indicate co-expression of hM3Dq and melanopsin. Arrows show PACAP-hM3Dq positive cells immunoreactive for melanopsin.

Figure 6:
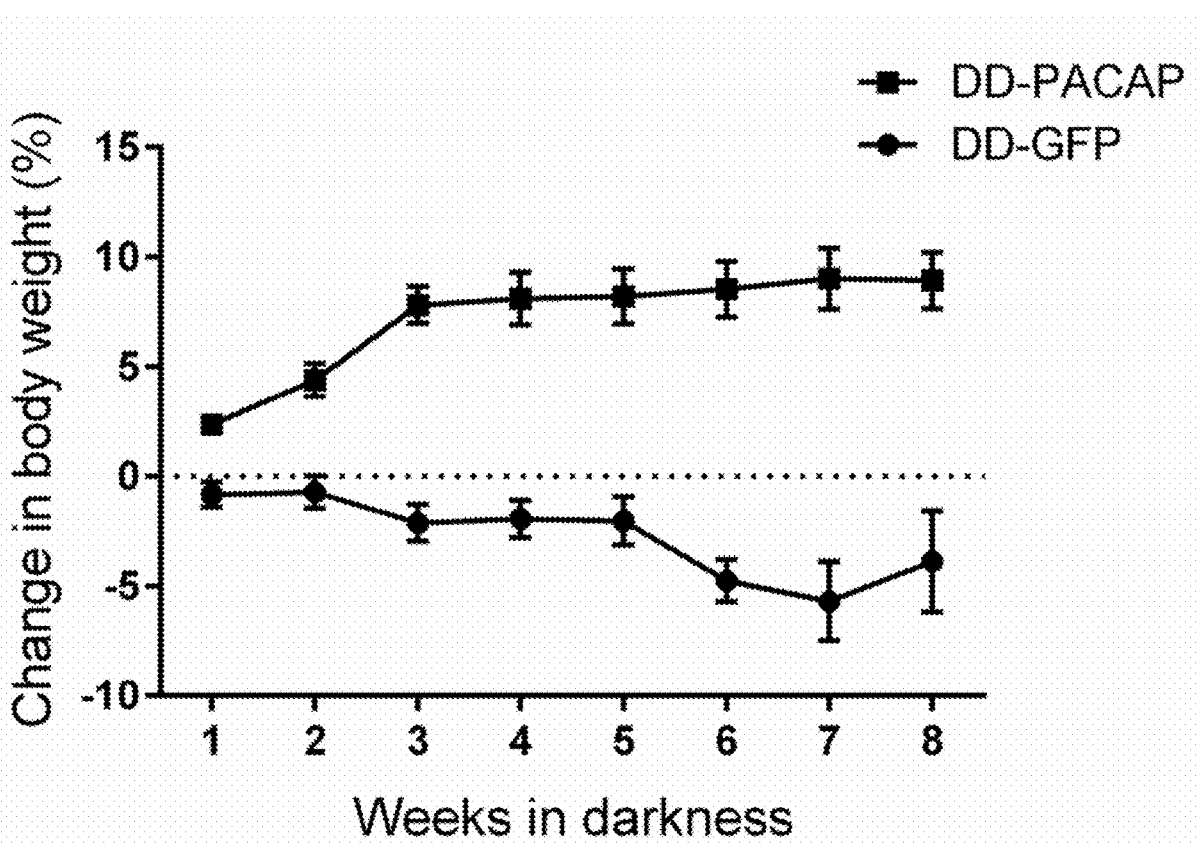

FIG. 6 shows DREADD activation of PACAP cells driven by a PACAP-specific promoter prevents depression-associ-ated weight loss. Abbreviations: chronic dark rearing with a control virus expressed in retinal cells (DD-GFP); DREADD receptor-mediated activation of PACAP cells driven by the specific PACAP promoter during chronic darkness (DD-PACAP).

DETAILED DESCRIPTION OF THE INVENTION

Definitions

So that the invention may be more readily understood, certain technical and scientific terms are specifically defined below. Unless specifically defined elsewhere in this document, all other technical and scientific terms used have the meaning commonly understood by one of ordinary skill in the art to which this invention belongs.

"Activation," "stimulation," and "treatment," as it applies to cells or to receptors, may have the same meaning, e.g., activation, stimulation, or treatment of a cell or receptor with a ligand, unless indicated otherwise by the context or explicitly.

"Ligand" encompasses natural and synthetic ligands, e.g., cytokines, cytokine variants, analogues, muteins, and binding compounds derived from antibodies. "Ligand" also encompasses small molecules, e.g., peptide mimetics of cytokines and peptide mimetics of antibodies. "Activation" can refer to cell activation as regulated by internal mechanisms as well as by external or environmental factors. "Response," e.g., of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming.

"Activity" of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton.

"Administration" and "treatment," as it applies to a human, veterinary, or research subject, refers to therapeutic treatment, prophylactic or preventative measures, to research and diagnostic applications. "Treatment" as it applies to a human, veterinary, or research subject, or cell, tissue, or organ, may encompass the transfection of any of the targeted AAV viral vectors, delivery of promoter-DREADD constructs, or the similar compositions described which are applied to a human or animal subject, a cell, tissue, physiological compartment, or physiological fluid.

"Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell.

"Administration" and "treatment" may also mean in vitro and ex vivo treatments, e.g., of a cell, by a reagent, diagnostic, binding compound, or by another cell.

"Treat" or "treating" refers to administering a therapeutic agent, such as a composition containing any of the AAV viral vectors, delivery of a promoter-DREADD construct, or similar compositions described, internally or externally to a subject or patient having one or more nervous system disease or disorder symptoms, or being suspected of having a nervous system disease or disorder or being at elevated risk of acquiring a nervous system disease or disorder, or for one or more of another disorder described, i.e., neurodegenerative disorder, for which the agent has therapeutic activity.

The term "prevent" refers to the prophylactic treatment of a subject who is at risk of developing a condition, e.g., a nervous system disease or disorder, resulting in a decrease in the probability that the subject will develop the condition.

The terms "subject" and "patient" are used interchangeably herein. The terms "subject" and "subjects" refer to an animal, such as a mammal including a non-primate (e.g. a cow, pig, horse, cat, dog, rat, and mouse) and a primate (e.g. a monkey such as a cynomolgous monkey, a chimpanzee and a human), and for example, a human.

Typically, the agent is administered in an amount effective to alleviate one or more nervous system disease or disorder symptoms in the treated subject or population, whether by inducing the regression of or inhibiting the progression of such symptom(s) by any clinically measurable degree. The amount of a therapeutic agent that is effective to alleviate any particular nervous system disease or disorder symptom (also referred to as the "therapeutically effective amount") may vary according to factors such as the disease state, age, and weight of the patient, and the ability of the drug to elicit a desired response in the subject Whether a nervous system disease or disorder symptom has been alleviated can be assessed by any clinical measurement typically used by physicians or other skilled healthcare providers to assess the severity or progression status of that symptom. While an embodiment of the present invention (e.g., a treatment method or article of manufacture) may not be effective in alleviating the target nervous system disease or disorder symptom(s) in every subject, it should alleviate the target nervous system disease or disorder symptom(s) in a statistically significant number of subjects as determined by any statistical test known in the art such as the Student's t-test, the chi$^2$-test, the U-test according to Mann and Whitney, the Kruskal-Wallis test (H-test), Jonckheere-Terpstra-test and the Wilcoxon-test.

"Isolated nucleic acid molecule" means DNA or RNA of genomic, mRNA, cDNA, or synthetic origin or some combination thereof, which is not associated with all or a portion of a polynucleotide in which the isolated polynucleotide is found in nature.

For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or up to twenty or more other proteins or portions or fragments thereof, or may include operably linked regulatory sequences that control expression of the coding region of the recited nucleic acid sequences, and/or may include vector sequences.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid is "operably linked" when it is placed into a functional relationship with another nucleic acid sequence. For example, DNA for a pre-sequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used, the terms "recombinant cell" refers to a cell into which an exogenous DNA segment, such as DNA segment that leads to the transcription of a biologically-active polypeptide or production of a biologically active nucleic acid such as an mRNA, has been introduced.

The term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter.

A "promoter" refers to a DNA sequence recognized by the synthetic machinery of the cell, or introduced synthetic machinery, required to initiate the specific transcription of a gene. The phrases "operatively positioned," "operatively linked," "under control," or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or inhibitory RNA (e.g., shRNA, miRNA) from a transcribed gene.

The term "agonist" refers to an agent, e.g., ligand, protein, polypeptide, peptide, lipid, antibody, antibody fragment, large molecule, or small molecule that binds to a receptor and has an intrinsic effect such as inducing a receptor-mediated response. For example, the agonist may stimulate, increase, activate, facilitate, enhance, or up regulate the activity of the receptor. In a particular embodiment, the agonist is a ligand.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimerosal, benzyl alcohol), anti-oxidant (e.g., ascorbic acid, sodium metabisulfite), solubilizer (e.g., polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions may be employed as carriers, particularly for injectable solutions. Suitable pharmaceutical carriers are described in "Remington's Pharmaceutical Sciences" by E. W. Martin (Mack Publishing Co., Easton, PA); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

A "therapeutically effective amount" of a compound or a pharmaceutical composition refers to an amount effective to prevent, inhibit, or treat a particular disorder or disease and/or the symptoms thereof. For example, "therapeutically effective amount" may refer to an amount sufficient to modulate the nervous system disease or disorder in a subject.

Nucleic Acids

The present invention also comprises certain constructs and nucleic acids encoding DREADD sequences. These constructs and sequences include promoter-DREADD sequences, i.e., PACAP-hM3D(Gq)-mCherry (SEQ ID: 1), TAC-1-hM4D(Gi)-mCherry (SEQ ID NO:2), PRSx8-HA-hM3D(Gq) (SEQ ID NO:3), PRSx8-HA-hM4D(Gi) (SEQ ID NO:4), PACAP-hM3D(Gq) (SEQ ID NO:6), PRSx8-hM3D(Gq) (SEQ ID NO:7), PRSx8-hM4D(Gi) (SEQ ID NO:8), TAC-1-hM4D(Gi) (SEQ ID NO:9), TAC-1-hM3D (Gq)-mCherry (SEQ ID NO:10) and PACAP-hM4D(Gi)-mCherry (SEQ ID NO:11), which can be useful in certain embodiments.

In some embodiments, constructs and nucleic acids encoding DREADD sequences comprise fluorophores, e.g., mCherry in SEQ ID NO:1. The expression of a DREADD can be successfully detected if it is tagged with a fluorescent marker, e.g., GFP, tdTomato, or mCherry.

Included also is an isolated nucleic acid promoter comprising SEQ ID NO:5, a fragment of SEQ ID NO:5, or a variant of SEQ ID NO: 5 having at least about 75% identity to SEQ ID NO: 5, that retains promoter activity in retinal cells. This promoter is designated the PACAP (pituitary adenylate cyclase activating polypeptide) promoter.

Table 1 provides the nucleotide sequences of the promoter-DREADD constructs and the PACAP promoter.

TABLE 1

| SEQ ID NO: | Construct Name | Nucleotide Sequence | | | | | |
|---|---|---|---|---|---|---|---|
| SEQ ID NO: 1 | PACAP-hM3D(Gq)-mCherry Construct | caatcttaaa | ttttcaatta | ttgcagaaaa | cacagtgaca | tggtttcaat | ttttaaaact |
| | | agtaagagcc | acggagagtg | tgaaagtgtg | tagacaggaa | aggtaaagat | ccatctgaat |
| | | actaggacta | actcagaaga | aaaagctttg | cactgaggca | gggattaagc | aggttctgag |
| | | cactgggaca | ttcgtggaca | cagaatccaa | gggaagatta | atatgaacag | cggggtgatt |
| | | tagacaatga | actcccacag | taagagcacc | actgccaaag | cttcaaattt | agaggctgtg |
| | | gtgaaaatta | aaccagtggc | aaatttcaac | atttgcagca | tctgcgccca | aatagttcag |
| | | caccaagagc | ctggacagca | ccacaggctc | tcatcctagt | ctcatccatc | aatctattca |
| | | gagacagact | gtcaacccag | ccagactcat | tagatattta | ctgaaaatcc | ttataattct |
| | | ttcctttaaa | acacaaaacg | acttccatgt | ttagtagcct | atttgaaaaa | gcatatgcaa |
| | | ggaattgaga | gatcaaaatt | aaaattatta | ataggagatc | ttgatggtgc | ttaaatctag |
| | | agatcagagt | tgtcattggt | gggggttgag | tgaaaattaa | gaaaaattag | ggactcaata |
| | | aaaacatgac | ttcaccattc | tctaaattct | acgagttctt | tacttgtctt | tgagaaatca |
| | | gtgaaatcga | aaaccatcaa | aataattgga | cttcttaaaa | attggattgt | gtgagtgaaa |

TABLE 1-continued

| SEQ ID NO: | Construct Name | Nucleotide Sequence |
|---|---|---|
| | | ggtgtttatc agaagcggat gactccggat cttatcatcc tggaggactg cacagaatag<br>ttaatatgtt ccttgaggga ctaggatgct gacgtctttt actgataccg gatcattacg<br>tgactggggg agaaaaaaaa ggaagtcata tcatgaataa aaatcggagt gcaacagtgc<br>aaccaaaata ttctgtactt gaaggcagaa agatgttgac aaagaggtgt ctcctgaaac<br>cacgttcgga cagcttattt tgttaactgc atatataaaa acgagcagaa ggccagtgtc<br>gacgccacca tgaccttgca caataacagt acaacctcgc ctttgtttcc aaacatcagc<br>tcctcctgga tacacagccc ctccgatgca gggctgcccc cgggaaccgt cactcatttc<br>ggcagctaca atgtttctcg agcagctggc aatttctcct ctccagacgt taccaccgat<br>gaccctctgg gaggtcatac cgtctggcaa gtggtcttca tcgctttctt aacgggcatc<br>ctggccttgg tgaccatcat cggcaacatc ctggtaattg tgtcatttaa ggtcaacaag<br>cagctgaaga cggtcaacaa ctacttcctc ttaagcctgg cctgtgccga tctgattatc<br>ggggtcattt caatgaatct gtttacgacc tacatcatca tgaatcgatg ggccttaggg<br>aacttggcct gtgacctctg gcttgccatt gactgcgtag ccagcaatgc ctctgttatg<br>aatcttctgt tcatcagctt tgacagatac ttttccatca cgaggccgct cacgtaccga<br>gccaaacgaa caacaaagag agccggtgtg atgatcggtc tggcttgggt catctccttt<br>gtcctttggg ctcctgccat cttgttctgg caatactttg ttggaaagag aactgtgcct<br>ccgggagagt gcttcattca gttcctcagt gagcccacca ttacttttgg cacagccatc<br>gctggttttt atatgcctgt caccattatg actattttat actggaggat ctataaggaa<br>actgaaaagc gtaccaaaga gcttgctggc ctgcaagcct ctgggacaga ggcagagaca<br>gaaaactttg tccaccccac gggcagttct cgaagctgca gcagttacga acttcaacag<br>caaagcatga aacgctccaa caggaggaag tatggccgct gccacttctg gttcacaacc<br>aagagctgga aacccagctc cgagcagatg gaccaagacc acagcagcag tgacagttgg<br>aacaacaatg atgctgctgc ctccctggag aactccgcct cctccgacga ggaggacatt<br>ggctccgaga cgagagccat ctactccatc gtgctcaagc ttccgggtca cagcaccatc<br>ctcaactcca ccaagttacc ctcatcggac aacctgcagg tgcctgagga ggagctgggg<br>atggtggact tggagaggaa agccgacaag ctgcaggccc agaagagcgt ggacgatgga<br>ggcagttttc caaaaagctt ctccaagctt cccatccagc tagagtcagc cgtggacaca<br>gctaagactt ctgacgtcaa ctcctcagtg ggtaagagca cggccactct acctctgtcc<br>ttcaaggaag ccactctggc caagaggttt gctctgaaga ccagaagtca gatcactaag<br>cggaaaagga tgtccctggt caaggagaag aaagcggccc agaccctcag tgcgatcttg<br>cttgccttca tcatcacttg gacccccatac aacatcatgg ttctggtgaa caccttttgt<br>gacagctgca tacccaaaac cttttggaat ctgggctact ggctgtgcta tatcaacagc<br>accgtgaacc ccgtgtgcta tgctctgtgc aacaaaacat tcagaaccac tttcaagatg<br>ctgctgctgt gccagtgtga caaaaaaaag aggcgcaagc agcagtacca gcagagacag<br>tcggtcattt ttcacaagcg cgcacccgag caggccttga aggatccccc ggtcgccacc<br>atggtgagca agggcgagga ggataacatg gccatcatca aggagttcat gcgcttcaag<br>gtgcacatgg agggctccgt gaacggccac gagttcgaga tcgagggcga gggcgagggc<br>cgcccctacg agggcaccca gaccgccaag ctgaaggtga ccaagggtgg cccctgccc<br>ttcgcctggg acatcctgtc ccctcagttc atgtacggct ccaaggccta cgtgaagcac<br>cccgccgaca tccccgacta cttgaagctg tccttccccg agggcttcaa gtgggagcgc<br>gtgatgaact cggaggacgg cggcgtggtg accgtgaccc aggactcctc cctgcaggac<br>ggcgagttca tctacaaggt gaagctgcgc ggcaccaact cccctccga cggccccgta<br>atgcagaaga agaccatggg ctgggaggcc tcctccgagc ggatgtaccc cgaggacggc<br>gccctgaagg gcgagatcaa gcagaggctg aagctgaagg acggcggcca ctacgacgct<br>gaggtcaaga ccacctacaa ggccaagaag cccgtgcagc tgcccggcgc ctacaacgtc<br>aacatcaagt tggacatcac ctcccacaac gaggactaca ccatcgtgga acagtacgaa<br>cgcgccgagg gccgccactc caccggcggc atggacgagc tgtacaagta agaattcgat<br>atcaagctta tcgataatca acctctggat tacaaaattt gtgaaagatt gactggtatt<br>cttaactatg ttgctccttt tacgctatgt ggatacgctg ctttaatgcc tttgtatcat<br>gctattgctt cccgtatggc tttcattttc tcctccttgt ataaatcctg gttgctgtct<br>ctttatgagg agttgtggcc cgttgtcagg caacgtggcg tggtgtgcac tgtgtttgct<br>gacgcaaccc ccactggttg gggcattgcc accacctgtc agctcctttc cgggactttc<br>gctttccccc tccctattgc cacggcggaa ctcatcgccg cctgccttgc ccgctgctgg<br>acaggggctc ggctgttggg cactgacaat tccgtggtgt tgtcggggaa atcatcgtcc<br>tttccttggc tgctcgccta tgttgccacc tggattctgc gcgggacgtc cttctgctac<br>gtcccttcgg ccctcaatcc agcggacctt ccttcccgcg gcctgctgcc ggctctgcgg<br>cctcttccgc gtcttcgcct tcgccctcag acgagtcgga tctccctttg ggccgcctcc<br>ccgcatcgat accgagcgct gctcgagaga tctacgggtg gcatccctgt gacccctccc<br>cagtgcctct cctggccctg gaagttgcca ctccagtgcc caccagcctt gtcctaataa<br>aattaagttg catcattttg tctgactagg tgtccttcta taatattatg gggtggaggg<br>gggtggtatg gagcaagggg caagttggga agacaacctg tagggcctgc ggggtctatt<br>gggaaccaag ctggagtgca gtggcacaat cttggctcac tgcaatctcc gcctcctggg<br>ttcaagcgat tctcctgcct cagcctcccg agttgttggg attccaggca tgcatgacca<br>ggctcagcta attttgttt tttggtaga cgggggttt caccatattg gccaggctgg<br>tctccaactc ctaatctcag gtgatctacc caccttggcc tcccaaattg ctgggattac<br>aggcgtgaac cactgctccc ttccctgtcc t |
| SEQ ID NO: 2 | TAC-1-hM4D(Gi)-mCherry construct | tgctgcagca attcaaagga gaatcttgct gttcgggcag aagaaattca atcaccttgt<br>ggagataatg aaaaagcttc atacttttaa tcagatattg atcgattacc ataatattct<br>cccatagcaa tagctgcagg cataagaaac ggaaagaatg gaagagattt ttaggagaat<br>acaaaaataa ataagtattt gagacttaga tactgccttt agtgacaagg gtgaggatcc<br>tacacactat gttgctggtt tcctagtctt cagcaagaaa gtgtaggaga gaagcaaaaa<br>acgtcctgtt caaccctgc tcctggatgt ggcaagaag aggagttacc cggcttgaaa<br>caaaagaaat cctaagtctg acacacaatg tcatgtttaa attcccttt ctccaaaatg<br>taaaataaat ctgcttccat cttctaaaat actatgggac taaacatcct tttgttatgc<br>taaggaaaag ccagtattcg cgttgattta gaagagggat gttctggtta tagaacgatg<br>ctgtgtctca gaaacactta aatactatta agctagaaat agaagggaaa ataatgcttc<br>cccgcatctc ccctcaagtg tagtcctctt tttttagcct gatttccgac gaaatgtctg |

TABLE 1-continued

| SEQ ID NO: | Construct Name | Nucleotide Sequence |
|---|---|---|
| | | aatgcctaca gttatttggc catcctgaaa agtgcaactt atcctgacgt ctcgagggac<br>ggaaaagtta ccgaagtcca aggaatgagt cactttgctc aaatttgatg agtaatatca<br>ggtgtcatga aacccagttt cgaaggagag gggaggggc gtcagatctg cagacggaag<br>caggccgctc cggattggat ggcgagacct cgatttcct aaaattgcgt catttagaac<br>ccaattgggt ccagatgtta tgggcatcga cgagttaccg tctcggaaac tctcaatcac<br>gcaagcgaaa ggagaggagg cggctaatta aatattgagc agaaagtcgc gtggggagaa<br>tgtcacgtgg gtctggaggc tcaaggaggc tgggataaat accgcaaggc actgagcagg<br>cgaaagagcg cgctcggacc tccttcccgg cggcagctac cgagagtgcg gagcgaccag<br>cgtgcgctcg gaggaaccag agaaactcag caccccgcgg gactgtccgt cgcagtaagt<br>gggtaccgtc gacgccacca tggccaactt cacacctgtc aatggcagct cgggcaatca<br>gtccgtgcgc ctggtcacgt catcatccca caatcgctat gagacggtgg aaatggtctt<br>cattgccaca gtgacaggct ccctgagcct ggtgactgtc gtgggcaaca tcctggtgat<br>gctgtccatc aaggtcaaca ggcagctgca gacagtcaac aactacttcc tcttcagcct<br>ggcgtgtgct gatctcatca taggcgcctt ctccatgaac ctctacaccg tgtacatcat<br>caagggctac tggcccctgg gcgccgtggt ctgcgacctg tggctggccc tggactgcgt<br>ggtgagcaac gcctccgtca tgaaccttct catcatcagc tttgaccgct acttctgcgt<br>caccaagcct ctcacctacc ctgcccggcg caccaccaag atggcaggcc tcatgattgc<br>tgctgcctgg gtactgtcct tcgtgctctg ggcgcctgcc atcttgttct ggcagtttgt<br>ggtgggtaag cggacggtgc ccgacaacca gtgcttcatc cagttcctgt ccaacccagc<br>agtgaccttt ggcacagcca ttgctggctt ctacctgcct gtggtcatca tgacggtgct<br>gtacatccac atctccctgg ccagtcgcag ccgagtccac aagcaccggc ccgagggccc<br>gaaggagaag aaagccaaga cgctggcctt cctcaagagc ccactaatga agcagagcgt<br>caagaagccc ccgccggggg aggccgcccg ggaggagctg cgcaatggca agctggagga<br>ggccccccg ccagcgctgc caccgccacc gcgccccgtg gctgataagg acacttccaa<br>tgagtccagc tcaggcagtg ccacccagaa caccaaggaa cgcccagcca cagagctgtc<br>caccacagag gccaccacgc ccgccatgcc cgcccctccc ctgcagcgc gggccctcaa<br>cccagcctcc agatggtcca agatccagat tgtgacgaag cagacaggca atgagtgtgt<br>gacagccatt gagattgtgc ctgccacgcc ggctggcatg cgccctgcgg ccaacgtggc<br>ccgcaagttc gccagcatcg ctcgcaacca ggtgcgcaag aagcggcaga tggcggcccg<br>ggagcgcaaa gtgacacgaa cgatctttgc cattctgctg gccttcatcc tcacctggac<br>gccctacaac gtcatggtcc tggtgaacac cttctgccag agctgcatcc ctgacacggt<br>gtggtccatt ggctactgc tctgctacgt caacagcacc atcaaccctg cctgctatgc<br>tctgtgcaac gccacctta aaaagacctt ccggcacctg ctgctgtgcc agtatcggaa<br>catcggcact gccaggcggg atccaccggt cgccaccatg gtgagcaagg gcgaggagga<br>taacatggcc atcatcaagg agttcatgcg cttcaaggtg cacatggagg gctccgtgaa<br>cggccacgag ttcgagatcg agggcgaggg cgagggccgc ccctacgagg gcacccagac<br>cgccaagctg aaggtgacca agggtggccc cctgcccttc gcctgggaca cctgtgtccc<br>tcagttcatg tacggctcca aggcctacgt gaagcacccc gccgacatcc ccgactactt<br>gaagctgtcc ttccccgagg gcttcaagtg ggagcgcgtg atgaacttcg aggacggcgg<br>cgtggtgacc gtgacccagg actcctccct gcaggacggc gagttcatct acaaggtgaa<br>gctgcgcggc accaacttcc cctccgacgg ccccgtaatg cagaagaaga ccatgggctg<br>ggaggcctcc tccgagcgga tgtaccccga ggacggcgcc ctgaagggcg agatcaagca<br>gaggctgaag ctgaaggacg gcggccacta cgacgctgag gtcaagacca cctacaaggc<br>caagaagccc gtgcagctgc ccggcgccta caacgtcaac atcaagttgg acatcacctc<br>ccacaacgag gactcacca tcgtggaaca gtacgaacgc gccgagggcc gccactccac<br>cggcggcatg gacgagctgt acaagtaaga attcgatatc cagcacagtg gcggccgctc<br>gagtctagag ggcccttcga aggtaagcct atccctaacc ctctcctcgg tctcgattct<br>acgcgtaccg gttaatcgat aatcaacctc tggattacaa aatttgtgaa agattgactg<br>gtattcttaa ctatgttgct ccttttacgc tatgtggata cgctgcttta atgcctttgt<br>atcatgctat tgcttccgt atggctttca ttttctcctc cttgtataaa tcctggttgc<br>tgtctcttta tgaggagttg tggcccgttg tcaggcaacg tggcgtggtg tgcactgtgt<br>ttgctgacgc aaccccccact ggttggggca ttgccaccac ctgtcagctc ctttccggga<br>ctttcgcttt ccccctccct attgccacg cggaactcat cgccgcctgc cttgcccgct<br>gctggacagg ggctcggctg ttgggcactg acaattccgt ggtgttgtcg gggaaatcat<br>cgtcctttcc ttggctgctc gcctgtgttg ccacctggat tctgcgcggg acgtccttct<br>gctacgtccc ttcggccctc aatccagcgg accttccttc ccgcggcctg ctgccggctc<br>tgcggcctct tccgcgtctt cgccttcgcc ctcagacgag tcggatctcc ctttgggccg<br>cctccccgca tcgaacccg ctgatcagc ggtcatcatc accatcacca ttgagtttaa<br>acccgctgat cagcctcgac tgtgccttct agttgccagc catctgttgt ttgcccctcc<br>cccgtgcctt ccttgaccct ggaaggtgcc actcccactg tccttcccta ataaaatgag<br>gaaattgcat cgcattgtct gagtaggtgt cattctattc tggggggtgg ggtggggcag<br>gacagcaagg gggaggattg ggaagacaat agcaggcatg ctggggatgc ggtgggctct<br>atgg |
| SEQ ID<br>NO: 3 | PRSx8-HA-<br>hM3D(Gq) construct | taaaaacgcg tataagcttc cgctagacaa atgtgattac cccgctagac caaatgtgat<br>tacccgcgct agacaaatgt gattaccccg ctagacaaat gtgattaccc cgctagac<br>aaatgtgatt accccgcta gacaaatgtg ttaccccgcg ctagacaaat gtgattaccc<br>cgctagcaa atgtgattac cccgaccag gcataaatg gccaggtggg accagagagc<br>tcacccccagc cgactctaga accggatcc atacgatgt tccagattac<br>gctatgacct tgcacaataa cagtacaacc tcgcctttgt ttccaaacat cagctcctcc<br>tggatacaca gcccctccga tgcagggctg ccccgggaa ccgtcactca tttcggcagc<br>tacaatgttt ctcgagcagc tggcaatttc tcctctccag acggtaccac cgatgaccct<br>ctggaggtc ataccgtctg gcaagtggtc ttcatcgct tcttaacgagg catcctggcc<br>ttggtgacca tcatcggcaa catcctggta attgtgtcat ttaaggtcaa caagcagctg<br>aagacggtca caactactt cctcttaagc ctggcctgtg ccgatctgat tatcgggtc<br>atttcaatga atctgtttac gacctacatc atcatgaatc gatgggccct agggaacttg<br>gcctgtgacc tctggcttgc cattgactgc gtagccagca tgcctctgt tatgaatctt<br>ctggtcatca gctttgacag atactttcc atcacgaggc cgctcacgta ccgagccaaa |

TABLE 1-continued

| SEQ ID NO: | Construct Name | Nucleotide Sequence |
|---|---|---|
| | | cgaacaacaa agagagccgg tgtgatgatc ggtctggctt gggtcatctc ctttgtcctt |
| | | tgggctcctg ccatcttgtt ctggcaatac tttgttggaa agagaactgt gcctccggga |
| | | gagtgcttca ttcagttcct cagtgagccc accattactt ttggcacagc catcgctggt |
| | | ttttatatgc ctgtcaccat tatgactatt ttatactgga ggatctataa ggaaactgaa |
| | | aagcgtacca aagagcttgc tggcctgcaa gcctctggga cagaggcaga gacagaaaac |
| | | tttgtccacc ccacgggcag ttctcgaagc tgcagcagtt acgaacttca acagcaaagc |
| | | atgaaacgct ccaacaggag gaagtatggc cgctgccact tctggttcac aaccaagagc |
| | | tggaaaccca gctccgagca gatggaccaa gaccacagca gcagtgacag ttggaacaac |
| | | aatgatgctg ctgcctccct ggagaactcc gcctcctccg acgaggagga cattggctcc |
| | | gagacgagag ccatctactc catcgtgctc aagcttccgg gtcacagcac catcctcaac |
| | | tccaccaagt taccctcatc ggacaacctg caggtgcctg aggaggagct ggggatggtg |
| | | gacttggaga ggaaagccga caagctgcag gcccagaaga gcgtggacga tggaggcagt |
| | | tttccaaaaa gcttctccaa gcttcccatc cagctagagt cagccgtgga cacagctaag |
| | | acttctgacg tcaactcctc agtgggtaag agcacggcca ctctacctct gtccttcaag |
| | | gaagccactc tggccaagag gtttgctctg aagaccagaa gtcagatcac taagcggaaa |
| | | aggatgtccc tggtcaagga gaagaaagcg gcccagaccc tcagtgcgat cttgcttgcc |
| | | ttcatcatca cttggacccc atacaacatc atggttctgg tgaacacctt ttgtgacagc |
| | | tgcataccca aaaccttttg gaatctgggc tactggctgt gctacatcaa cagcaccgtg |
| | | aaccccgtgt gctatgctct gtgcaacaaa acattcagaa ccactttcaa gatgctgctg |
| | | ctgtgccagt gtgacaaaaa aaagaggcgc aagcagcagt accagcagag acagtcggtc |
| | | attttcaca agcgcgcacc cgagcaggcc ttgtaggcgg ccgtacaagt aataggaatt |
| | | cacgcgtggt acctctagag tcgacccggg cggccgcttc gagcagacat gataagatac |
| | | attgatgagt ttggacaaac cacaactaga atgcagtgaa aaaaatgctt tatttgtgaa |
| | | atttgtgatg ctattgcttt atttgtaacc attataagct gcaataaaca agttaacaac |
| | | aacaattgca ttcattttat gtttcaggtt caggggagga tgtgggaggt tttttaaagc |
| | | aagtaaaacc tctacaaatg tggtaaaatc |
| SEQ ID NO: 4 | PRSx8-HA-hM4D(Gi) Construct | taaaaacgcg tataagcttc cgctagacaa atgtgattac ccccgctaga caaatgtgat |
| | | tacccgcgct agacaaatgt gattacccg ctagacaaat gtgattaccc cccgctagac |
| | | aaatgtgatt accccgcta gacaaatgtg attacccgcg ctagacaaat gtgattaccc |
| | | cgctagacaa atgtgattac ccccgaccag ggcataaatg gccaggtggg accagagagc |
| | | tcaccccagc cgactctaga accgggatcc accatgtacc catacgatgt tccagattac |
| | | gctatgtacc catacgatgt tccagattac gctgatgcca acttcacacc tgtcaatggc |
| | | agctcgggca atcagtccgt gcgcctggtc acgtcatcat cccacaatcg ctatgagacg |
| | | gtggaaatgg tcttcattgc cacagtgaca ggctccctga gcctggtgac tgtcgtgggc |
| | | aacatcctgg tgatgctgtc catcaaggtc aacaggcagc tgcagacagt caacaactac |
| | | ttcctcttca gcctggcgtg tgctgatctc atcataggcg ccttctccat gaacctctac |
| | | accgtgtaca tcatcaaggg ctactggccc ctgggcgccg tggtctgcga cctgtggctg |
| | | gccctggact gcgtggtgag caacgcctcc gtcatgaacc ttctcatcat cagctttgac |
| | | cgctacttct gcgtcaccaa gcctctcacc taccctgccc ggcgcaccac caagatggca |
| | | ggcctcatga ttgctgctgc ctgggtactg tccttcgtgc tctgggcgcc tgccatcttg |
| | | ttctggcagt tgttggtggg taagcggacg gtgcccgaca accagtgctt catccagttc |
| | | ctgtccaacc cagcagtgac cttttggcaca gccattgctg gcttctacct gcctgtggtc |
| | | atcatgacgg tgctgtacat ccacatctcc ctggccagtc gcagccgagt ccacaagcac |
| | | cggcccgagg gcccgaagga gaagaaagcc aagacgctgg ccttcctcaa gagcccacta |
| | | atgaagcaga gcgtcaagaa gccccgccc gggagggccg cccgggagga gctgcgcaat |
| | | ggcaagctgg aggaggcccc cccgccagcg ctgccaccgc caccgcgccc cgtggctgat |
| | | aaggacactt ccaatgagtc cagctcaggc agtgccaccc agaacaccaa ggaacgccca |
| | | gccacagagc tgtccaccac agaggccacc acgcccgcca tgcccgcccc tccctgcag |
| | | ccgcgggccc tcaacccagc ctccagatgg tccaagatcc agattgtgac gaagcagaca |
| | | ggcaatgagt gtgtgacagc cattgagatt gtgcctgcca cgccggctgg catgcgccct |
| | | gcggccaacg tggccgcaa gttcgccagc atcgctcgca accaggtgcg caagaagcgg |
| | | cagatggcgg cccgggagcg caaagtgaca cgaacgatct ttgccattct gctagccttc |
| | | atcctcaccc ggacgcccta caacgtcatg gtcctggtga acaccttctg ccagagctgc |
| | | atccctgaca cggtgtggtc cattggctac tggctctgct acgtcaacag caccatcaac |
| | | cctgcctgct atgctctgtg caacgccacc tttaaaaaga ccttccggca cctgctgctg |
| | | tgccagtatc ggaacatcgg cactgccagg taggaattcg tcgacccggg cggccgcttc |
| | | gagcagacat gataagatac attgatgagt ttggacaaac cacaactaga atgcagtgaa |
| | | aaaaatgctt tatttgtgaa atttgtgatg ctattgcttt atttgtaacc attataagct |
| | | gcaataaaca agttaacaac aacaattgca ttcattttat gtttcaggtt caggggagga |
| | | tgtgggaggt tttttaaagc aagtaaaacc tctacaaatg tggtaaaatc |
| SEQ ID NO: 5 | Pituitary Adenylate Cyclase Activating Polypeptide (PACAP) promoter | caatcttaaa ttttcaatta ttgcagaaaa cacagtgaca tggtttcaat tttttaaaact |
| | | agtaagagcc acgagagtg tgaaagtgtg tagacaggaa aggtaaagat ccatctgaat |
| | | actaggacta actcagaaga aaaagctttg cactgagcca gggattaagc aggttctgag |
| | | cactgggaca ttcgtggaca cagaatccaa gggaagatta atatgaacag cggggtgatt |
| | | tagacaatga actcccacag taagagcacc actgccaaag cttcaaattt agaggctgtg |
| | | gtgaaaatta aaccagtggc aaatttcaac atttgcagca tctgcgccca aatagttcag |
| | | caccaagagc ctggacagca ccacaggctc tcatcctagt ctcatccatc aatctattca |
| | | gagacagact gtcaacccag ccagactcat tagatattta ctgaaaatcc ttataattct |
| | | ttcctttaaa acacaaaacg acttccatgt ttagtagcct atttgaaaaa gcatatgcaa |
| | | ggaattgaga gatcaaaatt aaaattatta ataggagatc ttgatggtgc ttaaatctag |
| | | agatcagagt tgtcattggt gggggttgag tgaaaattaa gaaaaattag ggactcaata |
| | | aaaacatgac ttcaccattc tctaaattct acgagttctt tacttgtctt tgagaaatca |
| | | gtgaaatcga aaaccatcaa aataattgga cttcttaaaa attggattgt gtgagtgaaa |
| | | ggtgtttatc agaagcggat gactccggat cttatcatcc tggaggactg cacagaatag |
| | | ttaatatgtt ccttgaggga ctaggatgct gacgtctttt actgataccg gatcattacg |
| | | tgactggggg agaaaaaaaa ggaagtcata tcatgaataa aaatcggagt gcaacagtgc |

TABLE 1-continued

| SEQ ID NO: | Construct Name | Nucleotide Sequence |
| --- | --- | --- |
| | | aaccaaaata ttctgtactt gaaggcagaa agatgttgac aaagaggtgt ctcctgaaac cacgttcgga cagcttattt tgttaactgc atatataaaa acgagcagaa ggccagt |
| SEQ ID NO: 6 | PACAP-hM3D(Gq) Construct | caatcttaaa ttttcaatta ttgcagaaaa cacagtgaca tggtttcaat ttttaaaact agtaagagcc acggagagtg tgaaagtgtg tagacaggaa aggtaaagat ccatctgaat actaggacta actcagaaga aaaagctttg cactgaggca gggattaagc aggttctgag cactgggaca ttcgtggaca cagaatccaa gggaagatta atatgaacag cggggtgatt tagacaatga actcccacag taagagcacc actgccaaag cttcaaattt agaggctgtg gtgaaaatta aaccagtggc aaatttcaac atttgcagca tctgcgccca aatagttcag caccaagagc ctggacagca ccacaggctc tcatcctagt ctcatccatc aatctattca gagacagact gtcaacccag ccagactcat tagatattta ctgaaaatcc ttataattct ttcctttaaa acacaaaacg acttccatgt ttagtagcct atttgaaaaa gcatatgcaa ggaattgaga gatcaaaatt aaaattatta ataggagatc ttgatggtgc ttaaatctag agatcagagt tgtcattggt gggggttgag tgaaaattaa gaaaaattag ggactcaata aaaacatgac ttcaccattc tctaaattct acgagttctt tacttgtctt tgagaaatca gtgaaatcga aaaccatcaa aataattgga cttcttaaaa attggattgt gtgagtgaaa ggtgtttatc agaagcggat gactccggat cttatcatcc tggaggactg cacagaatag ttaatatgtt ccttgaggga ctaggatgct gacgtctttt actgataccg gatcattacg tgactggggg agaaaaaaaa ggaagtcata tcatgaataa aaatcggagt gcaacagtgc aaccaaaata ttctgtactt gaaggcagaa agatgttgac aaagaggtgt ctcctgaaac cacgttcgga cagcttattt tgttaactgc atatataaaa acgagcagaa ggccagtgtc gacgccacca tgaccttgca caataacagt acaacctcgc ctttgtttcc aaacatcagc tcctcctgga tacacagccc ctccgatgca gggctgcccc cgggaaccgt cactcatttc ggcagctaca atgtttctcg agcagctggc aatttctcct ctccagacgg taccaccgat gaccctctgg gaggtcatac cgtctggcaa gtggtcttca tcgctttctt aacgggcatc ctggccttgg tgaccatcat cggcaacatc ctggtaattg tgtcatttaa ggtcaacaag cagctgaaga cggtcaacaa ctacttcctc ttaagcctgg cctgtgccga tctgattatc ggggtcattt caatgaatct gtttacgacc tacatcatca tgaatcgatg ggccttaggg aacttggcct gtgacctctg gcttgccatt gactgcgtag ccagcaatgc ctctgttatg aatcttctgg tcatcagctt tgacagatac ttttccatca cgaggccgct cacgtaccga gccaaacgaa caacaaagag agccggtgtg atgatcggtc tggcttgggt catctccttt gtcctttggg ctcctgccat cttgttctgg caatactttg ttggaaagag aactgtgcct ccgggagagt gcttcattca gttcctcagt gagcccacca ttacttttgg cacagccatc gctggttttt atatgcctgt caccattatg actattttat actggaggat ctataaggaa actgaaaagc gtaccaaaga gcttgctggc ctgcaagcct ctgggacaga ggcagagaca gaaaactttg tccacccac gggcagttct cgaagctgca gcagttacga acttcaacag caaagcatga aacgctccaa caggaggaag tatggccgct gccacttctg gttcacaacc aagagctgga aacccagctc cgagcagatg gaccaagacc acagcagcag tgacagttgg aacaacaatg atgctgctgc ctccctggag aactccgcct cctccgacga ggaggacatt ggctccgaga cgagagccat ctactcccatc gtgctcaagc ttccgggtca cagcaccatc ctcaactcca ccaagttacc ctcatcggac aacctgcagg tgcctgagga ggagctgggg atggtggact tggagaggaa agccgacaag ctgcaggccc agaagagcgt ggacgatgga ggcagttttc caaaaagctt ctccaagctt cccatccagc tagagtcagc cgtggacaca gctaagactt ctgacgtcaa ctcctcagtg ggtaagagca cggccactct acctctgtcc ttcaaggaag ccactctggc caagaggttt gctctgaaga ccagaagtca gatcactaag cggaaaagga tgtccctggt caaggagaag aaagcggccc agaccctcag tgcgatcttg cttgccttca tcatcacttg gacccca tac aacatcatgg ttctggtgaa caccttttgt gacagctgca tacccaaaac ctttttggaat ctgggctact ggctgtgcta tatcaacagc accgtgaacc ccgtgtgcta tgctctgtgc aacaaaacat tcagaaccac tttcaagatg ctgctgctgt gccagtgtga caaaaaaaag aggcgcaagc agcagtacca gcagagacag tcggtcattt ttcacaagcg cgcacccgag caggccttga agaattcgat atcaagctta tcgataatca acctctggat tacaaaattt gtgaaagatt gactggtatt cttaactatg ttgctccttt tacgctatgt ggatacgctg ctttaatgcc tttgtatcat gctattgctt cccgtatggc tttcattttc tcctccttgt ataaatcctg gttgctgtct ctttatgagg agttgtggcc cgttgtcagg caacgtggcg tggtgtgcac tgtgtttgct gacgcaaccc ccactggttg gggcattgcc accacctgtc agctccttttc cgggactttc gctttccccc tccctattgc cacggcggaa ctcatcgccg cctgccttgc ccgctgctgg acaggggctc ggctgttggg cactgacaat ccgtggtgt gtcggggaa atcatcgtcc tttccttggc tgctcgccta tgttgccacc tggattctgc gcgggacgtc cttctgctac gtcccttcgg ccctcaatcc agcggacctt ccttcccgcg gcctgctgcc ggctctgcgg cctcttccgc gtcttcgcct tcgccctcag acgagtcgga tctcccttttg ggccgcctcc ccgcatcgat accgagcgct gctcgagaga tctacgggtg gcatccctgt gacccctccc cagtgcctct cctgccctg gaagttgcca ctccagtgcc caccagcctt gtcctaataa aattaagttg catcatttttg tctgactagg tgtccttcta taatattatg gggtggaggg gggtggtatg gagcaagggg caagttggga agacaacctg tagggcctgc ggggtctatt gggaaccaag ctggagtgca gtggcacaat cttggctcac tgcaatctcc gcctcctggg ttcaagcgat tctcctgcct cagcctcccg agttgttggg attccaggca tgcatgacca ggctcagcta atttttgttt tttggtaga acggggtttt caccatattg gccaggctgg tctccaactc ctaatctcag gtgatctacc caccttggcc tcccaaattg ctgggattac aggcgtgaac cactgctccc ttccctgtcct |
| SEQ ID NO: 7 | PRSx8-hM3D(Gq) construct | taaaaacgcg tataagcttc cgctagacaa atgtgattac ccccgctaga caaatgtgat taccgcgct agacaaatgt gattacccg ctagacaaat gtgattaccg aaatgtgatt accccgcta gacaaatgtg attaccgcg ctagacaaat gtgattaccg cgctagacaa atgtgattac ccccgaccag ggcataaatg gccaggtggg accagagagc tcaccccagc cgactctaga accgggatcc accatgatga ccttgcacaa taacagtaca acctcgcctt tgtttccaaa catcagctcc tcctggtaac acagccctc cgatgcaggg ctgcccccgg gaaccgtcac tcatttcggc agctacaatg tttctcgagc agctggcaat |

TABLE 1-continued

| SEQ ID NO: | Construct Name | Nucleotide Sequence |
|---|---|---|
| | | ttctcctctc cagacggtac caccgatgac cctctgggag gtcataccgt ctggcaagtg gtcttcatcg ctttcttaac gggcatcctg gccttggtga ccatcatcgg caacatcctg gtaattgtgt catttaaggt caacaagcag ctgaagacgg tcaacaacta cttcctctta agcctggcct gtgccgatct gattatcggg gtcatttcaa tgaatctgtt tacgacctac atcatcatga atcgatgggc cttagggaac ttggcctgtg acctctggct tgccattgac tgcgtagcca gcaatgcctc tgttatgaat cttctggtca tcagctttga cagatacttt tccatcacga ggccgctcac gtaccgagcc aaacgaacaa caaagagagc cggtgtgatg atcggtctgg cttgggtcat ctcctttgtc ctttgggctc ctgccatctt gttctggcaa tactttgttg gaaagagaac tgtgcctccg ggagagtgct tcattcagtt cctcagtgag cccaccatta cttttggcac agccatcgct ggttttttata tgcctgtcac cattatgact atttatatact ggaggatcta taaggaaact gaaaagcgta ccaaagagct tgctggcctg caagcctctg ggacagaggc agagacagaa aactttgtcc accccacggg cagttctcga agctgcagca gttacgaact tcaacagcaa agcatgaaac gctccaacag gaggaagtat ggccgctgcc acttctggtt cacaaccaag agctggaaac ccagctccga gcagatggac caagaccaca gcagcagtga cagttggaac aacaatgatg ctgctgcctc cctggagaac tccgcctcct ccgacgagga ggacattggc tccgagacga gagccatcta ctccatcgtg ctcaagcttc cgggtcacag caccatcctc aactccacca agttaccctc atcggacaac ctgcaggtgc ctgaggagga gctgggggatg gtggacttgg agaggaaagc cgacaagctg caggcccaga agagcgtgga cgatggaggc agttttccaa aaagcttctc caagcttccc atccagctag agtcagccgt ggacacagct aagacttctg acgtcaactc ctcagtgggt aagagcacgg ccactctacc tctgtccttc aaggaagcca ctctggccaa gagggtttgct ctgaagacca gaagtcagat cactaagcgg aaaaggatgt ccctggtcaa ggagaagaaa gcggcccaga ccctcagtgc gatcttgctt gccttcatca tcacttggac cccatacaac atcatggttc tggtgaacac cttttgtgac agctgcatac ccaaaacctt ttggaatctg ggctactggc tgtgctacat caacagcacc gtgaacccg tgtgctatgc tctgtgcaac aaaacattca gaaccacttt caagatgctg ctgctgtgcc agtgtgacaa aaaaaagagg cgcaagcagc agtaccagca gagacacgtg gtcattttc acaagcgcgc acccgagcag gccttgtagg cggccgtaca agtaataggga attcacgcgt ggtacctcta gagtcgaccc gggcggccgc ttcgagcaga catgataaga tacattgatg agtttggaca aaccacaact agaatgcagt gaaaaaaatg ctttatttgt gaaatttgtg atgctattgc tttatttgta accattataa gctgcaataa acaagttaac aacaacaatt gcattcattt tatgtttcag gttcaggggg agatgtggga ggttttttaa agcaagtaaa acctctacaa atgtggtaaaatc |
| SEQ ID NO: 8 | PRSx8-hM4D(Gi) Construct | aaaaacgcgt ataagcttcc gctagacaaa tgtgattacc cccgctagac aaatgtgatt acccgcgcta gacaaatgtg attaccccgc tagacaaatg tgattaccc ccgctagaca aatgtgatta cccccgctag acaaatgtga ttaccccgc tagacaaatg tgattacccc gctagacaaa tgtgattacc cccgaccagg gcataaatgg ccaggtggga ccagagagct cacccccagcc gactctagaa ccgggatcca ccatgatgta cccatacgat gttccagatt acgctgatgc caacttcaca cctgtcaatg gcagctcggg caatcagtcc gtgcgcctgg tcacgtcatc atcccacaat cgctatgaga cggtggaaat ggtcttcatt gccacagtga caggctccct gagcctggtg actgtcgtgg gcaacatcct ggtgatgctg tccatcaagg tcaacaggca gctgcagaca gtcaacaact acttcctctt cagcctggcg tgtgctgatc tcatcatagg cgccttctcc atgaacctct acaccgtgta catcatcaag ggctactggc ccctgggcgc cgtggtctgc gacctgtggc tggccctgga ctgcgtggtg agcaacgcct ccgtcatgaa ccttctcatc atcagctttg accgctactt ctgcgtcacc aagcctctca cctaccctgc ccggcgcacc accaagatgg caggcctcat gattgctgct gcctgggtac tgtccttcgt gctctgggcg cctgccatct tgttctggca gtttgtggtg ggtaagcgga cggtgcccga caaccagtgc ttcatccagt tcctgtccaa cccagcagtg accttttggca cagccattgc tggcttctac ctgcctgtgg tcatcatgac ggtgctgtac atccacatct ccctggccag tcgcagccga gtccacaagc accggcccga gggcccgaag gagaagaaag ccaagacgct ggccttcctc aagagcccac taatgaagca gagcgtcaag aagccccgc ccggggaggc cgcccgggag gagctgcgca atggcaagct ggaggaggcc ccccgccag cgctgccacc gccaccgcgc cccgtggctg ataaggacac ttccaatgag tccagctcag gcagtgccac ccagaacacc aaggaacgcc cagccacaga gctgtccacc acagaggcca ccacgccgc catgcccgcc cctcccctgc agccgcgggc cctcaacca gcctccagat ggtccaagat ccagattgtg acgaagcaga caggcaatga gtgtgtgaca gccattgaga ttgtgcctgc cacgccggct ggcatgcgca ctgcggccaa cgtggcccgc aagttcgcca gcatcgctcg caaccaggtg cgcaagaagc ggcagatggc ggcccgggag cgcaaagtga cacgaacgat cttttgccatt ctgctagcct tcatcctcac ctggacgccc tacaacgtca tggtcctggt gaacaccttc tgccagagct gcatccctga cacggtgtgg tccattggct actggctctg ctacgtcaac agcaccatca ccctgcctg ctatgctctg tgcaacgca cctttaaaaa gaccttccgg cacctgctgc tgtgccagta tcggaacatc ggcactgcca ggtaggaatt cgtcgacccg ggcggccgct cgagcagac atgataagat acattgatga gtttggacaa accacaacta gaatgcagtg aaaaaaatgc tttatttgtg aaatttgtga tgctattgct ttatttgtaa ccattataag ctgcaataaa caagttaaca acaacaattg cattcatttt atgtttcagg ttcaggggga gatgtgggag gttttttaaa gcaagtaaaa cctctacaaa tgtggtaaaa tc |
| SEQ ID NO: 9 | TAC-1-hM4D(Gi) Construct | tgctgcagca attcaaagga gaatcttgct gttcgggcag aagaaattca atcaccttgt ggagataatg aaaaagcttc atactttaa tcagatattg atcgattacc ataatattct cccatagcaa tagctgcagg cataagaaac ggaaagaatg gaagagattt ttaggagaat acaaaaataa ataagtattt gagacttaga tactgccttt agtgacaagg gtgaggatcc tacacactat gttgctggtt tcctagtctt cagcaagaaa gtgtaggaga gaagcaaaaa acgtcctgtt caaccctgc tcctggatgt gcaaggaag aggagttacc cggcttgaaa caaaagaaat cctaagtctg acacacaatg tcatgtttaa attccccttt ctccaaaatg taaaataaat ctgcttccat cttctaaaat actatgggac taaacatcct tttgttatgc taaggaaaag ccagtattcg cgttgattta gaagagggat gttctggtta tagaacgatg ctgtgtctca gaaacactta aatactatta agctagaaat agaagggaaa ataatgcttc |

TABLE 1-continued

| SEQ ID NO: | Construct Name | Nucleotide Sequence |
|---|---|---|
| | | cccgcatctc ccctcaagtg tagtcctctt ttttttagcct gatttccgac gaaatgtctg |
| | | aatgcctaca gttatttggc catcctgaaa agtgcaactt atcctgacgt ctcgagggac |
| | | ggaaaagtta ccgaagtcca aggaatgagt cactttgctc aaatttgatg agtaatatca |
| | | ggtgtcatga aacccagttt cgaaggagag gggaggggc gtcagatctg cagacggaag |
| | | caggccgctc cggattggat ggcgagacct cgattttcct aaaattgcgt catttagaac |
| | | ccaattgggt ccagatgtta tgggcatcga cgagttaccg tctcggaaac tctcaatcac |
| | | gcaagcgaaa ggagaggagg cggctaatta aatattgagc agaaagtcgc gtggggagaa |
| | | tgtcacgtgg gtctggaggc tcaaggaggc tgggataaat accgcaaggc actgagcagg |
| | | cgaaagagcg cgctcggacc tccttccggg cggcagctac cgagagtgcg gagcgaccag |
| | | cgtgcgctcg gaggaaccag agaaactcag caccccgcgg gactgtccgt cgcagtaagt |
| | | gggtaccgtc gacgccacca tggccaactt cacacctgtc aatggcagct cgggcaatca |
| | | gtccgtgcgc ctggtcacgt catcatccca caatcgctat gagacggtgg aaatggtctt |
| | | cattgccaca gtgacaggct ccctgagcct ggtgactgtc gtgggcaaca tcctggtgat |
| | | gctgtccatc aaggtcaaca ggcagctgca gacagtcaac aactacttcc tcttcagcct |
| | | ggcgtgtgct gatctcatca taggcgcctt ctccatgaac ctctacaccg tgtacatcat |
| | | caagggctac tggcccctgg gcgccgtggt ctgcgacctg tggctggccc tggactgcgt |
| | | ggtgagcaac gcctccgtca tgaaccttct catcatcagc tttgaccgct acttctgcgt |
| | | caccaagcct ctcacctacc ctgcccggcg caccaccaag atggcaggcc tcatgattgc |
| | | tgctgcctgg gtactgtcct tcgtgctctg ggcgcctgcc atcttgttct ggcagtttgt |
| | | ggtgggtaag cggacggtgc ccgacaacca gtgcttcatc cagttcctgt ccaacccagc |
| | | agtgacctttt ggcacagcca ttgctggctt ctacctgcct gtggtcatca tgacggtgct |
| | | gtacatccac atctccctgg ccagtcgcag ccgagtccac aagcaccggc ccgagggccc |
| | | gaaggagaag aaagccaaga cgctggcctt cctcaagagc ccactaatga agcagagcgt |
| | | caagaagccc ccgcccgggg aggccgcccg ggaggagctg cgcaatggca agctggagga |
| | | ggccccccg ccagcgctgc caccgccacc gcgccccgtg gctgataagg acacttccaa |
| | | tgagtccagc tcaggcagtg ccacccagaa caccaaggaa cgcccagcca cagagctgtc |
| | | caccacagag gccaccacgc ccgccatgcc cgcccctcc ctgcagccgc gggccctcaa |
| | | cccagcctcc agatggtcca agatccagat tgtgacgaag cagacaggca atgagtgtgt |
| | | gacagccatt gagattgtgc ctgccacgcc ggctggcatg cgccctgcgg ccaacgtggc |
| | | ccgcaagttc gccagcatcg ctcgcaacca ggtgcgcaag aagcggcaga tggcggcccg |
| | | ggagcgcaaa gtgacacgaa cgatctttgc cattctgctg gccttcatcc tcacctggac |
| | | gccctacaac gtcatggtcc tggtgaacac cttctgccag agctgcatcc ctgacacggt |
| | | gtggtccatt ggctactggc tctgctacgt caacagcacc atcaaccctg cctgctatgc |
| | | tctgtgcaac gccacctttat aaaagacctt ccggcacctg ctgctgtgcc agtatcggaa |
| | | catcggcact gccaggcgga attcgatatc cagcacagtg gcggccgctc gagtctagag |
| | | ggcccttcga aggtaagcct atccctaacc ctctcctcgg tctcgattct acgcgtaccg |
| | | gttaatcgat aatcaacctc tggattacaa aatttgtgaa agattgactg gtattcttaa |
| | | ctatgttgct cctttttacgc tatgtggata cgctgcttta atgcctttgt atcatgctat |
| | | tgcttcccgt atggctttca ttttctcctc cttgtataaa tcctggttgc tgtctcttta |
| | | tgaggagttg tggcccgttg tcaggcaacg tggcgtggtg tgcactgtgt ttgctgacgc |
| | | aaccccccact ggttggggca ttgccaccac ctgtcagctc ctttccggga ctttcgcttt |
| | | ccccctccct attgccacgg cggaactcat cgccgcctgc cttgcccgct gctggacagg |
| | | ggctcggctg ttgggcactg acaattccgt ggtgttgtcg gggaaatcat cgtcctttcc |
| | | ttggctgctc gcctgtgttg ccacctggat tctgcgcggg acgtccttct gctacgtccc |
| | | ttcggccctc aatccagcgg accttccttc ccgcggcctg ctgccggctc tgcggcctct |
| | | tccgcgtctt cgccttcgcc ctcagacgag tcggatctcc ctttgggccg cctccccgca |
| | | tcgaaacccg ctgatcagcc ggtcatcatc accatcacca ttgagtttaa acccgctgat |
| | | cagcctcgac tgtgccttct agttgccagc catctgttgt ttgcccctcc ccgtgccttc |
| | | ccttgacccct ggaaggtgcc actcccactg tcctttccta ataaaatgag gaaattgcat |
| | | cgcattgtct gagtaggtgt cattctattc tggggggtgg ggtggggcag gacagcaagg |
| | | gggaggattg ggaagacaat agcaggcatg ctggggatgc ggtgggctct atgg |
| SEQ ID NO: 10 | TAC-1-hM3D(Gq)- mCherry Construct | tgctgcagca attcaaagga gaatcttgct gttcgggcag aagaaattca atcaccttgt |
| | | ggagataatg aaaaagcttc atacttttaa tcagatattg atcgattacc ataatattct |
| | | cccatagcaa tagctgcagg cataagaaac ggaaagaatg aagagatttt taggagaat |
| | | acaaaaataa ataagtattt gagacttaga tactgccttt agtgacaagg gtgaggatcc |
| | | tacacactat gttgctggtt tcctagtctt cagcaagaaa gtgtaggaga gaagcaaaaa |
| | | acgtcctgtt caacccctgc tcctggatgt ggcaaggaag aggagttacc cggcttgaaa |
| | | caaaagaaat cctaagtctg acacacaatg tcatgtttaa attcccctt ctccaaaatg |
| | | taaaataaat ctgcttccat cttctaaaat actatgggac taaacatcct tttgttatgc |
| | | taaggaaaag ccagtattcg cgttgatttta gaagagggat gttctggtta tagaacgatg |
| | | ctgtgtctca gaaacactta aatactatta agctagaaat agaagggaaa ataatgcttc |
| | | cccgcatctc ccctcaagtg tagtcctctt ttttttagcct gatttccgac gaaatgtctg |
| | | aatgcctaca gttatttggc catcctgaaa agtgcaactt atcctgacgt ctcgagggac |
| | | ggaaaagtta ccgaagtcca aggaatgagt cactttgctc aaatttgatg agtaatatca |
| | | ggtgtcatga aacccagttt cgaaggagag gggaggggc gtcagatctg cagacggaag |
| | | caggccgctc cggattggat ggcgagacct cgattttcct aaaattgcgt catttagaac |
| | | ccaattgggt ccagatgtta tgggcatcga cgagttaccg tctcggaaac tctcaatcac |
| | | gcaagcgaaa ggagaggagg cggctaatta aatattgagc agaaagtcgc gtggggagaa |
| | | tgtcacgtgg gtctggaggc tcaaggaggc tgggataaat accgcaaggc actgagcagg |
| | | cgaaagagcg cgctcggacc tccttccggg cggcagctac cgagagtgcg gagcgaccag |
| | | cgtgcgctcg gaggaaccag agaaactcag caccccgcgg gactgtccgt cgcagtaagt |
| | | gggtaccgtc gacgccacca tggccttgca caataacagt acaaccttgca ctttgtttcc |
| | | aaacatcagc tcctcctgga tacacagccc ctccgatgca gggctgcccc cgggaaccgt |
| | | cactcatttc ggcagctaca atgtttctcg agcagctggc aatttctcct ctccagacgg |
| | | taccaccgat gaccctctgg gaggtcatac cgtctggcaa gtggtcttca tcgctttctt |
| | | aacgggcatc ctggccttgg tgaccatcat cggcaacatc ctggtaattg tgtcatttaa |
| | | ggtcaacaag cagctgaaga cggtcaacaa ctacttcctc ttaagcctgg cctgtgccga |

TABLE 1-continued

| SEQ ID NO: | Construct Name | Nucleotide Sequence |
|---|---|---|
| | | tctgattatc ggggtcattt caatgaatct gtttacgacc tacatcatca tgaatcgatg |
| | | ggccttaggg aacttggcct gtgacctctg gcttgccatt gactgcgtag ccagcaatgc |
| | | ctctgttatg aatcttctgg tcatcagctt tgacagatac ttttccatca cgaggccgct |
| | | cacgtaccga gccaaacgaa caacaaagag agccggtgtg atgatcggtc tggcttgggt |
| | | catctccttt gtcctttggg ctcctgccat cttgttctgg caatactttg ttggaaagag |
| | | aactgtgcct ccgggagagt gcttcattca gttcctcagt gagcccacca ttacttttgg |
| | | cacagccatc gctggttttt atatgcctgt caccattatg actattttat actggaggat |
| | | ctataaggaa actgaaaagc gtaccaaaga gcttgctggc ctgcaagcct ctgggacaga |
| | | ggcagagaca gaaaactttg tccacccac gggcagttct cgaagctgca gcagttacga |
| | | acttcaacag caaagcatga aacgctccaa caggaggaag tatggccgct gccacttctg |
| | | gttcacaacc aagagctgga aacccagctc cgagcagatg gaccaagacc acagcagcag |
| | | tgacagttgg aacaacaatg atgctgctgc ctccctggag aactccgcct cctccgacga |
| | | ggaggacatt ggctccgaga cgagagccat ctactccatc gtgctcaagc ttccgggtca |
| | | cagcaccatc ctcaactcca ccaagttacc ctcatcggac aacctgcagg tgcctgagga |
| | | ggagctgggg atggtggact tggagaggaa agccgacaag ctgcaggccc agaagagcgt |
| | | ggacgatgga ggcagttttc caaaaagctt ctccaagctt cccatccagc tagagtcagc |
| | | cgtggacaca gctaagactt ctgacgtcaa ctcctcagtg ggtaagagca cggccactct |
| | | acctctgtcc ttcaaggaag ccactctggc caagaggttt gctctgaaga ccagaagtca |
| | | gatcactaag cggaaaagga tgtccctggt caaggagaag aaagcggccc agacctcag |
| | | tgcgatcttg cttgccttca tcatcacttg gacccatac aacatcatgg ttctggtgaa |
| | | caccttttgt gacagctgca tacccaaaac cttttggaat ctgggctact ggctgtgcta |
| | | catcaacagc accgtgaacc ccgtgtgcta tgctctgtgc aacaaaacat tcagaaccac |
| | | tttcaagatg ctgctgctgt gccagtgtga caaaaaaaag aggcgcaagc agcagtacca |
| | | gcagagacag tcggtcattt ttcacaagcg cgcacccgag caggccttga aggatccacc |
| | | ggtcgccacc atggtgagca aggcgagga ggataacatg gccatcatca aggagttcat |
| | | gcgcttcaag gtgcacatgg agggctccgt gaacggccac gagttcgaga tcgagggcga |
| | | gggcgagggc cgcccctacg agggcaccca gaccgccaag ctgaaggtga ccaagggtgg |
| | | ccccctgccc ttcgcctggg acatcctgtc ccctcagttc atgtacggct ccaaggccta |
| | | cgtgaagcac cccgccgaca tccccgacta cttgaagctg tccttccccg agggcttcaa |
| | | gtgggagcgc gtgatgaact cgaggacgcg cggcgtggtg accgtgaccc aggactcctc |
| | | cctgcaggac ggcgagttca tctacaaggt gaagctgcgc ggcaccaact cccctccga |
| | | cggccccgta atgcagaaga agaccatggg ctgggaggcc tcctccgagc ggatgtaccc |
| | | cgaggacggc gccctgaagg gcgagatcaa gcagaggctg aagctgaagg acggcggcca |
| | | ctacgacgct gaggtcaaga ccacctacaa ggccaagaag cccgtgcagc tgcccggcgc |
| | | ctacaacgtc aacatcaagt tggacatcac ctcccacaac gaggactaca ccatcgtgga |
| | | acagtacgaa cgcgccgagg gccgccactc caccggcggc atggacgagc tgtacaagta |
| | | agaattcgat atccagcaca gtggcggccg ctcgagtcta gagggccctt cgaaggtaag |
| | | cctatcccta accctctcct cggtctcgat tctacgcgta ccggttaatc gataatcaac |
| | | ctctggatta caaaatttgt gaaagattga ctggtattct taactatgtt gctcctttta |
| | | cgctatgtgg atacgctgct ttaatgcctt tgtatcatgc tattgcttcc cgtatggctt |
| | | tcattttctc ctccttgtat aaatcctggt tgctgtctct ttatgaggag ttgtggcccg |
| | | ttgtcaggca acgtggcgtg gtgtgcactg tgtttgctga cgcaacccc actggttggg |
| | | gcattgccac cacctgtcag ctcctttccg ggactttcgc tttccccctc cctattgcca |
| | | cggcggaact catcgccgcc tgccttgccc gctgctgaca aggggctcgg ctgttgggca |
| | | ctgacaattc cgtggtgttg tcggggaaat catcgtcctt ccttggctg ctcgcctgtg |
| | | ttgccacctg gattctgcgc gggacgtcct tctgctacgt cccttcggcc ctcaatccag |
| | | cggaccttcc ttcccgcggc ctgctgccgg ctctgcggcc tcttccgcgt cttcgccttc |
| | | gccctcagac gagtcggatc tccctttggg ccgcctcccc gcat |
| SEQ ID NO: 11 | PACAP-hM4D(Gi)-mCherry Construct | caatcttaaa ttttcaatta ttgcagaaaa cacagtgaca tggtttcaat ttttaaaact |
| | | agtaagagcc acggagagtg tgaaagtgtg tagacaggaa aggtaaagat ccatctgaat |
| | | actaggacta actcagaaga aaaagctttg cactgaggca gggattaagc aggttctgag |
| | | cactgggaca ttcgtggaca cagaatccaa gggaagatta atatgaacag cggggtgatt |
| | | tagacaatga actcccacag taagagcacc actgccaaag cttcaaattt agaggctgtg |
| | | gtgaaaatta aaccagtggc aaatttcaac atttgcagca tctgcgccca aatagttcag |
| | | caccaagagc ctggacagca ccacaggctc tcatcctagt ctcatccatc aatctattca |
| | | gagacagact gtcaacccag ccagatccat tagatattta ctgaaaatcc ttataattct |
| | | ttcctttaaa acacaaaacg acttccatgt ttagtagcct atttgaaaaa gcatatgcaa |
| | | ggaattgaga gatcaaaatt aaaattatta ataggagatc ttgatggtgc ttaaatctag |
| | | agatcagagt tgtcattggt gggggttgag tgaaaattaa gaaaaattag ggactcaata |
| | | aaaacatgac ttcaccattc tctaaattct acgagttctt tacttgtctt tgagaaatca |
| | | gtgaaatcga aaaccatcaa aataattgga cttcttaaaa attggattgt gtgagtgaaa |
| | | ggtgtttatc agaagcggat gactccggat cttatcatcc tggaggactg cacagaatag |
| | | ttaatatgtt ccttgaggga ctaggatgct gacgtctttt actgataccg gatcattacg |
| | | tgactggggg agaaaaaaaa ggaagtcata tcatgaataa aaatcggagt gcaacagtgc |
| | | aaccaaaata ttctgtactt gaaggcagaa agatgttgac aaaagaggtgt ctcctgaaac |
| | | cacgttcgga cagcttattt tgttaactgc atatataaaa acgagcagaa ggccagtgtc |
| | | gacgccacca tggccaactt cacacctgtc aatggcagct cgggcaatca gtccgtgcgc |
| | | ctggtcacgt catcatccca caatcgctat gagacggtgg aaatggtctt cattgccaca |
| | | gtgacaggct ccctgagcct ggtgactgtc gtgggcaaca tcctggtgat gctgtccatc |
| | | aaggtcaaca ggcagctgca gacagtcaac aactacttcc tcttcagcct ggcgtgtgct |
| | | gatctcatca taggcgcctt ctccatgaac ctctacaccg tgtacatcat caagggctac |
| | | tggcccctgg gcgccgtggt ctgcgacctg tggctggccc tggactacgt ggtgagcaac |
| | | gcctccgtca tgaaccttct catcatcagc tttgaccgct acttctgcgt caccaagcct |
| | | ctcacctacc ctgcccggcg caccaccaag atggcaggcc tcatgattgc tgctgcctgg |
| | | gtactgtcct tcgtgctctg ggcgcctgcc atcttgttct ggcagtttgt ggtgggtaag |
| | | cggacggtgc ccgacaacca gtgcttcatc cagttcctgt ccaacccagc agtgaccttt |
| | | ggcacagcca ttgctggctt ctacctgcct gtggtcatca tgacggtgct gtacatccac |

TABLE 1-continued

| SEQ ID NO: | Construct Name | Nucleotide Sequence |
|---|---|---| atctccctgg ccagtcgcag ccgagtccac aagcaccggc ccgagggccc gaaggagaag
aaagccaaga cgctggcctt cctcaagagc ccactaatga agcagagcgt caagaagccc
ccgcccgggg aggccgcccg ggaggagctg cgcaatggca agctggagga ggcccccccg
ccagcgctgc caccgccacc gcgcccgtg gctgataagg acacttccaa tgagtccagc
tcaggcagtg ccacccagaa caccaaggaa cgcccagcca cagagctgtc caccacagag
gccaccacgc ccgccatgcc cgcccctccc ctgcagccgc gggccctcaa cccagcctcc
agatggtcca agatccagat tgtgacgaag cagacaggca atgagtgtgt gacagccatt
gagattgtgc ctgccacgcc ggctggcatg cgccctgcgg ccaacgtggc ccgcaagttc
gccagcatcg ctcgcaacca ggtgcgcaag aagcggcaga tggcggcccg ggagcgcaaa
gtgacacgaa cgatctttgc cattctgctg gccttcatcc tcacctggac gccctacaac
gtcatggtcc tggtgaacac cttctgccag agctgcatcc ctgacacggt gtggtccatt
ggctactggc tctgctacgt caacagcacc atcaaccctg cctgctatgc tctgtgcaac
gccacctta aaaagacctt ccggcacctg ctgctgtgcc agtatcggaa catcggcact
gccaggcggg gatcccccgg tcgccaccat ggtgagcaag ggcgaggagg ataacatggc
catcatcaag gagttcatgc gcttcaaggt gcacatggag ggctccgtga acggccacga
gttcgagatc gagggcgagg gcgagggccg ccctacgag ggcacccaga ccgccaagct
gaaggtgacc aagggtggcc ccctgccctt cgcctgggac atcctgtccc ctcagttcat
gtacggctcc aaggcctacg tgaagcaccc cgccgacatc cccgactact tgaagctgtc
cttccccgag ggcttcaagt gggagcgcgt gatgaacttc gaggacggcg gcgtggtgac
cgtgacccag gactcctccc tgcaggacgg cgagttcatc tacaaggtga agctgcgcgg
caccaacttc cctccgacg gccccgtaat gcagaagaag accatgggct gggaggcctc
ctccgagcgg atgtacccc aggacggcgc cctgaagggc gagatcaagc agaggctgaa
gctgaaggac ggcggccact acgacgctga ggtcaagacc acctacaagg ccaagaagcc
cgtgcagctg cccggcgcct acaacgtcaa catcaagttg gacatcacct cccacaacga
ggactacacc atcgtggaac agtacgaacg cgccgagggc cgccactcca ccggcggcat
ggacgagctg tacaagtaag aattcgatat caagcttatc gataatcaac ctctggatta
caaaatttgt gaaagattga ctggtattct taactatgtt gctccttta cgctatgtgg
atacgctgct ttaatgcctt tgtatcatgc tattgcttcc cgtatggctt tcattttctc
ctccttgtat aaatcctggt tgctgtctct ttatgaggag ttgtggcccg ttgtcaggca
acgtggcgtg gtgtgcactg tgtttgctga cgcaacccc actggttggg gcattgccac
cacctgtcag ctcctttccg ggactttcgc tttccccctc cctattgcca cggcggaact
catcgccgcc tgccttgccc gctgctggac aggggctcgg ctgttgggca ctgacaattc
cgtggtgttg tcggggaaat catcgtcctt ccttggctg ctcgcctatg ttgccacctg
gattctgcgc gggacgtcct tctgctacgt cccttcggcc ctcaatccag cggaccttcc
ttcccgcggc ctgctgccgg ctctgcggcc tcttccgcgt cttcgccttc gccctcagac
gagtcggatc tccctttggg ccgcctcccc gcatcgatac cgagcgctgc tcgagagatc
tacgggtggc atccctgtga cccctcccca gtgcctctcc tggccctgga agttgccact
ccagtgccca ccagccttgt cctaataaaa ttaagttgca tcattttgtc tgactaggtg
tccttctata atattatggg gtggagggg gtggtatgga gcaagggca agttgggaag
acaacctgta gggcctgcgg ggtctattgg gaaccaagct ggagtgcagt ggcacaatct
tggctcactg caatctccgc ctcctgggtt caagcgattc tcctgcctca gcctcccgag
ttgttgggat tccaggcatg catgaccagg ctcagctaat ttttgttttt ttggtagaga
cggggtttca ccatattggc caggctggtc tccaactcct aatctcaggt gatctaccca
ccttggcctc ccaaattgct gggattacag gcgtgaacca ctgctccctt ccctgtcct Preferably, the nucleic acids hybridize under low, moderate or high stringency conditions. A first nucleic acid molecule is "hybridizable" to a second nucleic acid molecule when a single stranded form of the first nucleic acid molecule can anneal to the second nucleic acid molecule under the appropriate conditions of temperature and solution ionic strength (see Sambrook, et al., supra). The conditions of temperature and ionic strength determine the "stringency" of the hybridization. Typical low stringency hybridization conditions include 55° C., 5×SSC, 0.1% SDS and no formamide; or 30% formamide, 5×SSC, 0.5% SDS at 42° C. Typical moderate stringency hybridization conditions are 40% formamide, with 5x or 6×SSC and 0.1% SDS at 42° C. High stringency hybridization conditions are 50% formamide, 5× or 6×SSC at 42° C. or, optionally, at a higher temperature (e.g., 57° C., 59° C., 60° C., 62° C., 63° C., 65° C. or 68° C.). In general, SSC is 0.15M NaCl and 0.015M Na-citrate. Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook, et al., supra, 9.50-9.51). For hybridization with shorter nucleic acids, e.g., oligonucleotides, the position of mismatches becomes more important, and the length of the oligonucleotide determines its specificity (see Sambrook, et al., supra, 11.7-11.8).

Designer Receptors Exclusively Activated by Designer Drugs (DREADDs)

Methods and compositions for treating diseases and disorders of the nervous system are provided. The methods employ the use of the chemogenetic tools known as Designer Receptors Exclusively Activated by Designer Drugs (DREADDs), to selectively control brain pathways that are initiated by the retina. Neurosurgical problems associated with injecting DREADDs into the brain can be avoided by using the retina as a target for DREADD expression.

The suprachiasmatic nucleus (SCN) receives non-image forming visual signals from the retina. These signals are then transmitted to the dorsal medial hypothalamus (DMH), which relays circadian information to the locus coeruleus (LC), together forming a circuit for the circadian regulation of arousal. Disruption to this circuit leads to degeneration of LC neurons and cortical noradrenergic-LC fibers, which leads to mood disturbance and other neurological disorders, including but not limited to cognitive deficits, loss of consciousness, and sleep and circadian disorders.

The above pathway may be referred to as the Photic Regulation of Arousal and Mood (PRAM) pathway. Disrupting this pathway leads to depressive-like behavior in rats. Depression is associated with altered circadian activity, e.g., blunted amplitude and phase delay of circadian rhythms, increased core temperature, and phase advanced oscillations of noradrenaline and cortisol plasma concentrations. Depression is also associated with disrupted sleep as well as dysregulation of sleep, e.g., seasonal affective disorder and short-day length lighting schedules.

Retinal expression of DREADDs has been demonstrated following intravitreal injection (IVI). The expression of DREADDs has been shown in retinal ganglion cells (RGCs) and in fibers of RGCs in suprachiasmatic nucleus (SCN), the region of the brain which controls circadian rhythms and which also affects mood, attention and cognitive processing. The function of DREADD expression in the retina has also been confirmed using electroretinogram (ERG) following delivery of a DREADD agonist, clozapine N-oxide (CNO). CNO efficacy was compared when administered systemically versus by eye drops, which represents a more clinically useful administration technique. Significantly, application of CNO via eye drops is at least as successful at eliciting DREADD function as application of CNO via systemic delivery.

The present invention encompasses compositions and methods of inhibiting, activating, treating and/or preventing diseases and disorders of the nervous system in a subject, which involve the transfection of a class of receptors known as DREADDs. DREADDs are engineered G-protein coupled receptors which can be activated by otherwise inert drug-like small molecules. The technique has combined chemical and genetic approaches to achieve localized and temporally-specified decreases or increases (e.g., hM3Dq or hM4Di) in neuronal excitability by viral expression of the a particular DREADD. (Katzel et al. (2014) *Nat. Commun.*, 5:3847; Mahler et al. (2014) *Nat. Neurosci.*, 17:577-85; Pei et al. (2008) *Physiology* 23:313-21; Ferguson et al. (2011) *Nat. Neurosci.*, 14: 22-24; Fortress, A. M. et al. (2015) *J. Neurosci.*, 35(4), 1343-1353; Vazey, E. M., et al. (2014). *Proc. Natl. Acad. Sci.*, 111(10), 3859-3864; each of the foregoing references are incorporated by reference). In a particular embodiment, the methods comprise administering a nucleic acid molecule encoding a DREADD and administering an agonist of the DREADD to the subject.

For enhancing neuronal firing and activating Gq signaling in neuronal and non-neuronal cells, the hM3Dq DREADD is typically used (Alexander et al. (2009) *Neuron* 63(1):27-39.; Armbruster (2007) *Proc. Natl. Acad. Sci.*, 104(12):5163-8). The hM3Dq can be activated by clozapine-N-oxide (CNO), a pharmacologically inert metabolite of the atypical antipsychotic drug clozapine (Armbruster (2007) *Proc. Natl. Acad. Sci.*, 104(12):5163-8.); Roth et al (1994) *J. Pharmacol. Exp. Ther.* 268, 1403-1410.

The hM4Di receptor is a modified human muscarinic receptor that normally couples to Gi signaling cascades and GIRK channels, is insensitive to acetylcholine or other endogenous compounds (Pei et al. (2008) *Physiology* 23:313-21). However, this modified human muscarinic receptor is strongly activated by the otherwise pharmacologically inert ligand, clozapine N-oxide (CNO). Furthermore, specificity achieved by regional and cell-type specific expression of DREADDs which allows for targeted and temporally limited suppression of neuronal excitability.

The present invention uses the eye as a portal to influence brain activity and function, in particular to treat diseases and disorders of the nervous system, such as, for example, depression. Manipulation of the brain using DREADD injections into the eye to manipulate activity of noradrenergic locus coeruleus neurons and to control the PRAM pathway and its associated pathways was neither suggested nor taught in the art. Likewise, the use of a PACAP promoter to drive DREADD expression in a specific subset of retinal ganglion cells was not taught or suggested in the art. The use of retinal stimulation of the PRAM pathway to manipulate and regulate activity of locus coeruleus neurons via natural circuit inputs allows for more physiological and clinically acceptable locus coeruleus activity patterns than would occur using prior methods of direct stimulation by expression of DREADDs directly in locus coeruleus neurons. The present invention additionally provides the use of eye drops as a method to stimulate DREADD receptors that are expressed in the eye, a technique not taught or suggested in the art.

Thus, the present invention provides a genetically encoded and highly selective 'lock-and-key' approach to controlling aberrant neural function for therapeutic goals. Activation of DREADDs through the systemic or local delivery of an agonist, will attenuate neural hyperactivity, as well as adenylyl cyclase and cAMP levels, in neurons. DREADDs can be activated in a dose-dependent manner by their agonist, thereby allowing for flexible modulation of neuronal function.

There are several techniques to determine when retinal expression of the DREADD has occurred before administering the DREADD agonist to the subject. In one technique, a physician may use a SPECTRALIS® OCT platform and proceed with a technique called Optical Coherence Tomography (OCT) to detect expression of a DREADD. The expression of a DREADD can be successfully detected if it is tagged with a fluorescent marker, e.g., GFP, tdTomato, or mCherry. As a result, DREADD expression can be monitored prior to the administration of a DREADD agonist. In a second technique, agonist-dependent activation of a DREADD can be analyzed using an electroretinogram. In a third technique, positron emission tomography (PET) can be used to detect DREADD expression after an intravenous dose of a radiolabeled agonist such as an [11C] agonist.

In one embodiment, a DREADD agonist may be administered immediately after administering a viral vector to the eye of a subject, wherein the viral vector comprises a promoter, a DREADD, and a 3' untranslated region encoded by the nucleotide sequence SEQ ID NO:1, SEQ ID NO:2, SEQ ID NO:3, SEQ ID NO:4, SEQ ID NO:6, SEQ ID NO:7, SEQ ID NO:8, SEQ ID NO:9, SEQ ID NO:10, or SEQ ID NO:11.

In another embodiment, the DREADD agonist may be administered one day after administering a viral vector to the eye of a subject, wherein the viral vector comprises a promoter, a DREADD, and a 3' untranslated region encoded by the nucleotide sequence SEQ ID NO:1, SEQ ID NO:2, SEQ ID NO:3, SEQ ID NO:4, SEQ ID NO:6, SEQ ID NO:7, SEQ ID NO:8, SEQ ID NO:9, SEQ ID NO:10, or SEQ ID NO:11.

In yet another embodiment, the DREADD agonist may be administered at three weeks, preferably four weeks, after administering a viral vector to the eye of a subject, wherein the viral vector comprises a promoter, a DREADD, and a 3' untranslated region encoded by the nucleotide sequence SEQ ID NO:1, SEQ ID NO:2, SEQ ID NO:3, SEQ ID NO:4, SEQ ID NO:6, SEQ ID NO:7, SEQ ID NO:8, SEQ ID NO:9, SEQ ID NO:10, or SEQ ID NO:11.

In another embodiment, the DREADD agonist may be administered prophylactically, prior to, at the same time, or a time after administering a viral vector to the eye of a subject, wherein the viral vector comprises a promoter, a DREADD, and a 3' untranslated region encoded by the nucleotide sequence SEQ ID NO:1, SEQ ID NO:2, SEQ ID NO:3, SEQ ID NO:4, SEQ ID NO:6, SEQ ID NO:7, SEQ ID NO:8, SEQ ID NO:9, SEQ ID NO:10, or SEQ ID NO:11.

In another embodiment, the described viral vector comprising a promoter, a DREADD, and a 3' untranslated region encoded by the nucleotide sequence SEQ ID NO:1, SEQ ID NO:2, SEQ ID NO:3, SEQ ID NO:4, SEQ ID NO:6, SEQ ID NO:7, SEQ ID NO:8, SEQ ID NO:9, SEQ ID NO:10, or SEQ ID NO:11, may be co-administered with an anti-inflammatory agent, which may be selected from a systemically-injected corticosteroid, an intravitreally-injected ketorolac, an intravitreally-injected diclofenac or other clinically acceptable anti-inflammatory agent.

The methods of the present invention may also comprise administering at least one other therapeutic agent for the treatment of a nervous system disease or disorder, which include acamprosate, agomelatine, alimemazine, alprazolam, amantadine, amfetamine, amisulpride, amitriptyline, amobarbital, amoxapine, apomorphine, apomorphine, aripiprazole, asenapine, atomoxetine, atropine, baclofen, benperidol, benztropine, biperiden, bromazepam, bromocriptine, bromperidol, brotizolam, buprenorphine, bupropion, buspirone, butobarbital, cabergoline, carbamazepine, chloral hydrate, chlordiazepoxide, chlorpheniramine, chlorpromazine, chlorprothixene, citalopram, clobazam, clomethiazole, clomipramine, clonazepam, clonidine, clorazepate, clozapine, cyclobarbital, cyproheptadine, cytisine, desipramine, desvenlafaxine, dexamfetamine, dexmethylphenidate, dextromethorphan, diazepam, dicyclomine dimenhydrinate, diphenhydramine, disulfiram, divalproex sodium, donepezil, doxacurium, doxepin, doxylamine, duloxetine, edaravone, electroconvulsive therapy, enanthate, escitalopram, estazolam, eszopiclone, ethosuximide, flunitrazepam, fluoxetine, flupenthixol, fluphenazine, flurazepam, fluspirilen, fluvoxamine, gabapentin, galantamine, glutethimide, glycopyrrolate, guanfacine, haloperidol, hexamethonium, hydrochloride, hydroxyzine, iloperidone, imipramine, ipratropium, lamotrigine, levetiracetam, levodopa, levomepromazine, levomilnacipran, lisdexamfetamine, lisuride, lithium salts, loprazolam, lorazepam, lormetazepam, mecamylamine, melatonin, melperone, memantine, meprobamate, metamfetamine, methadone, methylphenidate, mianserin, midazolam, mirtazapine, moclobemide, modafinil, modecate, motherwort, nalmefene, naltrexone, niaprazine, nimetazepam, nitrazepam, nortriptyline, olanzapine, omca, ondansetron, orphenadrine, oxazepam, oxcarbazepine, oxitropium, oxybutynin, paliperidone, paroxetine, penfluridol, pentobarbital, perazine, pergolide, pericyazine, perphenazine, phenazepam, phenelzine phenobarbital, phenytoin, pimozide, piribedil, pramipexole, pregabalin, prolixin decanoate, promethazine, propantheline bromide, prothipendyl, protriptyline, quazepam, quetiapine, ramelteon, rasagiline, reboxetine, remacemide, reserpine, riluzole, risperidone, rivastigmine, ropinirole, rotigotine, rubidium chloride, safinamide, scopolamine, secobarbital, sediten, selecten, selegiline, selegiline, sertindole, sertraline, sertraline, sevinol, sinqualone enantat, siqualone, sirtal, sodium oxybate, sodium valproate, solifenacin, stazepine, stelazine, sulpiride, suvorexant, tacrine, tegretol, telesmin, temazepam, terfluzine, tetrabenazine, thioridazine, thiothixene, tianeptine, timonil, tiotropium, tizanidine, tofisopam, tolcapone, tolterodine, topiramate, trancin, tranylcypromine, trazodone, triazolam, trifluoperaz, trifluoperazine, triftazin, trihexyphenidyl, trimipramine, tropicamide, tubocurarine, valerian, valproate, valproic acid, varenicline, venlafaxine, vilazodone, vortioxetine, zaleplon, ziprasidone, zolpidem, zopiclone, zotepine, zuclopenthixol or other neuroeptic, antidepressant or pharmacotherapeutic agents for treating any of the aforementioned disorders.

In a particular embodiment, the DREADD nucleic acid and/or DREADD agonist is delivered as a composition with at least one pharmaceutically acceptable carrier.

In some embodiments, the disease or disorder of the nervous system is a neuropsychiatric disorder. Individuals may be identified as having a neuropsychiatric disorder using the criteria set forth in the American Psychiatric Association's Diagnostic and Statistical Manual of Mental Health (DSM-5). The DSM-5 identifies disorders which are classified as neuropsychiatric disorders. Examples of neuropsychiatric disorders include: depression, seasonal affective disorder, anxiety, sleep and circadian disorders, stress disorders including Post Traumatic Stress Disorder (PTSD), Attention Deficit Hyperactivity Disorder (ADHD), autism, addiction, epilepsy, and Intensive Care Unit (ICU) psychosis.

In another embodiment, the sleep disorder is desynchronosis ("jet lag"), which is a temporary disorder that causes fatigue, insomnia, and other symptoms because of air travel across time zones. It is considered a circadian rhythm sleep disorder, which is a disruption of the internal body clock.

In some embodiments, the disease or disorder of the nervous system is a neurodegenerative disease, which includes amyotrophic lateral sclerosis (ALS), Parkinson's disease, Alzheimer's disease, and Huntington's disease.

In another embodiment, the disease or disorder of the nervous system is a cerebrovascular accident (CVA) or stroke. A DREADD nucleic acid and/or DREADD agonist may be administered to a subject to alleviate the symptoms of a cerebrovascular accident (CVA) or stroke. These symptoms include the subject having trouble remaining conscious, walking, speaking, and understanding, as well as paralysis or numbness of the face, arm, or leg.

In another embodiment, a DREADD nucleic acid and/or DREADD agonist may be administered to a subject, while the subject is treated with an additional therapeutic method for a disease or disorder of the nervous system. These additional therapeutic methods include, but are not limited to, cognitive behavioral therapy, light therapy, and electroconvulsive therapy. For example, a subject may receive a DREADD agonist while receiving light therapy for a neuropsychiatric disorder. The combined treatment methods may result in augmenting the effectiveness of the light therapy and/or reduce the frequency and dosages of light therapy protocols.

Table 2 describes diseases and disorders of the nervous system, the brain region affected, treatments, and predicted outcomes.

TABLE 2

| Disease/Disorder of the Nervous System | Brain Region Affected | Treatment | Predicted Outcome |
|---|---|---|---|
| Depression | Dysregulated SCN, Dysregulated DMH, hypoactive LC (Bowrey et al. *Depress. Anxiety.* 2017) | Activate retina with AAV2-hSyn-hM3Dq or AAV2-PACAP-hM3Dq. | Construct will restore (increase) normal firing of LC and reverse depression symptoms. |
| Seasonal Affective Disorder | Dysregulated SCN, Dysregulated DMH, hypoactive LC (Bowrey et al. *Depress. Anxiety.* 2017) | Activate retina with AAV2-hSyn-hM3Dq or AAV2-PACAP-hM3Dq. | Construct will restore (increase) normal firing of LC and reverse depression symptoms. |
| Stress Disorder | Hyperactive noradrenergic/LC system (Valentino R J, Foote S L *J Neurosci.* 1988 Mar.; 8(3): 1016-25; Bremner et al. *Synapse.* 1996 pp 23: 39-51) | Inhibit retina with AAV2-hSyn-hM4Di or AAV2-PACAP-hM4Di. | Construct will restore (decrease) normal firing of LC and prevent stress symptoms. |
| Anxiety | Hyperactive noradrenergic/LC system (Bremner et al. *Synapse.* 1996 pp 23: 39-51) | Inhibit retina with AAV2-hSyn-hM4Di or AAV2-PACAP-hM4Di. | Construct will restore (decrease) normal firing of LC and prevent anxiety symptoms. |
| Autism | Dysregulation of LC firing (*Annu. Rev. Neurosci.* 2005.28: 403-450) | Activate retina with AAV2-hSyn-hM3Dq or AAV2-PACAP-hM3Dq. | Construct will enhance tonic firing of LC, reducing autism-related deficits in behavioral flexibility. |
| Substance Use Disorder | Hyperactivity of LC during withdrawal from drug (Hooshmand et al. *Neuroscience Letters* 636, 276-281) | Inhibit retina with AAV2-hSyn-hM4Di or AAV2-PACAP-hM4Di. | Construct will restore (decrease) normal firing of LC and prevent withdrawal symptoms. |
| Epilepsy | Anti-epileptic treatments appear to be mediated by LC (Fornai et al. *EJN.* 33: 2169-2178, 2011) | Activate retina with AAV2-hSyn-hM3Dq or AAV2-PACAP-hM3Dq to activate LC. | Secondary LC activation will enhance antiepileptic treatments such as vagus nerve stimulation. |
| Intensive Care Unit Psychosis | Dysregulation of SCN (Barrosso et al. *Lighting Res. Technol.* 2013; 45: 197-216) | Activate retina with AAV2-hSyn-hM3Dq or AAV2-PACAP-hM3Dq to activate LC at dawn. | Retina activation at dawn will synchronize SCN, improving psychosis symptoms. |
| Desynchronosis ("jet lag") | When travelling across time zones, the body clock is out of synchronization with the destination time | Activate retina with AAV2-hSyn-hM3Dq or AAV2-PACAP-hM3Dq at dawn of the destination time. | Retina activation at dawn of the destination time will synchronize SCN, improving jetlag symptoms. |
| Disease/Disorder of the Nervous System | Brain Region Affected | Treatment | Predicted Outcome |
| Amyotrophic Lateral Sclerosis | Bunina bodies in the locus ceruleus pigmented neurons (Iwanaga et al. *Clin Neuropathol.* 1997; 16: 23-6) | Activate retina with AAV2-hSyn-hM3Dq or AAV2-PACAP-hM3Dq at dawn of the destination time. | Secondary LC activation will reduce ALS symptoms. |
| Parkinson's Disease | Lewy pathology and cell loss in the LC precedes that of other key PD-relevant brain structures (Vermeiren. Neurochemistry International Volume 102, January 2017, Pages 22-32) | Chronically activate retina with AAV2-hSyn-hM3Dq or AAV2-PACAP-hM3Dq. | Retinal activation will be protective against the development of lewy pathology in the LC and will activate remaining LC neurons to compensate for lost neurons. |
| Alzheimer's Disease | Loss of locus coeruleus neurons (Bondareff et al. *Lancet.* 1981 Apr. 4; 1(8223): 783-4) | Chronically activate retina with AAV2-hSyn-hM3Dq or AAV2-PACAP-hM3Dq. | Retinal activation will reduce loss of locus coeruleus neurons, and activate remaining neurons to compensate for lost neurons, reducing cognitive symptoms of Alzheimer's disease. |

TABLE 2-continued

| Disease/Disorder of the Nervous System | Brain Region Affected | Treatment | Predicted Outcome |
|---|---|---|---|
| Huntington's Disease | Reduced cell numbers and length of locus coeruleus (Zweig et al. *Archives of Neurology.* 1992. 49(2): 152-6) | Chronically activate retina with AAV2-hSyn-hM3Dq or AAV2-PACAP-hM3Dq. | Retinal activation will reduce loss of locus coeruleus neurons, and activate remaining neurons to compensate for lost neurons, slowing the time course of symptoms of Huntington's disease. |
| Stroke | Reductions in norepinephrine in LC following cerebral infarction (Robinson R. G., 1979. *Science.* 205: pp. 707-710) | Chronically activate retina with AAV2-hSyn-hM3Dq or AAV2-PACAP-hM3Dq. | Secondary LC activation will increase norepinephrine, improving symptom outcomes. |

The nucleic acids of the present invention may be delivered to a cell, e.g., neuron, by any known method. For example, the nucleic acids can be delivered via synthetic delivery systems, liposomes, nanoparticles, or viral vectors. The nucleic acid molecules encoding the DREADD may be contained within an expression vector, particularly a viral vector such as an adeno-associated viral vector. The nucleic acid molecules (or vectors) may be directly delivered to the target site, e.g., by microinjection. For example, the nucleic acid molecules or vectors may be administered, e.g., by injection to the intraocular space and/or retina. Intraocular injections may include intravitreal injections, sub-internal limiting membrane injections, and sub-retinal injections.

Examples of viral vectors include, without limitation, lentiviral, retroviral, herpesviral, e.g., replication-defective herpes simplex virus (HSV), adenoviral, and adeno-associated viral vectors. In a particular embodiment, the vector is an AAV vector. The AAV vector can be of any AAV serotype. For example, the AAV vector can be, without limitation, AAV1, AAV2, AAV3, AAV4, AAV5, AAV6, AAV7, AAV8, AAV9, AAV10, AAV11, AAV12, and hybrids thereof. For example, an AAV vector can be a combinatorial hybrid of 2, 3, 4, 5, or more serotypes. AAV vectors can have one or more of the AAV wild-type genes deleted in whole or part. In a particular embodiment, the AAV vector is AAV2.

As explained above, DREADDs are engineered G-protein coupled receptors which are activated by otherwise inert drug-like small molecules (reviewed in Urban et al. (2015) *Ann. Rev. Pharmacol. Toxicol.,* 55: 399-417; incorporated herein by reference). Methods of generating DREADDs are known in the art (see, e.g., Dong et al. (2010) *Nat. Protoc.,* 5(3):561-73).

In a particular embodiment, the DREADD is based on the muscarinic receptor (e.g., human muscarinic receptor). In another particular embodiment, the DREADD is a KORD (kappa opioid receptor-DREADD (e.g., human KOR). For example, the KORD may be a G-protein coupled (e.g., Gi-coupled) kappa-opioid receptor DREADD wherein the inert ligand or agonist is salvinorin B (salB). In a particular embodiment, the DREADD is coupled with Gi.

In a particular embodiment, the DREADD is hM4Di (human M4 muscarinic cholinergic Gi-coupled DREADD. In a particular embodiment, the DREADD is human muscarinic acetylcholine receptor M4 (e.g., GenBank Accession No. NP_000732, Gene ID: 1132) comprising two-point mutations: a substitution at Y113 (e.g., Y113C) and a substitution at A203 (e.g., A203G). PCT Publication No. WO 2015/136247 (incorporated herein by reference) also provides a nucleic acid sequence encoding hMD4i. A plasmid encoding hM4Di is available commercially as plasmid 45548 (Addgene, Cambridge, MA, www.addgene.org/45548).

In a particular embodiment, the DREADD is coupled with Gq. In a particular embodiment, the DREADD is Gq-coupled human M3 muscarinic receptor (hM3Dq) (see, e.g., Alexander et al. (2009) *Neuron* 63(1): 27-39; Armbruster et al. (2007) *Proc. Natl. Acad. Sci.,* 104(12):5163-5168; Alexander et al. (2009) *Neuron* 63(1):27-39). A plasmid encoding hM3Dq is available commercially as plasmid 44361 (Addgene, Cambridge, MA, www.addgene.org/44361).

In a particular embodiment, the agonist is clozapine N-oxide, DREADD agonist 21 (Tocris Bioscience, Bristol, UK; 11-(1-piperazinyl)-5H-dibenzo[b,e][1,4]diazepine), salvinorin B, clozapine, olanzapine, or perlapine (Tocris Bioscience, Bristol, UK; 6-(4-methyl-1-piperazinyl)-11H-dibenz[b,e]azepine); Chen et al. (2015) ACS Chem. Neurosci., 6(3):476-84).

The nucleic acids encoding DREADDs may be under the control of a neuron specific promoter. In a particular embodiment, the neuron-specific promoter is synapsin (e.g., Kugler et al. (2003) *Gene Ther.,* 10:337-47). The synapsin promoter (e.g., human synapsin promoter) drives production of a DREADD (e.g., hM4D(Gi) or hMD3(Dq)) in a large percentage of neurons.

In a particular embodiment, the neuron-specific promoter is a pituitary adenylate cyclase activating polypeptide (PACAP) promoter, a melanopsin promoter, or a promoter that expresses in retinal neurons that project to SCN.

In another embodiment, the neuron-specific promoter is PRSx8. PRSx8 is based on an upstream regulatory site in the human DBH promoter and drives high levels of expression in adrenergic neurons.

In yet another embodiment, the neuron-specific promoter is preprotachykinin-1 promoter (TAC-1).

The nucleic acid sequences of several promoter-driven DREADDs are described. They include, but are not limited to, PACAP-hM3D(Gq)-mCherry (SEQ ID: 1), TAC-1-hM4D(Gi)-mCherry (SEQ ID NO:2), PRSx8-HA-hM3D (Gq) (SEQ ID NO:3), PRSx8-HA-hM4D(Gi) (SEQ ID NO:4), PACAP-hM3D(Gq) (SEQ ID NO:6), PRSx8-hM3D (Gq) (SEQ ID NO:7), PRSx8-hM4D(Gi) (SEQ ID NO:8), and TAC-1-hM4D(Gi) (SEQ ID NO:9), TAC-1-hM3D(Gq)-mCherry (SEQ ID NO:10) and PACAP-hM4D(Gi)-mCherry (SEQ ID NO:11).

The agonist of a DREADD preferentially binds and activates the administered DREADD receptor over other receptors (e.g., a selective agonist). It is desirable to use a DREADD agonist which is inert or has little or no biological effects other than stimulating the DREADD. For example, the agonist may be a ligand of the DREADD.

In a particular embodiment, the agonist is clozapine N-oxide (CNO) or salvinorin B (salB). The DREADD agonist may be delivered systemically to the subject (e.g., orally, topically (e.g., to the skin) or directly to the eye (e.g., injection or eye drops).

Pharmaceutical Compositions and Administration

The composition may be administered by any suitable means, including ocular, oral, parenteral, intramuscular, intravenous, intra-arterial, intraperitoneal, subcutaneous, topical, inhalatory, transdermal, intrapulmonary, intrarectal, intramuscular, and intranasal administration.

In one particular embodiment, the nucleic acid composition is administered by injection (e.g., microinjection to the retina, intravitreal injection, etc.).

An example of administering a DREADD to the eye of mice has been described (Li et al. (2016). *Proc. Natl. Acad. Sci.,* 113(7):1937-1942. In this report, Li et al. injected an AAV vector expressing a DREADD (a mutant M3 muscarinic G protein-coupled receptor (GPCR) hM3Dq to selectively activate Gq/11 signaling) into the eyes of mice using methods described in Park et al. (2008) Science 322(5903): 963-966. The Gq/11-coupled designer GPCR in Li could not be activated by its natural ligand (acetylcholine), but became activated by clozapine N-oxide (CNO), an otherwise pharmacologically inert compound (Farrell et al. (2013) *Brain Res* 1511:6-20). Briefly, mice were anaesthetized with ketamine and xylazine and the vector was injected into the vitreous bodies using a glass micropipette coupled to a Hamilton microsyringe. The micropipette was inserted in the peripheral retina, just behind the or a serrata, and was deliberately angled to avoid damage to the lens.

In another particular embodiment, the composition comprising the agonist is administered systemically (e.g., orally), topically (e.g., to the skin) or to the eye (e.g., via eye drops).

Compositions comprising the DREADD agonist, e.g., clozapine N-oxide, DREADD agonist 21, salvinorin B, clozapine, olanzapine, or perlapine, and a carrier are encompassed by the present invention, particularly compositions suitable for ocular administration, particularly topical administration to the eye, for example, sterile eye drops or ointment. In a particular embodiment, the composition is an aqueous formulation with a pH physiologically compatible with the eye (e.g., a pH in the range from about 4 to about 8, about 5.5 to about 8, or about 6.0 to about 7.5).

In a particular embodiment, the composition is an aqueous formulation having isotonic and physiological characteristics suitable for ocular administration. The compositions may also be modified to increase the residence time of the compounds in the eye, provide a sustained release of compounds, and/or avoid toxicity and increase ocular tolerability.

In a particular embodiment, the tonicity of the composition approximates physiological tonicity (e.g., 0.9% saline). Compounds such as, without limitation: sodium chloride, potassium chloride, calcium chloride, dextrose and/or mannitol, may be added. In a particular embodiment, the osmolality of the composition is about 150 to about 450 mOsm or about 250 to about 350 mOsm.

In a particular embodiment, the composition may further comprise a compound which soothes the eye; reduces surface tension and improves wettability; and/or enhances the viscosity of the composition (e.g., to a viscosity of about 10 to about 100 or about 25 to about 50 centipolses), such agents include, without limitation: polyols (e.g., tyloxapol, glycerol, propylene glycol, ethylene glycol, polyethylene glycol), cellulose derivatives (e.g., hydroxyethylcellulose, hypromellose, hydroxypropylmethyl cellulose, methylcellulose, carboxymethylcellulose sodium, hydroxylpropylcellulose), dextran, gelatin, vinyl polymers (e.g., polyvinyl alcohol, polyvinyl pyrrolidine), polysorbate 80, povidone, carbomers, and polysaccharides/glycosaminoglycans (e.g., hyaluronan, chondroitin sulfate).

In a particular embodiment, the composition comprises an antioxidant. In a particular embodiment, the composition comprises a preservative (e.g., quaternary ammonium salts (e.g., benzalkonium chloride, benzethonium chloride, cetalkonium chloride, cetrimide, benzododecinium bromide and benzoxonium chloride), alkyl-mercury salts of thiosalicylic acid, parabens, chelating agents, chlorobutanol, boric acid, sorbic acid, phenylethanol, and the like).

In general, the pharmaceutically acceptable carrier of the composition is selected from the group of diluents, preservatives, solubilizers, emulsifiers, adjuvants and/or carriers. The compositions can include diluents of various buffer content (e.g., Tris HCl, acetate, phosphate), pH and ionic strength; and additives such as detergents and solubilizing agents (e.g., polysorbate 80), anti-oxidants (e.g., ascorbic acid, sodium metabisulfite), preservatives (e.g., Thimerosal, benzyl alcohol) and bulking substances (e.g., lactose, mannitol). The compositions can also be incorporated into particulate preparations of polymeric compounds such as polyesters, polyamino acids, hydrogels, polylactide/glycolide copolymers, ethylenevinylacetate copolymers, polylactic acid, polyglycolic acid, etc., or into liposomes. Such compositions may influence the physical state, stability, rate of in vivo release, and rate of in vivo clearance of components of a pharmaceutical composition of the present invention (see, e.g., Remington's Pharmaceutical Sciences and Remington: The Science and Practice of Pharmacy). The pharmaceutical composition of the present invention can be prepared, for example, in liquid form, or can be in dried powder form (e.g., lyophilized for later reconstitution).

The therapeutic agents described will generally be administered to a patient as a pharmaceutical preparation. The term "patient" refers to human or animal subjects. The compositions of the present invention may be employed therapeutically or prophylactically, under the guidance of a physician or veterinarian.

The compositions comprising the agent of the present invention may be conveniently formulated for administration with any pharmaceutically acceptable carrier(s). The concentration of agent in the chosen medium may be varied and the medium may be chosen based on the desired route of administration of the pharmaceutical preparation. Except insofar as any conventional media or agent is incompatible with the agent to be administered, its use in the pharmaceutical preparation is contemplated.

The dose and dosage regimen of the agent according to the present invention that is suitable for administration to a particular patient may be determined by a physician considering the patient's age, sex, weight, general medical condition, and the specific condition for which the agent is being administered to be treated or prevented and the severity thereof. The physician may also take into account the route of administration, the pharmaceutical carrier, and the agent's biological activity. Selection of a suitable pharmaceutical preparation will also depend upon the mode of administration chosen.

A pharmaceutical preparation of the present invention may be formulated in dosage unit form for uniformity and for ease of administration. The dosage unit form refers to the physical discrete unit of the pharmaceutical preparation appropriate for a patient undergoing treatment therapy. Each dosage should contain a quantity of active ingredient, e.g., DREADD agonist, calculated to produce the desired effect in association with a selected pharmaceutical carrier.

Procedures for determining the appropriate dosage unit are well known to those skilled in the art. For example, dosage units may be proportionately increased or decreased based on the weight of the subject. Appropriate concentrations for alleviation or prevention of a particular condition (disease or disorder of the nervous system) may be determined by dosage concentration curve calculations, as known in the art.

In one embodiment, the concentration of the therapeutic agent, e.g., DREADD agonist, will range from 0.1 mg/kg-100 mg/kg depending on subject species.

After administration of the DREADD, a pharmaceutical preparation comprising the therapeutic agent, e.g. DREADD agonist, may be administered at appropriate intervals until the pathological symptoms are reduced or alleviated, after which the dosage may be reduced to a maintenance level.

The first dose of the of a DREADD agonist may be administered immediately after intraocularly or intravitreally administering a viral vector, wherein the viral vector comprises a promoter, a DREADD, and a 3' untranslated region encoded by the nucleotide sequence SEQ ID NO:1, SEQ ID NO:2, SEQ ID NO:3, SEQ ID NO:4, SEQ ID NO:6, SEQ ID NO:7, SEQ ID NO:8, SEQ ID NO:9, SEQ ID NO:10, or SEQ ID NO:11.

In another embodiment, the DREADD agonist may be administered one day after intraocularly or intravitreally administering a viral vector, wherein the viral vector comprises a promoter, a DREADD, and a 3' untranslated region encoded by the nucleotide sequence SEQ ID NO:1, SEQ ID NO:2, SEQ ID NO:3, SEQ ID NO:4, SEQ ID NO:6, SEQ ID NO:7, SEQ ID NO:8, SEQ ID NO:9, SEQ ID NO:10, or SEQ ID NO:11.

In yet another embodiment, the DREADD agonist may be administered at three weeks, preferably four weeks, after intraocularly or intravitreally administering a viral vector, wherein the viral vector comprises a promoter, a DREADD, and a 3' untranslated region encoded by the nucleotide sequence SEQ ID NO:1, SEQ ID NO:2, SEQ ID NO:3, SEQ ID NO:4, SEQ ID NO:6, SEQ ID NO:7, SEQ ID NO:8, SEQ ID NO:9, SEQ ID NO:10, or SEQ ID NO:11.

The appropriate time to administer the DREADD agonist may be determined by three methods known in the art. The first method visualizes DREADD expression using optimal coherence tomography (OCT). The second method is through the analysis of an electroretinogram wave during agonist-dependent activation of a DREADD. The third method occurs by using positron emission tomography (PET) after an intravenous dose of a radiolabeled agonist such as an [$^{11}$C] agonist. It is expected that the optimal first dose of agonist may be within the range of 3-4 weeks following administration of the DREADD nucleic acid molecules.

In another embodiment, the pharmaceutical preparation comprising the therapeutic agent, e.g., DREADD agonist, may be administered at appropriate daily intervals, for example, at least once per day, at least twice per day, at least three times per day, or until pathological symptoms of a disease or disorder of the nervous system are reduced or alleviated.

The appropriate daily interval of administration of the therapeutic agent, e.g., DREADD agonist, may depend on the condition of the patient, e.g., severity of nervous system disease or disorder.

Toxicity and efficacy, for example, therapeutic, preventative, of the particular formulas described can be determined by standard pharmaceutical procedures such as in vitro, in cell cultures, ex vivo, or on experimental animals. The data obtained from these studies can be used in formulating a range of dosage for use in human. The dosage may vary depending upon form and route of administration. Dosage amount and interval may be adjusted individually to levels of the active ingredient which are sufficient to deliver a therapeutically or prophylactically effective amount.

Kits

The present invention also provides kits comprising one or more components including, but not limited to, the viral vectors, promoter, and DREADD, as discussed, in association with one or more additional components including, but not limited to, a pharmaceutically acceptable carrier and the DREAD agonist. The viral vectors, promoter, DREADD composition and/or the DREAD agonist can be formulated as pure compositions or in combination with a pharmaceutically acceptable carrier, in a pharmaceutical composition.

Kits may also include primers, buffers, and probes along with instructions for determining elevated levels of nucleic acid, proteins, or protein fragments of the DREADDs.

In one embodiment, a kit includes a viral vector, a promoter, a DREADD composition of the invention or a pharmaceutical composition thereof in one container and a DREADD agonist or a pharmaceutical composition thereof in another container (e.g., in a sterile glass or plastic vial).

If the kit includes a pharmaceutical composition for parenteral administration to a subject, the kit can include a device for performing such administration. For example, the kit can include one or more hypodermic needles or other injection devices as discussed above.

The kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

General Methods

Standard methods in molecular biology are described in Sambrook, Fritsch and Maniatis (1982 & 1989 2$^{nd}$ Edition, 2001 3$^{rd}$ Edition) *Molecular Cloning, A Laboratory Manual*, Cold Spring Harbor Laboratory Press, Cold Spring Harbor, NY; Sambrook and Russell (2001) *Molecular Cloning, 3$^{rd}$ ed.*, Cold Spring Harbor Laboratory Press, Cold Spring Harbor, NY; Wu (1993) *Recombinant DNA*, Vol. 217, Academic Press, San Diego, CA). Standard methods also appear in Ausbel, et al. (2001) *Current Protocols in Molecular Biology, Vols.* 1-4, John Wiley and Sons, Inc. New York, NY, which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science, Vol.* 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science, Vol.* 2, John Wiley and Sons, Inc., New York; Ausubel, et al. (2001) *Current Protocols in Molecular Biology, Vol.* 3, John Wiley and Sons, Inc., NY, NY, pp. 16.0.5-16.22.17; Sigma-Aldrich, Co. (2001) *Products for Life Science Research*, St. Louis, MO; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology*, Vol. 1, John Wiley and Sons, Inc., New York; Harlow and Lane (1999) *Using Antibodies*, Cold Spring Harbor Laboratory Press, Cold Spring Harbor, NY; Harlow and Lane, supra). Standard techniques for characterizing ligand/receptor interactions are available (see, e.g., Coligan, et al. (2001) *Current Protocols in Immunology*, Vol. 4, John Wiley, Inc., New York).

EXAMPLES

Example 1

The Excitatory hM3Di DREADD in the Retina

Weight loss is a common feature of depression in humans and depression-like behavior in animals (American Psychiatric Association, DSM-5, 2013; Liu et al. *Behavior. Brain Res.,* 305:148-156, 2016). The effect of DREADD activation on depression-associated weight loss was studied in rats.

Rats were administered AAV vectors with the human synapsin promoter (hSyn) encoding hM3Dq (G(q)) DREADD (AAV-hSyn-hM3Di) or control vector (hSyn-GFP) by intravitreal injection (IVI). After allowing 4 weeks for expression of the hM3Di DREADD, the rats were housed in total darkness for 24 hours a day. The total darkness exposure is an environmental condition which leads to depression-like behavior in animals (Gonzalez et al. *Proc. Natl. Acad. Sci.,* 105(12):4898-903, 2008). The agonist CNO was administered once per day to activate retinal cells in in animals expressing hM3Di DREADD only.

FIG. 1 shows weight loss in all animals for the first three days of total dark-rearing. In the following four days, the animals with hM3D1 DREADD-activated retinas recovered from weight loss, while animals administered hSyn-GFP control vectors continued to lose weight. The recovery from weight loss indicated that hM3Di DREADD-activated retinas reduced depression-associated behavior induced by constant dark-rearing.

Example 2

DREADD Expression and Function in Retinal Cells Via Intravitreal Injection

FIGS. 2A-D show DREADD expression four weeks following DREADD administration. Rats were intravitreally administered AAV-hSyn-hM4Di. FIG. 2A shows transfections of the DREADD in retinal cells. FIG. 2B shows DREADD terminal transport to suprachiasmatic nucleus. Following confirmed DREADD expression, electoretinography (ERG) was performed. FIG. 2C shows inhibition of the ERG wave 20 minutes following CNO agonist administration (by intraperitoneal injection), indicating decreased retinal activity. FIG. 2D shows DREADD activation with eye drops. Eye drops were administered and ERG readings were recorded 10 minutes and 20 minutes thereafter. Similar to systemic delivery, eyedrops decreased function in retinal cells at both timepoints.

Example 3

DREADD Activation of Retinal Cells Prevents the Development of Light Deprivation-Induced Depression-Like Behavior Rats were administered AAV vectors encoding hM3Dq (G(q)) with the hSyn promoter(AAV-hSyn-hM3Di) or control vector (h-Syn-GFP) by intravitreal injection (IVI) or no injection. After allowing 4 weeks for expression of the hM3Di DREADD, the rats were housed in total darkness for 24 hours a day. The total darkness exposure is an environmental condition which leads to depression-like behavior in animals (Gonzalez et al. *Proc. Natl. Acad. Sci.,* 105(12): 4898-903, 2008). The agonist CNO was administered once per day to activate retinal cells in in animals expressing hM3Di DREADD only.

FIGS. 3A-F show DREADD activation of retinal cells preventing the development of light deprivation-induced depression-like behavior. FIG. 3A shows percentage of weight change in all animals for the first eight weeks of total dark-rearing. GFP animals lost weight, control animals failed to gain weight, and hM3Dq animals gained weight, as expected. The recovery from weight loss indicates that DREADD-activated retinas reduced depression-associated behavior induced by constant dark-rearing. Behavioral measures of other depression like behavior was measured. The saccharin preference test showed control and GFP animals preferred saccharin less than hM3Dq animals (FIG. 3B) and hM3Dq animals had greater swimming and less immobility during the forced swim test (FIG. 3C) that both control groups, indicating the absence of depression-like behavior in hM3Dq animals. The construct did not induce anxiety like behaviors (FIG. 3D and FIG. 3E), and there was no effect on general locomotor behavior (FIG. 3F).

Example 4

DREADD Activation of Retinal Cells in Constant Darkness Prevents Apoptosis in Locus Coeruleus Three groups of rats were either administered AAV vectors encoding hM3Dq (G(q)) with the hSyn promoter or control vector (GFP) by intravitreal injection (IVI) or no injection (DD-Control). After 4 weeks to allow for expression of the excitatory DREADD, the rats were housed in total darkness for 24 hours a day. The agonist CNO was administered once per day to both hM3Dq and GFP animals, activating retinal cells in G(q) animals only. A fourth group of rats was reared in standard dark/light conditions (DL-Control) as a comparison. Following the rearing period, brains were sectioned and were stained by immunohistochemistry with tyrosine hydroxide (TH), to define the boundary of locus coeruleus, dull gray; example locus coeruleus boarder shown in FIG. 4D), and the p85 fragment of PARP, an in situ marker of apoptosis (light gray). FIGS. 4A-E show DREADD activation of retinal cells in constant darkness prevents apoptosis in locus coeruleus. Apoptosis was only observed in DD-control and DD-GFP animals (those without any retinal activation). Apoptosis was not observed in DD-Hm3Dq and DL-Control animals (those with daily retinal activation). The amount of apoptosis was quantified by measuring the intensity of fluorescence that was generated by p85 PARP staining (FIG. 4E).

Example 5

PACAP-DREADD Expression in Melanopsin (+) Cells Following Intravitreal Injection (IVI) In the absence of available melanopsin-based agents to specifically target intrinsically photosensitive retinal ganglion cells (ipRGCs) in non-transgenic models, a pituitary adenylate cyclase-activating polypeptide (PACAP), which is co-expressed in melanopsin expressing retinal cells (Hannibal *J Neurosci.*, 2002), was used to generate a PACAP promoter to drive excitatory DREADDs (PACAP-Hm3Dq) in melanopsin immuno-reactive cells.

Retinae were double stained by fluorescence immunohistochemistry for mCherry (the fluorescent tag fused to the hM3Dq gene, in this construct) and melanopsin. The images from both channels were co-localized. Cells which are overlapping indicate co-expression of hM3Dq and melanopsin. FIG. 5A-FIG. 5C. Almost all PACAP-Hm3Dq (+) cells are immuno-reactive for melanopsin as assessed by the co-localization, indicating that the PACAP promoter can selectively drive expression of DREADDs in melanopsin cells.

Example 6

DREADD Activation of PACAP Cells Driven by a PACAP-Specific Promoter Prevents Depression Associated Weight Loss Animals that had excitatory PACAP-driven DREADDs expressed in their retinas were designated as DD-PACAP and animals that had non-activating control virus expressed in their retinas were designated as DD-GFP. All animals were housed in total darkness for 24 hours a day, an environmental condition known to lead to depression-like behavior in animals (Gonzalez and Aston-Jones PNAS. 2008). The agonist CNO was administered once per day activating retinal cells in G(q) animals only.

FIG. 6 displays weight loss in DD-GFP animals for the first eight weeks of total dark-rearing. As hypothesized, animals with PACAP-driven DREADD (DD-PACAP) activated retinas gained weight. Therefore, the DREADD activation of the PACAP (+) retinal cells significantly reduced the depression-associated behavior induced by constant dark-rearing.

The present invention is not to be limited in scope by the specific embodiments described above. Indeed, various modifications of the invention in addition to those described will become apparent to those skilled in the art from the foregoing description and the accompanying figures. Such modifications may be made without departing from the scope and spirit of the present invention, and are intended to fall within the scope of the appended claims.

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The invention claimed is:

1. A kit comprising a) a viral vector, wherein the viral vector comprises the sequence set forth by SEQ ID NO:11 encoding a promoter, a hM4D DREADD, and a 3' untranslated region; and b) an agonist to the DREADD.

2. A method of delivery of a DREADD to the retina of a subject to control activation of the Photic Regulation of Arousal and Mood (PRAM) pathway comprising:

a) a administering an effective amount of a viral vector to the eye of the subject, wherein the viral vector comprises SEQ ID NO: 11 encoding a promoter, a hM4D DREADD, and a 3' untranslated region;

b) expressing the DREADD of step (a) prior to administration of an agonist to the DREADD; and c) administering to the subject an agonist to the expressed DREADD to control activation of the PRAM pathway.

*     *     *     *     *